United States Patent
Smets et al.

(10) Patent No.: US 10,092,485 B2
(45) Date of Patent: Oct. 9, 2018

(54) BENEFIT AGENT DELIVERY PARTICLE

(71) Applicant: Encapsys, LLC, Appleton, WI (US)

(72) Inventors: Johan Smets, Stromberg-Bever (BE); An Pintens, Stromberg-Bever (BE); Laura Orlandini, Le Mont sur Lausanne (CH); Dorothy Peggy Sands, Appleton, WI (US)

( * ) Notice: Subject to any disclaimer, the term of this patent is extended or adjusted under 35 U.S.C. 154(b) by 0 days.

(21) Appl. No.: 14/787,918

(22) PCT Filed: Oct. 2, 2014

(86) PCT No.: PCT/US2014/058857
§ 371 (c)(1),
(2) Date: Oct. 29, 2015

(87) PCT Pub. No.: WO2015/051139
PCT Pub. Date: Apr. 9, 2015

(65) Prior Publication Data
US 2016/0058678 A1 Mar. 3, 2016

Related U.S. Application Data

(60) Provisional application No. 61/886,803, filed on Oct. 4, 2013.

(51) Int. Cl.
| | | |
|---|---|---|
| A61K 8/11 | (2006.01) |
| C11D 3/50 | (2006.01) |
| C11D 17/00 | (2006.01) |
| A61Q 13/00 | (2006.01) |
| A61K 8/81 | (2006.01) |
| A61Q 5/02 | (2006.01) |
| A61Q 5/12 | (2006.01) |
| A61Q 15/00 | (2006.01) |
| A61Q 19/00 | (2006.01) |
| C11D 3/37 | (2006.01) |
| C11D 11/00 | (2006.01) |
| C11D 17/04 | (2006.01) |
| C11D 17/06 | (2006.01) |

(52) U.S. Cl.
CPC ............ A61K 8/11 (2013.01); A61K 8/8152 (2013.01); A61K 8/8164 (2013.01); A61Q 5/02 (2013.01); A61Q 5/12 (2013.01); A61Q 13/00 (2013.01); A61Q 15/00 (2013.01); A61Q 19/00 (2013.01); A61Q 19/007 (2013.01); C11D 3/373 (2013.01); C11D 3/50 (2013.01); C11D 3/505 (2013.01); C11D 11/0017 (2013.01); C11D 17/0008 (2013.01); C11D 17/0017 (2013.01); C11D 17/0039 (2013.01); C11D 17/042 (2013.01); C11D 17/06 (2013.01); A61K 2800/54 (2013.01); A61K 2800/591 (2013.01); A61K 2800/624 (2013.01); A61K 2800/652 (2013.01)

(58) Field of Classification Search
None
See application file for complete search history.

(56) References Cited

U.S. PATENT DOCUMENTS

| | | | |
|---|---|---|---|
| 4,233,178 A | 11/1980 | Fuchigami | |
| 4,533,599 A | 8/1985 | Okumuru et al. | |
| 4,711,749 A * | 12/1987 | Kosaka | B01J 13/18 264/4.7 |
| 2009/0253828 A1 * | 10/2009 | Van Den Abbeele | B01J 13/02 523/201 |
| 2011/0269658 A1 * | 11/2011 | Dihora | A61K 8/11 510/119 |

OTHER PUBLICATIONS

Choi (Preparation and characterization of microcapsules containing perfumes with different polymer shells) (Year: 2002).*
Shulkin, Anna, "Styrene-Maleic Anhydride and Styrene-Maleimide Based Copolymers as Building Blocks in Microencapsulation Procedures" (2002). Open Access Dissertations and Theses. Paper 1492. http://digitalcommons.mcmaster.ca/opendissertations/1492.

* cited by examiner

Primary Examiner — Robert A Wax
Assistant Examiner — Quanglong N Truong
(74) Attorney, Agent, or Firm — Benjamin Mieliulis

(57) ABSTRACT

The present invention relates to benefit agent containing delivery particles, compositions comprising said particles, and processes for making and using the aforementioned particles and compositions. When employed in compositions, for example, cleaning or fabric care compositions, such particles increase the efficiency of benefit agent delivery, thereby allowing reduced amounts of benefit agents to be employed. In addition to allowing the amount of benefit agent to be reduced, such particles allow a broad range of benefit agents to be employed.

18 Claims, No Drawings

BENEFIT AGENT DELIVERY PARTICLE

CROSS REFERENCE TO RELATED APPLICATIONS

Appvion, Inc. (formerly known as Appleton Papers Inc.) and The Procter & Gamble Company executed a Joint Research Agreement on or about Nov. 28, 2005 and this invention was made as a result of activities undertaken within the scope of the Joint Research Agreement between Appvion, Inc. and The Procter & Gamble Company that was in effect on or before the date of this invention.

FIELD OF INVENTION

The present application relates to benefit agent containing delivery particles, compositions comprising such particles, and processes for making and using such particles and compositions.

BACKGROUND OF THE INVENTION

Benefit agents, such as perfumes, silicones, waxes, flavors, vitamins and fabric softening agents, are expensive and/or generally less effective when employed at high levels in consumer products, for example, personal care compositions, cleaning compositions, and fabric care compositions. As a result, there is a desire to maximize the effectiveness of such benefit agents. One method of achieving such objective is to improve the delivery efficiencies of such benefit agents. Unfortunately, it is difficult to improve the delivery efficiencies of benefit agents as such agents may be lost due to the agents' physical or chemical characteristics, or such agents may be incompatible with other compositional components or the situs that is treated. In an effort to improve such delivery efficiency, benefit agents have been encapsulated. Unfortunately, encapsulated benefit agents leak benefit agent over time, possibly via diffusion. Such leakage can be minimized by increasing the encapsulate's shell strength. However, when an encapsulate's shell strength is increased, benefits such as sustained benefit release with time are compromised as the encapsulate no longer releases sufficient benefit agent in response to moderate pressure stimuli. Thus, what is needed is an encapsulate that exhibits decreased benefit agent leakage, yet which releases benefit agent in response to moderate pressure stimuli.

Here, Applicants recognized that the source of the problem giving rise to shell strength/benefit agent release dilemma was the nature of encapsulate's crosslink density. While not being bound by theory, Applicants believe that as the shell crosslink density increases, the encapsulate's rigidity increases due to a loss of the shell's degrees of freedom and the encapsulate's benefit agent leakage decreases as the pathway through the shell is more tortuous. Thus, Applicant's recognized that, to exhibit low leakage and sustained release, an encapsulate requires a high number of flexible/weak shell cross links. Such an encapsulate can, among other benefits, provide increased wet fabric odor benefits.

Herein, Applicants provide a solution to the aforementioned dilemma.

SUMMARY OF THE INVENTION

The present invention relates to benefit agent containing delivery particles comprising a core material and a wall material that encapsulates the core material. The present invention also relates to compositions comprising said particles, and processes for making and using such particles and compositions.

DETAILED DESCRIPTION OF THE INVENTION

Definitions

As used herein "consumer product" means baby care, beauty care, fabric & home care, family care, feminine care, health care, snack and/or beverage products or devices intended to be used or consumed in the form in which it is sold, and not intended for subsequent commercial manufacture or modification. Such products include but are not limited to fine fragrance (e.g. perfumes, colognes, eau de toilettes, after-shave lotions, pre-shave, face waters, tonics, and other fragrance-containing compositions for application directly to the skin), diapers, bibs, wipes; products for and/or methods relating to treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use; and shaving products, products for and/or methods relating to treating fabrics, hard surfaces and any other surfaces in the area of fabric and home care, including: air care, car care, dishwashing, fabric conditioning (including softening), laundry detergency, laundry and rinse additive and/or care, hard surface cleaning and/or treatment, and other cleaning for consumer or institutional use; products and/or methods relating to bath tissue, facial tissue, paper handkerchiefs, and/or paper towels; tampons, feminine napkins; products and/or methods relating to oral care including toothpastes, tooth gels, tooth rinses, denture adhesives, tooth whitening; over-the-counter health care including cough and cold remedies, pain relievers, RX pharmaceuticals, pet health and nutrition, and water purification; processed food products intended primarily for consumption between customary meals or as a meal accompaniment (non-limiting examples include potato chips, tortilla chips, popcorn, pretzels, corn chips, cereal bars, vegetable chips or crisps, snack mixes, party mixes, multigrain chips, snack crackers, cheese snacks, pork rinds, corn snacks, pellet snacks, extruded snacks and bagel chips); and coffee.

As used herein, the term "cleaning composition" includes, unless otherwise indicated, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, dentifrice, car or carpet shampoos, bathroom cleaners; hair shampoos and hair-rinses; shower gels and foam baths and metal cleaners; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists.

As used herein, the term "fabric care composition" includes, unless otherwise indicated, fabric softening compositions, fabric enhancing compositions, fabric freshening compositions and combinations thereof.

As used herein, the phrase "benefit agent containing delivery particle" encompasses microcapsules including perfume microcapsules.

As used herein, the terms "particle", "benefit agent containing delivery particle", "capsule" and "microcapsule" are synonymous.

As used herein, reference to the term "(meth)acrylate" or "(meth)acrylic" is to be understood as referring to both the acrylate and the methacrylate versions of the specified monomer, oligomer and/or prepolymer, (for example "allyl (meth)acrylate" indicates that both allyl methacrylate and allyl acrylate are possible, similarly reference to alkyl esters of (meth)acrylic acid indicates that both alkyl esters of acrylic acid and alkyl esters of methacrylic acid are possible, similarly poly(meth)acrylate indicates that both polyacrylate and polymethacrylate are possible). Poly(meth)acrylate materials are intended to encompass a broad spectrum of polymeric materials including, for example, polyester poly(meth)acrylates, urethane and polyurethane poly(meth)acrylates (especially those prepared by the reaction of an hydroxyalkyl (meth)acrylate with a polyisocyanate or a urethane polyisocyanate), methylcyanoacrylate, ethylcyanoacrylate, diethyleneglycol di(meth)acrylate, trimethylolpropane tri(meth)acrylate, ethylene glycol di(meth)acrylate, allyl (meth)acrylate, glycidyl (meth)acrylate, (meth)acrylate functional silicones, di-, tri- and tetraethylene glycol di(meth)acrylate, dipropylene glycol di(meth)acrylate, polyethylene glycol di(meth)acrylate, di(pentamethylene glycol) di(meth)acrylate, ethylene di(meth)acrylate, neopentyl glycol di(meth)acrylate, trimethylol propane tri(meth)acrylate, ethoxylated bisphenol A di(meth)acrylates, bisphenol A di(meth)acrylates, diglycerol di(meth)acrylate, tetraethylene glycol dichloroacrylate, 1,3-butanediol di(meth)acrylate, neopentyl di(meth)acrylate, trimethylolpropane tri(meth)acrylate, polyethylene glycol di(meth)acrylate and dipropylene glycol di(meth)acrylate and various multifunctional (meth)acrylates. Monofunctional acrylates, i.e., those containing only one acrylate group, may also be advantageously used. Typical monoacrylates include 2-ethylhexyl (meth)acrylate, 2-hydroxyethyl (meth)acrylate, cyanoethyl (meth)acrylate, 2-hydroxypropyl (meth)acrylate, p-dimethylaminoethyl (meth)acrylate, lauryl (meth)acrylate, cyclohexyl (meth)acrylate, tetrahydrofurfuryl (meth)acrylate, chlorobenzyl (meth)acrylate, aminoalkyl(meth)acrylate, various alkyl(meth)acrylates and glycidyl (meth)acrylate. Of course mixtures of (meth)acrylates or their derivatives as well as combinations of one or more (meth)acrylate monomers, oligomers and/or prepolymers or their derivatives with other copolymerizable monomers, including acrylonitriles and methacrylonitriles may be used as well.

As used herein, the articles including "a" and "an" when used in a claim, are understood to mean one or more of what is claimed or described.

As used herein, the terms "include", "includes" and "including" are meant to be non-limiting.

As used herein, styrene maleic anhydride copolymer is synonymous with Poly(Styrene-Co-maleic anhydride).

A non-consumer product means products other than products defined herein as consumer products. As used herein, "products other than consumer products" means slurries of capsules, typically aqueous slurries of capsules used in industry in the manufacture of various products. The slurry of itself is not a consumer product, but can be used in industry in the manufacture of various products including use in the commercial manufacture of consumer and non-consumer products. Illustrative but non-limiting examples of products other than consumer products, include industrial products such as aqueous slurries of microcapsules used in the manufacture of record materials including carbonless paper; slurries of microcapsules used in the manufacture of, or as components of, or as coatings for, or treatments of, various construction materials such as wallboard, gypsum board, dry wall, fiberboard, plasterboard; treatments or coatings in textile manufacture, treatments of construction surfaces, paint additives, mineral composites or coatings or additives; injection well lubricants or treatments; cement additives; additives to composites; coatings for paper, paperboard, film, and surfaces of various industrial products. Microcapsules of the present invention comprise a core that comprises a material such as perfume and/or a silicone. Other materials useful in the core in addition, or in substitution of one or both of the perfume or silicone, can include benefit agents such as attractants, repellants, odiferous repellants, water repellants, adhesives, static dissipaters, lubricants, flame retardants, solvents, reaction enhancers, activators, catalysts, rust inhibitors, fragrances, essential oils, essences, indicators, security taggents, dyes, chromogens, uv blockers, electromagnetic absorbers or reflectors, infrared absorbers, drying materials, flavors, emulsifiers, rheology modifiers, pharmaceutical agents, coagulants, biologicals such as yeast, amino acids, peptides, dna sequences or fragments, and biological control agents including biocides, insecticides, mildewcides, pesticides, and the like. The objective of treatment using the slurry of microcapsules in industry is generally to leave deposited on the surfaces of substrates enough benefit agent so that there is a residual benefit imparted to a substrate surface after treatment of the substrate is completed or when the industrial slurry of capsules is incorporated into the finished commercial product.

The test methods disclosed in the Test Methods Section of the present application should be used to determine the respective values of the parameters of Applicants' inventions.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Particles

In one aspect, benefit agent delivery particles comprise a core and a shell, said shell encapsulating said core, said shell comprising:

a) styrene maleic anhydride monomethylmaleate, and/or a salt thereof, in one aspect, styrene maleic anhydride monomethylmaleate di-sodium salt and/or styrene maleic anhydride monomethylmaleate ammonia-salt; in one aspect, said styrene maleic anhydride monomethylmaleate, and/or a salt thereof has one, two three or four of the following properties:
  (i) a molar ratio of styrene to maleic anhydride of from about 9:1 to about 1:9, from about 6:4 to about 4:6 or about 1:1;
  (ii) a weight average molecular weight of from about 1,000 Da to about 100,000,000 Da or from about 50,000 Da to about 500,000 Da;
  (iii) a density of from about 1.03 g/cm$^3$ to about 1.11 g/cm$^3$;
  (iv) a hydrolysis degree of from about 20% to about 95%, preferably from about 25% to about 80%, more preferably from about 30% to about 70%, most preferably from about 40% to about 60%;

b) and optionally:
  (i) an aminoplast polymer, in one aspect, said aminoplast polymer comprises a material selected from the group consisting of a reaction product of melamine and formaldehyde, a reaction product of urea and formaldehyde and mixtures thereof, in one aspect, a material selected from the group consisting of methylol melamine, methylated methylol melamine, dimethylol urea, methylated dimethylol urea and mixtures thereof
  (ii) a material selected from the group consisting of a polyacrylate, a polyethylene glycol acrylate, a polyurethane acrylate, an epoxy acrylate, a polymethacrylate, a polyethylene glycol methacrylate, a polyurethane methacrylate, an epoxy methacrylate and mixtures thereof, in one aspect, said polyacrylate is a reaction product of:
    an oil soluble or dispersible amine, in one aspect, said amine is a secondary or tertiary amine, in one aspect, said amine is an amine oligomer, in one aspect, said amine is an aminoalkyl acrylate or aminoalkyl methacrylate, in one aspect, said amine is selected from diethylaminoethyl methacrylate, dimethylaminoethyl methacrylate, or tertiary butyl aminoethyl methacrylate;
    with a multifunctional acrylate or methacrylate monomer or oligomer; in one aspect, said multifunctional acrylate or methacrylate monomer or oligomer is selected from the group consisting of aliphatic or aromatic urethane diacrylate, aliphatic or aromatic urethane triacrylate, aliphatic or aromatic urethane tetracrylate, aliphatic or aromatic urethane hexacrylate, pentaerythritol diacrylate, pentaerythritol triacrylate, pentaerythritol tetracrylate, dipentaerythritol pentaacrylate, ethoxylated pentaerythritol tetraacrylate and mixtures thereof, in one aspect, said multifunctional acrylate or methacrylate monomer or oligomer is selected from the group consisting of allyl methacrylate, triethylene glycol dimethacrylate, epoxy acrylate, epoxymethacrylates and mixtures thereof; and
    an oil soluble acid, in one aspect, said oil soluble acid is selected from the group consisting of carboxy acids comprising one or more a monoalkyl maleate moieties, organic sulfonic acid, and mixtures thereof in one aspect, said carboxy acids comprising one or more a monoalkyl maleate moieties, in one aspect, Beta-carboxyethyl acrylate, in one aspect, said organic sulfonic acid is selected from the group consisting of alkyl benzene sulfonic acid, dodecyl diphenyl oxidedisulfonic acid, branched C$_{12}$ diphenyl oxide disulfonic acid, 4-hydrizino benzene sulfonic acid acrylic acid and mixtures thereof;
  (iii) a reaction product of one or more aromatic alcohols and one or materials comprising at least one aldehyde moiety in one aspect said aromatic alcohols may be phenols that comprise two or more hydroxyl groups, in one aspect, said aromatic alcohols are selected from the group consisting of brenzcatechin (pyrocatechol), resorcinol, hydroquinone, 1,4 naphthohydroxyquinone, phloroglucinol, pyrrogallol, hydroxyhydroquinone and mixtures thereof. In one aspect, said material
    comprising one or more aldehyde moieties comprise two, three, or four free aldehyde moieties per molecule, in one aspect, said material comprising one or more aldehyde moieties is selected from the group consisting of glyoxal, gluteraldehyde, succindialdehyde; and/or
  (iv) the reaction product of melamine or a methylenediamine which has the structure $CH_2(NH_2)_2$, a material comprising one or more aldehyde moieties, an alkoxy ethanol and an acid, in one aspect, said material comprising one or more aldehyde moieties is selected from the group consisting of glyoxal, a C(4,6)-2,2-dialkoxy-ethanal, in one aspect, 2,2-dimethoxy-ethanal, or 2,2-diethoxy-ethanal, a glyoxalate and mixtures thereof c) optionally, a colloid,
  (i) in one aspect, when said benefit agent delivery particle's shell comprises a reaction product of one or more of melamine and formaldehyde, methylol melamine, methylated methylol melamine, urea and formaldehyde, dimethylol urea, or methylated dimethylol urea said colloid is selected from alkyl acrylate acrylic acid copolymer and mixtures thereof, in one aspect said colloid is selected from alkyl acrylate acrylic acid copolymers wherein the alkyl acrylate is selected from methyl acrylate, ethyl acrylate, propyl acrylate, butyl acrylate, hexyl acrylate, cyclohexyl acrylate, ethyl hexyl acrylate and mixtures thereof;
  (ii) in one aspect, when said benefit agent delivery particle's shell comprises one or more of poly(meth)acrylate or alkyl esters of (meth)acrylic acid said colloid is selected from alkyl acrylate acrylic acid copolymer and mixtures thereof, in one aspect said colloid is selected from alkyl acrylate acrylic acid copolymers wherein the alkyl acrylate is selected from methyl acrylate, ethyl acrylate, propyl acrylate, butyl acrylate, pentyl acrylate, hexyl acrylate, cyclohexyl acrylate, ethyl hexyl acrylate and mixtures thereof;
  (iii) in one aspect, when said benefit agent delivery particle's shell comprises a reaction product of one or more aromatic alcohols and one or materials comprising at least one aldehyde moiety, said colloid is selected from alkyl acrylate acrylic acid copolymer and mixtures thereof, in one aspect, said colloid is selected from alkyl acrylate acrylic acid copolymers wherein the alkyl acrylate is selected from methyl acrylate, ethyl acrylate, propyl acrylate, butyl acrylate, hexyl acrylate, cyclohexyl acrylate, ethyl hexyl acrylate and mixtures thereof;
  (iv) in one aspect, when said benefit agent delivery particle's shell comprises a reaction product of melamine or a methylenediamine $CH_2(NH_2)_2$, a material comprising one or more aldehyde moieties, an alkoxy ethanol and an acid, in one aspect, said colloid is selected from alkyl acrylate acrylic acid copolymer and mixtures thereof, in one aspect said colloid is selected from alkyl acrylate acrylic acid copolymers wherein the alkyl acrylate is selected from methyl acrylate, ethyl acrylate, propyl acrylate, butyl acrylate, hexyl acrylate, cyclohexyl acrylate, ethyl hexyl acrylate and mixtures thereof; and d) optionally, an emulsifier, in one aspect, said emulsifier is selected from cationic emulsifiers of amine polymers with primary, secondary or tertiary functionality or nonionic emulsifiers having a hydroxyl, ether, ester, ketone, or amide functionality.

In one aspect, said benefit agent delivery particles' styrene maleic anhydride monomethylmaleate component has a hydrolysis degree of from about 20% to about 95%, preferably from about 25% to about 80%, more preferably from about 30% to about 70%, most preferably from about 40% to about 60%.

In one aspect, benefit agent delivery particles comprise=a core and a shell, said shell encapsulating said core, said shell comprising:

a) styrene maleic anhydride monomethylmaleate, and/or a salt thereof, in one aspect, styrene maleic anhydride monomethylmaleate di-sodium salt and/or styrene maleic anhydride monomethylmaleate ammonia-salt; in one aspect, said styrene maleic anhydride monomethylmaleate, and/or a salt thereof has one, two, three of the following properties:
  (i) a molar ratio of styrene to maleic anhydride of from about 9:1 to about 1:9, from about 6:4 to about 4:6 or about 1:1;
  (ii) a weight average molecular weight of from about 1,000 Da to about 100,000,000 Da or from about 50,000 Da to about 500,000 Da;
  (iii) a density of from about 1.03 $g/cm^3$ to about 1.11 $g/cm^3$;

b) and optionally:
  (i) an aminoplast polymer, in one aspect, said aminoplast polymer comprises a material selected from the group consisting of a reaction product of melamine and formaldehyde, a reaction product of urea and formaldehyde and mixtures thereof, in one aspect, a material selected from the group consisting of methylol melamine, methylated methylol melamine, dimethylol urea, methylated dimethylol urea and mixtures thereof
  (ii) a material selected from the group consisting of a polyacrylate, a polyethylene glycol acrylate, a polyurethane acrylate, an epoxy acrylate, a polymethacrylate, a polyethylene glycol methacrylate, a polyurethane methacrylate, an epoxy methacrylate and mixtures thereof, in one aspect, said polyacrylate is a reaction product of:
    an oil soluble or dispersible amine, in one aspect, said amine is a secondary or tertiary amine, in one aspect, said amine is an amine oligomer, in one aspect, said amine is an aminoalkyl acrylate or aminoalkyl methacrylate, in one aspect, said amine is selected from diethylaminoethyl methacrylate, dimethylaminoethyl methacrylate, or tertiary butyl aminoethyl methacrylate;
    with a multifunctional acrylate or methacrylate monomer or oligomer; in one aspect, said multifunctional acrylate or methacrylate monomer or oligomer is selected from the group consisting of aliphatic or aromatic urethane diacrylate, aliphatic or aromatic urethane triacrylate, aliphatic or aromatic urethane tetracrylate, aliphatic or aromatic urethane hexacrylate, pentaerythritol diacrylate, pentaerythritol triacrylate, pentaerythritol tetracrylate, dipentaerythritol pentaacrylate, ethoxylated pentaerythritol tetraacrylate and mixtures thereof, in one aspect, said multifunctional acrylate or methacrylate monomer or oligomer is selected from the group consisting of allyl methacrylate, triethylene glycol dimethacrylate, epoxy acrylate, epoxymethacrylates and mixtures thereof; and
    an oil soluble acid, in one aspect, said oil soluble acid is selected from the group consisting of carboxy acids comprising one or more a monoalkyl maleate moieties, organic sulfonic acid, and mixtures thereof in one aspect, said carboxy acids comprising one or more a monoalkyl maleate moieties, in one aspect, Beta-carboxyethyl acrylate, in one aspect, said organic sulfonic acid is selected from the group consisting of alkyl benzene sulfonic acid, dodecyl diphenyl oxidedisulfonic acid, branched $C_{12}$ diphenyl oxide disulfonic acid, 4-hydrizino benzene sulfonic acid acrylic acid and mixtures thereof;
  (iii) a reaction product of one or more aromatic alcohols and one or materials comprising at least one aldehyde moiety in one aspect said aromatic alcohols may be phenols that comprise two or more hydroxyl groups, in one aspect, said aromatic alcohols are selected from the group consisting of brenzcatechin (pyrocatechol), resorcinol, hydroquinone, 1,4 naphthohydroxyquinone, phloroglucinol, pyrrogallol, hydroxyhydroquinone and mixtures thereof. In one aspect, said material comprising one or more aldehyde moieties comprise two, three, or four free aldehyde moieties per molecule, in one aspect, said material comprising one or more aldehyde moieties is selected from the group consisting of glyoxal, gluteraldehyde, succindialdehyde; and/or
  (iv) the reaction product of melamine or a methylenediamine which has the structure $CH_2(NH_2)_2$, a material comprising one or more aldehyde moieties, an alkoxy ethanol and an acid, in one aspect, said material comprising one or more aldehyde moieties is selected from the group consisting of glyoxal, a C(4,6)-2,2-dialkoxy-ethanal, in one aspect, 2,2-dimethoxy-ethanal, or 2,2-diethoxy-ethanal, a glyoxalate and mixtures thereof c) optionally, a colloid,
  (i) in one aspect, when said benefit agent delivery particle's shell comprises a reaction product of one or more of melamine and formaldehyde, methylol melamine, methylated methylol melamine, urea and formaldehyde, dimethylol urea, or methylated dimethylol urea said colloid is selected from alkyl acrylate acrylic acid copolymer and mixtures thereof, in one aspect said colloid is selected from alkyl acrylate acrylic acid copolymers wherein the alkyl acrylate is selected from methyl acrylate, ethyl acrylate, propyl acrylate, butyl acrylate, hexyl acrylate, cyclohexyl acrylate, ethyl hexyl acrylate and mixtures thereof;
  (ii) in one aspect, when said benefit agent delivery particle's shell comprises one or more of poly(meth) acrylate or alkyl esters of (meth)acrylic acid said colloid is selected from alkyl acrylate acrylic acid copolymer and mixtures thereof, in one aspect said colloid is selected from alkyl acrylate acrylic acid copolymers wherein the alkyl acrylate is selected from methyl acrylate, ethyl acrylate, propyl acrylate, butyl acrylate, pentyl acrylate, hexyl acrylate, cyclohexyl acrylate, ethyl hexyl acrylate and mixtures thereof;

(iii) in one aspect, when said benefit agent delivery particle's shell comprises a reaction product of one or more aromatic alcohols and one or materials comprising at least one aldehyde moiety, said colloid is selected from alkyl acrylate acrylic acid copolymer and mixtures thereof, in one aspect, said colloid is selected from alkyl acrylate acrylic acid copolymers wherein the alkyl acrylate is selected from methyl acrylate, ethyl acrylate, propyl acrylate, butyl acrylate, hexyl acrylate, cyclohexyl acrylate, ethyl hexyl acrylate and mixtures thereof;

(iv) in one aspect, when said benefit agent delivery particle's shell comprises a reaction product of melamine or a methylenediamine $CH_2(NH_2)_2$, a material comprising one or more aldehyde moieties, an alkoxy ethanol and an acid, in one aspect, said colloid is selected from alkyl acrylate acrylic acid copolymer and mixtures thereof, in one aspect said colloid is selected from alkyl acrylate acrylic acid copolymers wherein the alkyl acrylate is selected from methyl acrylate, ethyl acrylate, propyl acrylate, butyl acrylate, hexyl acrylate, cyclohexyl acrylate, ethyl hexyl acrylate and mixtures thereof; and d) optionally, an emulsifier, in one aspect, said emulsifier is selected from cationic emulsifiers of amine polymers with primary, secondary or tertiary functionality or nonionic emulsifiers having a hydroxyl, ether, ester, ketone, or amide functionality.

In one aspect, said benefit agent delivery particles comprise:

a) a core material comprising a material selected from the group consisting of perfume, suds suppressor or mixtures thereof;

b) a shell that encapsulates said core material, said shell comprising a material selected from the group consisting of an aminoplast polymer, a polyacrylate or mixtures thereof; and based on total benefit agent particle shell weight, from about 1% to about 80%, from about 30% to about 75% or from about 50% to about 70% of a styrene maleic anhydride monomethylmaleate, and/or a salt thereof; and c) a colloid based on total benefit agent particle shell weight, from about 1% to 27%, from about 3% to about 24%, from about 6% to about 22% of colloid materials selected from Colloid 121 or polyacrylic acid.

In one embodiment the above-described benefit agent delivery particles have a mean particle size of from about 1 micrometers to about 100 micrometers, from about 5 micrometers to about 80 micrometers or 8 micrometers to about 50 micrometers at least 75% of said benefit agent delivery particles having a fracture strength of from about 0.2 MPa to about 10 MPa; and said particles having a benefit agent leakage of from 0% to about 30%.

In a further embodiment the benefit agent delivery particles, has a mean particle size of from about 1 micrometers to about 100 micrometers, from about 5 micrometers to about 80 micrometers or 8 micrometers to about 50 micrometers at least 75% of said benefit agent delivery particles having a benefit agent leakage of from 0% to about 30%.

In a further embodiment, the above-described benefit agent delivery particles, at least 75% of said benefit agent delivery particles have a particle size of from about 1 micrometers to about 80 micrometers.

In a yet further embodiment of the above-described benefit agent delivery particles, at least 75% of said benefit agent delivery particles have a particle wall thickness of from about 10 nm to about 250 nm, from about 20 nm to about 200 nm, or from 25 nm to about 180 nm.

In a yet further embodiment the above-described benefit agent delivery particles have a shell which comprises an aminoplast polymer, in one aspect, said shell comprises from about 50% to about 100%, from about 70% to about 100% or even from about 80% to about 100% of said aminoplast polymer.

In one aspect, the above-described benefit agent delivery particles have a shell wherein said shell comprises an aminoplast polymer comprising a material selected from the group consisting of a resin of melamine and formaldehyde, a mixed resin of urea-formaldehyde, maleic anhydride copolymers, a melamine resin and mixtures thereof.

In one aspect, the above-described benefit agent delivery particles have a shell wherein said shell comprises a polyacrylate in one aspect, said shell comprises from about 50% to about 100%, from about 70% to about 100% or even from about 80% to about 100% of said polyacrylate polymer, in one aspect said polyacrylate comprises a polyacrylate cross polymer.

In a further aspect, the aforementioned benefit agent delivery particles have a shell wherein said shell comprises a polyacrylate that comprises a material selected from the group consisting of an amine acrylate, methacrylate monomer, a carboxylic acid acrylate, carboxylic acid methacrylate monomer and mixtures thereof.

In a further embodiment, the above-described benefit agent delivery particles comprise a deposition aid, and in a further aspect the benefit agent delivery partial deposition aid coats the outer surface of said shell.

In a further embodiment, the above-described benefit agent delivery particles comprise a deposition aid and said deposition aid comprises a material selected from the group consisting of poly(meth)acrylate, poly(ethylene-maleic anhydride), polyamine, wax, polyvinylpyrrolidone, polyvinylpyrrolidone co-polymers, polyvinylpyrrolidone-ethyl acrylate, polyvinylpyrrolidone-vinyl acrylate, polyvinylpyrrolidone methylacrylate, polyvinylpyrrolidone-vinyl acetate, polyvinyl acetal, polyvinyl butyral, polysiloxane, poly(propylene maleic anhydride), maleic anhydride derivatives, co-polymers of maleic anhydride derivatives, polyvinyl alcohol, styrene-butadiene latex, gelatin, gum Arabic, carboxymethyl cellulose, carboxymethyl hydroxyethyl cellulose, hydroxyethyl cellulose, other modified celluloses, sodium alginate, chitosan, casein, pectin, modified starch, polyvinyl acetal, polyvinyl butyral, polyvinyl methyl ether/maleic anhydride, polyvinyl pyrrolidone and its co polymers, poly(vinyl pyrrolidone/methacrylamidopropyl trimethyl ammonium chloride), polyvinylpyrrolidone/vinyl acetate, polyvinyl pyrrolidone/dimethylaminoethyl methacrylate, polyvinyl amines, polyvinyl formamides, polyallyl amines and copolymers of polyvinyl amines, polyvinyl formamides, and polyallyl amines and mixtures thereof.

In a further aspect, said benefit agent delivery particles comprise a deposition aid and said deposition aid comprises a material selected from the group consisting of poly(meth) acrylates, poly(ethylene-maleic anhydride), polyamine, polyvinylpyrrolidone, polyvinylpyrrolidone-ethyl acrylate, polyvinylpyrrolidone-vinyl acrylate, polyvinylpyrrolidone methylacrylate, polyvinylpyrrolidone-vinyl acetate, polyvinyl acetal, polyvinyl butyral, polysiloxane, poly(propylene maleic anhydride), maleic anhydride derivatives, co-polymers of maleic anhydride derivatives, polyvinyl alcohol, carboxymethyl cellulose, carboxymethyl hydroxyethyl cellulose, hydroxyethyl cellulose, polyvinyl methyl ether/maleic anhydride, poly(vinyl pyrrolidone/methacrylamidopropyl trimethyl ammonium chloride), polyvinylpyrrolidone/vinyl acetate, polyvinyl pyrrolidone/dimethylaminoethyl methacrylate, polyvinyl amines, polyvinyl formamides, polyallyl amines and copolymers of polyvinyl amines, polyvinyl formamides, and polyallyl amines and mixtures thereof.

In a yet further aspect, the aforementioned benefit agent delivery particles comprise a deposition aid wherein said deposition aid comprises a material selected from the group consisting of poly(meth)acrylates, poly(ethylene-maleic anhydride), polyamine, polyvinylpyrrolidone, polyvinylpyrrolidone-ethyl acrylate, polyvinylpyrrolidone-vinyl acrylate, polyvinylpyrrolidone methylacrylate, polyvinylpyrrolidone-vinyl acetate, polyvinyl acetal, polysiloxane, poly(propylene maleic anhydride), maleic anhydride derivatives, co-polymers of maleic anhydride derivatives, polyvinyl alcohol, carboxymethyl cellulose, carboxymethyl hydroxyethyl cellulose, hydroxyethyl cellulose, polyvinyl methyl ether/maleic anhydride, polyvinylpyrrolidone/vinyl acetate, polyvinyl pyrrolidone/dimethylaminoethyl methacrylate, polyvinyl amines, polyvinyl formamides, polyallyl amines and copolymers of polyvinyl amines, polyvinyl formamides, and polyallyl amines and mixtures thereof.

In a yet further embodiment, the above-described benefit agent delivery particles have a core wherein said benefit agent delivery particles' core material comprises a suds suppressor material selected from the group consisting of silicone oils, silicone resins, silicone polymers, silica and mixtures thereof.

In one aspect, the benefit agent delivery particles have a core wherein said benefit agent delivery particles' core material comprises, based on total benefit agent delivery particle weight, at least about 20 wt %, from about 20% to about 99%, from about 70% to about 98%, from about 85% to about 96% benefit agent.

In one aspect the benefit agent delivery particles have a core wherein said benefit agent delivery particles' core material comprises:
a) a perfume composition having a C log P of less than 4.5;
b) a perfume composition comprising, based on total perfume composition weight, 60% perfume materials having a C log P of less than 4.0;
c) a perfume composition comprising, based on total perfume composition weight, 35% perfume materials having a C log P of less than 3.5;
d) a perfume composition comprising, based on total perfume composition weight, 40% perfume materials having a C log P of less than 4.0 and at least 1% perfume materials having a C log P of less than 2.0;
e) a perfume composition comprising, based on total perfume composition weight, 40% perfume materials having a C log P of less than 4.0 and at least 15% perfume materials having a C log P of less than 3.0;
f) a perfume composition comprising, based on total perfume composition weight, at least 1% butanoate esters and at least 1% of pentanoate esters;
g) a perfume composition comprising, based on total perfume composition weight, at least 2% of an ester comprising an allyl moiety and at least 10% of another perfume comprising an ester moiety;
h) a perfume composition comprising, based on total perfume composition weight, at least 1% of an aldehyde comprising an alkyl chain moiety;
i) a perfume composition comprising, based on total perfume composition weight, at least 2% of a butanoate ester;
j) a perfume composition comprising, based on total perfume composition weight, at least 1% of a pentanoate ester;
k) a perfume composition comprising, based on total perfume composition weight, at least 3% of an ester comprising an allyl moiety and 1% of an aldehyde comprising an alkyl chain moiety;
l) a perfume composition comprising, based on total perfume composition weight, at least 25% of a perfume comprising an ester moiety and 1% of an aldehyde comprising an alkyl chain moiety;
m) a perfume compositions comprising, based on total perfume composition weight, at least 2% of a material selected from 4-(2,6,6-trimethyl-1-cyclohexenyl)-3-buten-2-one, 4-(2,6,6-trimethyl-2-cyclohexenyl)-3-buten-2-one and 3-buten-2-one,3-methyl-4-(2,6,6-trimethyl-1-cyclohexen-2-yl)- and mixtures thereof;
n) a perfume composition comprising, based on total perfume composition weight, at least 0.1% of tridec-2-enonitrile, and mandaril, and mixtures thereof;
o) a perfume composition comprising, based on total perfume composition weight, at least 2% of a material selected from 3,7-dimethyl-6-octene nitrile, 2-cyclohexylidene-2-phenylacetonitrile and mixtures thereof;
p) a perfume composition comprising, based on total perfume composition weight, at least 80% of one or more perfumes comprising a moiety selected from the group consisting of esters, aldehydes, ionones, nitriles, ketones and combinations thereof;
q) a perfume composition comprising, based on total perfume composition weight, at least 3% of an ester comprising an allyl moiety; a perfume composition comprising, based on total perfume composition weight, at least 20% of a material selected from the group consisting of: 1-methylethyl-2-methylbutanoate; ethyl-2-methyl pentanoate; 1,5-dimethyl-1-ethenyl-hexyl-4-enyl acetate; p-meth-1-en-8-yl acetate; 4-(2,6,6-rimethyl-2-cyclohexenyl)-3-buten-2-one; 4-acetoxy-3-methoxy-1-propenylbenzene; 2-propenyl cyclohexanepropionate; bicyclo[2.2.1]hept-5-ene-2-carboxylic acid,3-(1-methylethyl)-ethyl ester; bycyclo [2.2.1]heptan-2-ol, 1,7,7-trimethyl-, acetate; 1,5-dimethyl-1-ethenylhex-4-enylacetate; hexyl 2-methyl propanoate; ethyl-2-methylbutanoate; 4-undecanone; 5-heptyldihydro-2(3h)-furanone; 1,6-nonadien-3-ol,3,7dimethyl-; 3,7-dimethylocta-1,6-dien-3-o; 3-cyclohexene-1-carboxaldehyde,dimethyl-; 3,7-dimethyl-6-octene nitrile; 4-(2,6,6-trimethyl-1-cyclohexenyl)-3-buten-2-one; tridec-2-enonitrile; patchouli oil; ethyl tricycle [5.2.1.0]decan-2-carboxylate; 2,2-dimethyl-cyclohexanepropanol; hexyl ethanoate, 7-acetyl,1,2,3,4, 5,6,7,8-octahydro-1,1,6,7-tetramethyl naphtalene; allyl-cyclohexyloxy acetate; methyl nonyl acetic aldehyde; 1-spiro[4,5]dec-7-en-7-yl-4-pentenen-1-one; 7-octen-2-ol,2-methyl-6-methylene-,dihydro; cyclohexanol,2-(1,1-dimethylethyl)-, acetate; hexahydro-4,7-methanoinden-5(6)-yl propionatehexahydro-4,7-methanoinden-5(6)-yl propionate; 2-methoxynaphtalene; 1-(2,6,6-trimethyl-3-cyclohexenyl)-2-buten-1-one; 1-(2,6,6-trimethyl-2-cyclohexenyl)-2-buten-1-one; 3,7-dimethyloctan-3-ol; 3-buten-2-one,3-methyl-4-(2,6,6-trimethyl-1-cyclohexen-2-yl)-; hexanoic acid, 2-propenyl ester; (z)-non-6-en-1-al; 1-decyl aldehyde; 1-octanal; 4-t-butyl-α-methylhydrocinnamaldehyde; alpha-hexylcinnamaldehyde; ethyl-2,4-hexadienoate; 2-propenyl 3-cyclohexanepropanoate; and mixtures thereof;

r) a perfume composition comprising, based on total perfume composition weight, at least 20% of a material selected from the group consisting of: 1-methylethyl-2-methylbutanoate; ethyl-2-methyl pentanoate; 1,5-dimethyl-1-ethenylhex-4-enyl acetate; p-menth-1-en-8-yl acetate; 4-(2,6,6-trimethyl-2-cyclohexenyl)-3-buten-2-one; 4-acetoxy-3-methoxy-1-propenylbenzene; 2-propenyl cyclohexanepropionate; bicyclo[2.2.1]hept-5-ene-2-carboxylic acid,3-(1-methylethyl)-ethyl ester; bycyclo[2.2.1]heptan-2-ol, 1,7,7-trimethyl-, acetate; 1,5-dimethyl-1-ethenylhex-4-enyl acetate; hexyl 2-methyl propanoate; ethyl-2-methylbutanoate,4-undecanolide; 5-heptyldihydro-2(3h)-furanone; 5-hydroxydodecanoic acid; decalactones; undecalactones, 1,6-nonadien-3-ol,3,7dimethyl-; 3,7-dimethylocta-1,6-dien-3-ol; 3-cyclohexene-1-carboxaldehyde,dimethyl-; 3,7-dimethyl-6-octene nitrile; 4-(2,6,6-trimethyl-1-cyclohexenyl)-3-buten-2-one; tridec-2-enonitrile; patchouli oil; ethyl tricycle [5.2.1.0]decan-2-carboxylate; 2,2-dimethyl-cyclohexanepropanol; allyl-cyclohexyloxy acetate; methyl nonyl acetic aldehyde; 1-spiro[4,5]dec-7-en-7-yl-4-pentenen-1-one; 7-octen-2-ol,2-methyl-6-methylene-,dihydro, cyclohexanol,2-(1,1-dimethylethyl)-, acetate; hexahydro-4,7-methanoinden-5(6)-yl propionatehexahydro-4,7-methanoinden-5(6)-yl propionate; 2-methoxynaphtalene; 1-(2,6,6-trimethyl-3-cyclohexenyl)-2-buten-1-one; 1-(2,6,6-trimethyl-2-cyclohexenyl)-2-buten-1-one; 3,7-dimethyloctan-3-ol; 3-buten-2-one,3-methyl-4-(2,6,6-trimethyl-1-cyclohexen-2-yl)-; hexanoic acid, 2-propenyl ester; (z)-non-6-en-1-al; 1-decyl aldehyde; 1-octanal; 4-t-butyl-α-methylhydrocinnamaldehyde; ethyl-2,4-hexadienoate; 2-propenyl 3-cyclohexanepropanoate; and mixtures thereof;

s) a perfume composition comprising, based on total perfume composition weight, at least 5% of a material selected from the group consisting of 3-cyclohexene-1-carboxaldehyde,dimethyl-; 3-buten-2-one,3-methyl-4-(2,6,6-trimethyl-1-cyclohexen-2-yl)-; patchouli oil; Hexanoic acid, 2-propenyl ester; 1-Octanal; 1 decyl aldehyde; (z)-non-6-en-1-al; methyl nonyl acetic aldehyde; ethyl-2-methylbutanoate; 1-methylethyl-2-methylbutanoate; ethyl-2-methyl pentanoate; 4-hydroxy-3-ethoxybenzaldehyde; 4-hydroxy-3-methoxybenzaldehyde; 3-hydroxy-2-methyl-4-pyrone; 3-hydroxy-2-ethyl-4-pyrone and mixtures thereof;

t) a perfume composition comprising, based on total perfume composition weight, less than 10% perfumes having a C log P greater than 5.0;

u) a perfume composition comprising geranyl palmitate; or v) a perfume composition comprising a first and an optional second material, said first material having:
(i) a C log P of at least 2;
(ii) a boiling point of less than about 280° C.; and second optional second material, when present, having
(i) a C log P of less than 2.5.

In one aspect, the aforementioned benefit agent delivery particles comprise a material selected from the group consisting of a formaldehyde scavenger, a structurant, an anti-agglomeration agent and mixtures thereof.

In a further aspect, the above-described benefit agent delivery particles of Claim 2, comprising less than 150 ppm, less than 100 ppm, less than 50 ppm, less than 10 ppm, less than 5 ppm or even less than 1 ppm formaldehyde.

In a yet further aspect, the benefit agent delivery particles have a viscosity of from 1 to 1500 centipoises (1-1500 mPa*s), from 100 to 1000 centipoises (100-1000 mPa*s), or from 200 to 500 centipoises (200-500 mPa*s) at 20 s$^{-1}$ and 21° C.

In a yet further embodiment, benefit agent delivery particle is produced by the process of:
a) preparing a first solution comprising, a non-esterified styrene maleic-anhydride copolymer emulsifier and a first resin, in one aspect, based on total solution weight, from about 20% to about 100% of a non-esterified styrene maleic-anhydride copolymer emulsifier and a first resin, the ratio of said styrene-maleic anhydride copolymer and said first resin being from about 0.1:1 to about 10:1;
b) preparing a second solution comprising based on total solution weight from about 20% to about 95% water, a second emulsifier and a second resin, the ratio of said second emulsifier and said second resin being from about 0:1 to about 3:1;
c) combining a core material and said first solution to form a first composition;
d) emulsifying said first composition;
e) combining said first composition and said second solution to form a second composition and optionally combining any processing aids and said second composition;
f) mixing said second composition for at least 15 minutes at a temperature of from about 20° C. to about 100° C. or 20° C. to about 95° C. and optionally combining any processing aids to said second composition;
g) optionally combining any scavenger material, structurant, and/or anti-agglomeration agent with said second composition during step f) or thereafter; and
h) optionally spray drying said second composition.

In a yet further embodiment in the above-described process of producing a benefit agent delivery particle, said non-esterified styrene maleic-anhydride copolymer comprises styrene maleic anhydride monomethylmaleate, sodium salt.

In a further embodiment, in the above-described process of producing benefit agent delivery particles to said resin material comprises a reaction product of an aldehyde, with an amine, in one aspect, said amine is selected from the group consisting of melamine, urea, benzoguanamine, glycoluril, and mixtures thereof.

In one aspect, a benefit agent delivery particle is produced by the process of:
a) preparing a first solution comprising, based on total solution weight from about 60% to 100% of a non-esterified styrene maleic anhydride emulsifier,
b) combining a core material which includes monomeric wall material and a free radical initiator and said first solution to form a first composition,
c) emulsifying said first composition,
d) mixing said first composition for at least 15 minutes at a temperature from about 20° C. to about 100° C. or 20° C. to about 95° C., e) optionally combining any structurant and/or agglomeration agent with said first composition during step d) thereafter, f) optionally spray drying said first composition.

In a further embodiment, the aforementioned benefit agent delivery particles have a zeta potential of from about −10 mV to about +50 mV, from about +2 mV to about +40 mV, or from about +5 mV to about +25 mV.

Compositions Comprising Particles

In one aspect, a composition a comprising a consumer product adjunct material and benefit agent delivery particles comprising a core and a shell, said shell encapsulating said core, said shell comprising:

a) styrene maleic anhydride monomethylmaleate, and/or a salt thereof, in one aspect, styrene maleic anhydride monomethylmaleate di-sodium salt and/or styrene maleic anhydride monomethylmaleate ammonia-salt; in one aspect, said styrene maleic anhydride monomethylmaleate, and/or a salt thereof has one, two or three of the following properties:
  (i) a molar ratio of styrene to maleic anhydride of from about 9:1 to about 1:9, from about 6:4 to about 4:6 or about 1:1;
  (ii) a weight average molecular weight of from about 1,000 Da to about 100,000,000 Da or from about 50,000 Da to about 500,000 Da;
  (iii) a density of from about 1.03 $g/cm^3$ to about 1.11 $g/cm^3$ b) optionally:
  (i) an aminoplast polymer, in one aspect, said aminoplast polymer comprises a material selected from the group consisting of a reaction product of melamine and formaldehyde, a reaction product of urea and formaldehyde and mixtures thereof, in one aspect, a material selected from the group consisting of methylol melamine, methylated methylol melamine, dimethylol urea, methylated dimethylol urea and mixtures thereof
  (ii) a material selected from the group consisting of a polyacrylate, a polyethylene glycol acrylate, a polyurethane acrylate, an epoxy acrylate, a polymethacrylate, a polyethylene glycol methacrylate, a polyurethane methacrylate, an epoxy methacrylate and mixtures thereof, in one aspect, said polyacrylate is a reaction product of:
    an oil soluble or dispersible amine, in one aspect, said amine is a secondary or tertiary amine, in one aspect, said amine is an amine oligomer, in one aspect, said amine is an aminoalkyl acrylate or aminoalkyl methacrylate, in one aspect, said amine is selected from diethylaminoethyl methacrylate, dimethylaminoethyl methacrylate, or tertiary butyl aminoethyl methacrylate;
    with a multifunctional acrylate or methacrylate monomer or oligomer; in one aspect, said multifunctional acrylate or methacrylate monomer or oligomer is selected from the group consisting of aliphatic or aromatic urethane diacrylate, aliphatic or aromatic urethane triacrylate, aliphatic or aromatic urethane tetracrylate, aliphatic or aromatic urethane hexacrylate, pentaerithrotol diacrylate, pentaerithrotol triacrylate, pentaerithrotol tetracrylate, dipentaerythritol pentaacrylate, ethoxylated pentaertythritol tetraacrylate and mixtures thereof, in one aspect, said multifunctional acrylate or methacrylate monomer or oligomer is selected from the group consisting of allyl methacrylate, triethylene glycol dimethacrylate, epoxy acrylate, epoxymethacrylates and mixtures thereof; and
    an oil soluble acid, in one aspect, said oil soluble acid is selected from the group consisting of Carboxy acids comprising one or more a monoalkyl maleate moieties, organic sulfonic acid, and mixtures thereof in one aspect, said Carboxy acids comprising one or more a monoalkyl maleate moieties, in one aspect, Beta-carboxyethyl acrylate, in one aspect, said organic sulfonic acid is selected from the group consisting of alkyl benzene sulfonic acid, dodecyl diphenyl oxidedisulfonic acid, branched C12 diphenyl oxide disulfonic acid, 4-hydrizino benzene sulfonic acid acrylic acid and mixtures thereof;
  (iii) a reaction product of one or more aromatic alcohols and one or materials comprising at least one aldehyde moiety in one aspect said aromatic alcohols may be phenols that comprise two or more hydroxyl groups, in one aspect, said aromatic alcohols are selected from the group consisting of brenzcatechin (pyrocatechol), resorcinol, hydroquinone, 1,4 naphthohydroxyquinone, phloroglucinol, pyrrogallol, hydroxyhydroquinone and mixtures thereof. In one aspect, said materials comprising one or more aldehyde moieties comprise two, three, or four free aldehyde moieties per molecule, in one aspect, said materials comprising one or more aldehyde moieties is selected from the group consisting of glyoxal, gluteraldehyde, succindialdehyde; and/or
  (iv) the reaction product of melamine or a methylenediamine which has the structure $CH_2(NH_2)_2$, a material comprising one or more aldehyde moieties, an alkoxy ethanol and an acid, in one aspect, said material comprising one or more aldehyde moieties is selected from the group consisting of glyoxal, a C(4,6)-2,2-dialkoxy-ethanal, in one aspect, 2,2-dimethoxy-ethanal, or 2,2-diethoxy-ethanal, a glyoxalate and mixtures thereof c) optionally, a colloid,
  (i) in one aspect, when said benefit agent delivery particle's shell comprises a reaction product of one or more of melamine and formaldehyde, methylol melamine, methylated methylol melamine, urea and formaldehyde, dimethylol urea, or methylated dimethylol urea said colloid is selected from alkyl acrylate acrylic acid copolymer and mixtures thereof, in one aspect said colloid is selected from alkyl acrylate acrylic acid copolymers wherein the alkyl acrylate is selected from methyl acrylate, ethyl acrylate, propyl acrylate, butyl acrylate, hexyl acrylate, cyclohexyl acrylate, ethyl hexyl acrylate and mixtures thereof;
  (ii) in one aspect, when said benefit agent delivery particle's shell comprises one or more of poly(meth)acrylate or alkyl esters of (meth)acrylic acid said colloid is selected from alkyl acrylate acrylic acid copolymer and mixtures thereof, in one aspect said colloid is selected from alkyl acrylate acrylic acid copolymers wherein the alkyl acrylate is selected from methyl acrylate, ethyl acrylate, propyl acrylate, butyl acrylate, pentyl acrylate, hexyl acrylate, cyclohexyl acrylate, ethyl hexyl acrylate and mixtures thereof;
  (iii) in one aspect, when said benefit agent delivery particle's shell comprises a reaction product of one or more aromatic alcohols and one or materials comprising at least one aldehyde moiety, said colloid is selected from alkyl acrylate acrylic acid copolymer and mixtures thereof, in one aspect, said colloid is selected from alkyl acrylate acrylic acid copolymers wherein the alkyl acrylate is selected from methyl acrylate, ethyl acrylate, propyl acrylate, butyl acrylate, hexyl acrylate, cyclohexyl acrylate, ethyl hexyl acrylate and mixtures thereof;

(iv) in one aspect, when said benefit agent delivery particle's shell comprises a reaction product of melamine or a methylenediamine $CH_2(NH_2)_2$, a material comprising one or more aldehyde moieties, an alkoxy ethanol and an acid, said colloid is selected from alkyl acrylate acrylic acid copolymer and mixtures thereof, in one aspect said colloid is selected from alkyl acrylate acrylic acid copolymers wherein the alkyl acrylate is selected from methyl acrylate, ethyl acrylate, propyl acrylate, butyl acrylate, hexyl acrylate, cyclohexyl acrylate, ethyl hexyl acrylate and mixtures thereof; and c) optionally, an emulsifier, in one aspect, said emulsifier is selected from cationic emulsifiers of amine polymers with primary, secondary or tertiary functionality or nonionic emulsifiers having a hydroxyl, ether, ester, ketone, or amide functionality;

said composition being a consumer product, is disclosed.

In one aspect of said composition, said composition comprises:

a) benefit agent delivery particles, comprising:
  (i) a core material comprising selected from the group consisting of perfume, suds suppressor or mixtures thereof;
  (ii) a shell that encapsulates said core material, said shell comprising a material selected from the group consisting of an aminoplast polymer, a polyacrylate or mixtures thereof; and based on total benefit agent particle shell weight, from about 1% to about 80%, from about 30% to about 75% or from about 50% to about 70% of a styrene maleic anhydride monomethylmaleate, and/or a salt thereof;
  (iii) a colloid, in one aspect, said composition comprises, based on total benefit agent particle shell weight, from about 1% to about 27%, from about 3% to about 24%, from about 6% to about 22% of said colloid, in one aspect, said colloid comprises Colloid 121;

b) a consumer product adjunct material and c) optionally, a deposition aid.

Voguish one aspect of said composition, said benefit agent delivery particles, have a mean particle size of from about 1 micrometers to about 100 micrometers, from about 5 micrometers to about 80 micrometers or 8 micrometers to about 50 micrometers at least 75% of said benefit agent delivery particles having a fracture strength of from about 0.2 MPa to about 10 MPa; and, in one aspect, said particles having a benefit agent leakage of from 0% to about 30%.

In one aspect of said composition, said benefit agent delivery particles, have a mean particle size of from about 1 micrometers to about 100 micrometers, from about 5 micrometers to about 80 micrometers or 8 micrometers to about 50 micrometers and, in one aspect, at least 75% of said benefit agent delivery particles have a benefit agent leakage of from 0% to about 30%.

In one aspect of said composition, said shell comprises an aminoplast polymer, in one aspect said shell comprises from about 50% to about 100%, from about 70% to about 100% or even from about 80% to about 100% of said aminoplast polymer.

In one aspect of said composition, said shell comprises an aminoplast polymer comprising a material selected from the group consisting of a resin of melamine and formaldehyde, a mixed resin of urea-formaldehyde, maleic anhydride copolymers, a melamine resin and mixtures thereof.

In one aspect of said composition, said shell comprises a polyacrylate, in one aspect, said shell comprises from about 50% to about 100%, from about 70% to about 100% or even from about 80% to about 100% of said polyacrylate polymer, in one aspect said polyacrylate comprises a polyacrylate cross polymer.

In one aspect of said composition, said shell comprises a polyacrylate that comprises a material selected from the group consisting of an amine acrylate, methacrylate monomer, a carboxylic acid acrylate, carboxylic acid methacrylate monomer and mixtures thereof.

In one aspect of said composition, said composition comprises a deposition aid.

In one aspect of said composition, said deposition aid coats the outer surface of said shell.

In one aspect of said composition, said deposition aid comprises a material selected from the group consisting of poly(meth)acrylate, poly(ethylene-maleic anhydride), polyamine, wax, polyvinylpyrrolidone, polyvinylpyrrolidone co-polymers, polyvinylpyrrolidone-ethyl acrylate, polyvinylpyrrolidone-vinyl acrylate, polyvinylpyrrolidone methylacrylate, polyvinylpyrrolidone/vinyl acetate, polyvinyl acetal, polyvinyl butyral, polysiloxane, poly(propylene maleic anhydride), maleic anhydride derivatives, co-polymers of maleic anhydride derivatives, polyvinyl alcohol, styrene-butadiene latex, gelatin, gum Arabic, carboxymethyl cellulose, carboxymethyl hydroxyethyl cellulose, hydroxyethyl cellulose, other modified celluloses, sodium alginate, chitosan, casein, pectin, modified starch, polyvinyl acetal, polyvinyl butyral, polyvinyl methyl ether/maleic anhydride, polyvinyl pyrrolidone and its co polymers, poly(vinyl pyrrolidone/methacrylamidopropyl trimethyl ammonium chloride), polyvinylpyrrolidone/vinyl acetate, polyvinyl pyrrolidone/dimethylaminoethyl methacrylate, polyvinyl amines, polyvinyl formamides, polyallyl amines and copolymers of polyvinyl amines, polyvinyl formamides, and polyallyl amines and mixtures thereof.

In one aspect of said composition, said deposition aid comprises a material selected from the group consisting of poly(meth)acrylates, poly(ethylene-maleic anhydride), polyamine, polyvinylpyrrolidone, polyvinylpyrrolidone-ethyl acrylate, polyvinylpyrrolidone-vinyl acrylate, polyvinylpyrrolidone methylacrylate, polyvinylpyrrolidone/vinyl acetate, polyvinyl acetal, polyvinyl butyral, polysiloxane, poly(propylene maleic anhydride), maleic anhydride derivatives, co-polymers of maleic anhydride derivatives, polyvinyl alcohol, carboxymethyl cellulose, carboxymethyl hydroxyethyl cellulose, hydroxyethyl cellulose, polyvinyl methyl ether/maleic anhydride, poly(vinyl pyrrolidone/methacrylamidopropyl trimethyl ammonium chloride), polyvinylpyrrolidone/vinyl acetate, polyvinyl pyrrolidone/dimethylaminoethyl methacrylate, polyvinyl amines, polyvinyl formamides, polyallyl amines and copolymers of polyvinyl amines, polyvinyl formamides, and polyallyl amines and mixtures thereof.

In one aspect of said composition, said deposition aid comprises a material selected from the group consisting of poly(meth)acrylates, poly(ethylene-maleic anhydride), polyamine, polyvinylpyrrolidone, polyvinylpyrrolidone-ethyl acrylate, polyvinylpyrrolidone-vinyl acrylate, polyvinylpyrrolidone methylacrylate, polyvinylpyrrolidone/vinyl acetate, polyvinyl acetal, polysiloxane, poly(propylene maleic anhydride), maleic anhydride derivatives, co-polymers of maleic anhydride derivatives, polyvinyl alcohol, carboxymethyl cellulose, carboxymethyl hydroxyethyl cellulose, hydroxyethyl cellulose, polyvinyl methyl ether/maleic anhydride, polyvinylpyrrolidone/vinyl acetate, polyvinyl pyrrolidone/dimethylaminoethyl methacrylate, polyvinyl amines, polyvinyl formamides, polyallyl amines and copolymers of polyvinyl amines, polyvinyl formamides, and polyallyl amines and mixtures thereof.

In one aspect of said composition, at least 75% of said benefit agent delivery particles have a particle size of from about 1 micrometers to about 80 micrometers.

In one aspect of said composition, at least 75% of said benefit agent delivery particles have a particle wall thickness of from about 10 nm to about 250 nm, from about 20 nm to about 200 nm, or from 25 nm to about 180 nm.

In one aspect of said composition, said benefit agent delivery particles' core material comprises a suds suppressor material selected from the group consisting of silicone oils, silicone resins, silicone polymers, silica and mixtures thereof.

In one aspect of said composition, said benefit agent delivery particles' core material comprises, based on total benefit agent delivery particle weight, at least about 20 wt %, from about 20% to about 99%, from about 70% to about 98%, from about 85% to about 96% benefit agent.

In one aspect of said composition, said benefit agent delivery particles' core material comprises:

a) a perfume composition having a C log P of less than 4.5;
b) a perfume composition comprising, based on total perfume composition weight, 60% perfume materials having a C log P of less than 4.0;
c) a perfume composition comprising, based on total perfume composition weight, 35% perfume materials having a C log P of less than 3.5;
d) a perfume composition comprising, based on total perfume composition weight, 40% perfume materials having a C log P of less than 4.0 and at least 1% perfume materials having a C log P of less than 2.0;
e) a perfume composition comprising, based on total perfume composition weight, 40% perfume materials having a C log P of less than 4.0 and at least 15% perfume materials having a C log P of less than 3.0;
f) a perfume composition comprising, based on total perfume composition weight, at least 1% butanoate esters and at least 1% of pentanoate esters;
g) a perfume composition comprising, based on total perfume composition weight, at least 2% of an ester comprising an allyl moiety and at least 10% of another perfume comprising an ester moiety;
h) a perfume composition comprising, based on total perfume composition weight, at least 1% of an aldehyde comprising an alkyl chain moiety;
i) a perfume composition comprising, based on total perfume composition weight, at least 2% of a butanoate ester;
j) a perfume composition comprising, based on total perfume composition weight, at least 1% of a pentanoate ester;
k) a perfume composition comprising, based on total perfume composition weight, at least 3% of an ester comprising an allyl moiety and 1% of an aldehyde comprising an alkyl chain moiety;
l) a perfume composition comprising, based on total perfume composition weight, at least 25% of a perfume comprising an ester moiety and 1% of an aldehyde comprising an alkyl chain moiety;
m) a perfume compositions comprising, based on total perfume composition weight, at least 2% of a material selected from 4-(2,6,6-trimethyl-1-cyclohexenyl)-3-buten-2-one, 4-(2,6,6-trimethyl-2-cyclohexenyl)-3-buten-2-one and 3-buten-2-one,3-methyl-4-(2,6,6-trimethyl-1-cyclohexen-2-yl)- and mixtures thereof;
n) a perfume composition comprising, based on total perfume composition weight, at least 0.1% of tridec-2-enonitrile, and mandaril, and mixtures thereof;
o) a perfume composition comprising, based on total perfume composition weight, at least 2% of a material selected from 3,7-dimethyl-6-octene nitrile, 2-cyclohexylidene-2-phenylacetonitrile and mixtures thereof;
p) a perfume composition comprising, based on total perfume composition weight, at least 80% of one or more perfumes comprising a moiety selected from the group consisting of esters, aldehydes, ionones, nitriles, ketones and combinations thereof;
q) a perfume composition comprising, based on total perfume composition weight, at least 3% of an ester comprising an allyl moiety; a perfume composition comprising, based on total perfume composition weight, at least 20% of a material selected from the group consisting of: 1-methylethyl-2-methylbutanoate; ethyl-2-methyl pentanoate; 1,5-dimethyl-1-ethenyl-hexyl-4-enyl acetate; p-meth-1-en-8-yl acetate; 4-(2,6,6-trimethyl-2-cyclohexenyl)-3-buten-2-one; 4-acetoxy-3-methoxy-1-propenylbenzene; 2-propenyl cyclohexanepropionate; bicyclo[2.2.1]hept-5-ene-2-carboxylic acid,3-(1-methylethyl)-ethyl ester; bycyclo [2.2.1]heptan-2-ol, 1,7,7-trimethyl-, acetate; 1,5-dimethyl-1-ethenylhex-4-enylacetate; hexyl 2-methyl propanoate; ethyl-2-methylbutanoate; 4-undecanone; 5-heptyldihydro-2(3h)-furanone; 1,6-nonadien-3-ol,3,7dimethyl-; 3,7-dimethylocta-1,6-dien-3-o; 3-cyclohexene-1-carboxaldehyde,dimethyl-; 3,7-dimethyl-6-octene nitrile; 4-(2,6,6-trimethyl-1-cyclohexenyl)-3-buten-2-one; tridec-2-enonitrile; patchouli oil; ethyl tricycle [5.2.1.0]decan-2-carboxylate; 2,2-dimethyl-cyclohexanepropanol; hexyl ethanoate, 7-acetyl,1,2,3,4,5,6,7,8-octahydro-1,1,6,7-tetramethyl naphtalene; allyl-cyclohexyloxy acetate; methyl nonyl acetic aldehyde; 1-spiro[4,5]dec-7-en-7-yl-4-pentenen-1-one; 7-octen-2-ol,2-methyl-6-methylene-,dihydro; cyclohexanol,2-(1,1-dimethylethyl)-, acetate; hexahydro-4,7-methanoinden-5(6)-yl propionatehexahydro-4,7-methanoinden-5(6)-yl propionate; 2-methoxynaphtalene; 1-(2,6,6-trimethyl-3-cyclohexenyl)-2-buten-1-one; 1-(2,6,6-trimethyl-2-cyclohexenyl)-2-buten-1-one; 3,7-dimethyloctan-3-ol; 3-buten-2-one,3-methyl-4-(2,6,6-trimethyl-1-cyclohexen-2-yl)-; hexanoic acid, 2-propenyl ester; (Z)-non-6-en-1-al; 1-decyl aldehyde; 1-octanal; 4-t-butyl-α-methylhydrocinnamaldehyde; α-hexylcinnamaldehyde; ethyl-2,4-hexadienoate; 2-propenyl 3-cyclohexanepropanoate; and mixtures thereof;
r) a perfume composition comprising, based on total perfume composition weight, at least 20% of a material selected from the group consisting of: 1-methylethyl-2-methylbutanoate; ethyl-2-methyl pentanoate; 1,5-dimethyl-1-ethenylhex-4-enyl acetate; p-menth-1-en-8-yl acetate; 4-(2,6,6-trimethyl-2-cyclohexenyl)-3-buten- 2-one; 4-acetoxy-3-methoxy-1-propenylbenzene; 2-propenyl cyclohexanepropionate; bicyclo[2.2.1]hept-5-ene-2-carboxylic acid,3-(1-methylethyl)-ethyl ester; bycyclo[2.2.1]heptan-2-ol, 1,7,7-trimethyl-, acetate; 1,5-dimethyl-1-ethenylhex-4-enyl acetate; hexyl 2-methyl propanoate; ethyl-2-methylbutanoate,4-undecanolide; 5-heptyldihydro-2(3h)-furanone; 5-hydroxydodecanoic acid; decalactones; undecalactones, 1,6-nonadien-3-ol,3,7dimethyl-; 3,7-dimethylocta-1,6-dien-3-ol; 3-cyclohexene-1-carboxaldehyde,dimethyl-; 3,7-dimethyl-6-octene nitrile; 4-(2,6,6-trimethyl-1-cyclohexenyl)-3-buten-2-one; tridec-2-enonitrile; patchouli oil; ethyl tricycle [5.2.1.0]decan-2-carboxylate; 2,2-dimethyl-cyclohexanepropanol; allyl-cyclohexyloxy acetate; methyl nonyl acetic aldehyde; 1-spiro[4,5]dec-7-en-7-yl-4-pentenen-1-one; 7-octen-2-ol,2-methyl-6-methylene-,dihydro, cyclohexanol,2-(1,1-dimethylethyl)-, acetate; hexahydro-4,7-methanoinden-5(6)-yl propionatehexahydro-4,7-methanoinden-5(6)-yl propionate; 2-methoxynaphtalene; 1-(2,6,6-trimethyl-3-cyclohexenyl)-2-buten-1-one; 1-(2,6,6-trimethyl-2-cyclohexenyl)-2-buten-1-one; 3,7-dimethyloctan-3-ol; 3-buten-2-one,3-methyl-4-(2,6,6-trimethyl-1-cyclohexen-2-yl)-; hexanoic acid, 2-propenyl ester; (Z)-non-6-en-1-al; 1-decyl aldehyde; 1-octanal; 4-t-butyl-α-methylhydrocinnamaldehyde; ethyl-2,4-hexadienoate; 2-propenyl 3-cyclohexanepropanoate; and mixtures thereof;
s) a perfume composition comprising, based on total perfume composition weight, at least 5% of a material selected from the group consisting of 3-cyclohexene-1-carboxaldehyde,dimethyl-; 3-buten-2-one,3-methyl-4-(2,6,6-trimethyl-1-cyclohexen-2-yl)-; patchouli oil; Hexanoic acid, 2-propenyl ester; 1-Octanal; 1-decyl aldehyde; (Z)-non-6-en-1-al; methyl nonyl acetic aldehyde; ethyl-2-methylbutanoate; 1-methylethyl-2-methylbutanoate; ethyl-2-methyl pentanoate; 4-hydroxy-3-ethoxybenzaldehyde; 4-hydroxy-3-methoxybenzaldehyde; 3-hydroxy-2-methyl-4-pyrone; 3-hydroxy-2-ethyl-4-pyrone and mixtures thereof;
t) a perfume composition comprising, based on total perfume composition weight, less than 10% perfumes having a C log P greater than 5.0;
u) a perfume composition comprising geranyl palmitate; or
v) a perfume composition comprising a first and an optional second material, said first material having:
(i) a C log P of at least 2;
(ii) a boiling point of less than about 280° C.; and second optional second material, when present, having
(iii) a C log P of less than 2.5.

In one aspect of said composition, said composition comprises a material selected from the group consisting of a formaldehyde scavenger, a structurant, an anti-agglomeration agent and mixtures thereof.

In one aspect of said composition, said composition comprises less than 150 ppm, less than 100 ppm, less than 50 ppm, less than 10 ppm, less than 5 ppm or even less than 1 ppm formaldehyde.

In one aspect of said composition, said composition, has a viscosity of from 1 to 1500 centipoises (1-1500 mPa*s), from 100 to 1000 centipoises (100-1000 mPa*s), or from 200 to 500 centipoises (200-500 mPa*s) at 20 s$^{-1}$ and 21° C. The rheology described therein may be achieved using internal existing structuring with detergent ingredients or by employing an external rheology modifier. Laundry care compositions, such as detergent liquid compositions typically have a high shear rate viscosity of from about 100 centipoise to 1500 centipoise, or from 100 cps to 1000 cps. Unit Dose laundry care compositions, such as detergent liquid compositions typically have high shear rate viscosity of from 400 cps to 1000 cps. Laundry care compositions such as laundry softening compositions typically have high shear rate viscosity of from 10 cps to 1000 cps, from 10 cps to 800 cps or from 10 cps to 500 cps. Hand dishwashing compositions typically have high shear rate viscosity of from 300 cps to 4000 cps, or 300 cps to 1000 cps.

In one aspect of said composition, said composition comprises from about 0.001% to about 25%, based on total consumer product mass weight of said benefit agent delivery particles.

In one aspect of said composition, said composition comprises a structurant, said structurant comprising a material selected from the group consisting of polysaccharides, modified celluloses, modified proteins, inorganic salts, quaternized polymeric materials, imidazoles; nonionic polymers having a pKa less than 6.0, polyurethanes, bacterial cellulose, coated bacterial cellulose, non-polymeric crystalline hydroxyl-functional materials, polymeric structuring agents, di-amido gellants and mixtures thereof.

In one aspect of said composition, said benefit agent delivery particle has a zeta potential of from about −10 mV to about +50 mV, from about +2 mV to about +40 mV, or from about +5 mV to about +25 mV.

In one aspect, a composition comprising a consumer adjunct material and benefit agent delivery particle produced by the process of:
a) preparing a first solution comprising, a non-esterified styrene maleic-anhydride copolymer emulsifier, preferably said non-esterified styrene maleic-anhydride copolymer emulsifier has a hydrolysis degree of from about 20% to about 95%, preferably from about 25% to about 80%, more preferably from about 30% to about 70%, most preferably from about 40% to about 60% and a first resin, in one aspect, based on total solution weight, from about 20% to about 100% of a non-esterified styrene maleic-anhydride copolymer emulsifier and a first resin, the ratio of said styrene-maleic anhydride copolymer and said first resin being from about 0.1:1 to about 10:1;
b) preparing a second solution comprising based on total solution weight from about 20% to about 95% water, a second emulsifier and a second resin, the ratio of said second emulsifier and said second resin being from about 0:1 to about 3:1;
c) combining a core material and said first solution to form a first composition;
d) emulsifying said first composition;
e) combining said first composition and said second solution to form a second composition and optionally combining any processing aids and said second composition;
f) mixing said second composition for at least 15 minutes at a temperature of from about 20° C. to about 100° C. or 20° C. to about 95° C. and optionally combining any processing aids to said second composition;
g) optionally combining any scavenger material, structurant, and/or anti-agglomeration agent with said second composition during step f) or thereafter; and
h) optionally spray drying said second composition is disclosed.

In one aspect of said composition, said non-esterified styrene maleic-anhydride copolymer comprises styrene maleic anhydride monomethylmaleate, sodium salt.

In one aspect of said composition, said resin material comprises a reaction product of an aldehyde, with an amine, amine is selected from the group consisting of melamine, urea, benzoguanamine, glycoluril, and mixtures thereof.

In one aspect a composition comprising a consumer adjunct material and benefit agent delivery particle produced by the process of:
a) preparing a first solution comprising, based on total solution weight from about 60% to 100% of a non-esterified styrene maleic anhydride emulsifier, preferably said non-esterified styrene maleic-anhydride copolymer emulsifier has a hydrolysis degree of from about 20% to about 95%, preferably from about 25% to about 80%, more preferably from about 30% to about 70%, most preferably from about 40% to about 60%;
b) combining a core material which includes monomeric wall material and a free radical initiator and said first solution to form a first composition,
c) emulsifying said first composition,
d) mixing said first composition for at least 15 minutes at a temperature from about 20° C. to about 100° C. or 20° C. to about 95° C.,
e) optionally combining any structurant and/or agglomeration agent with said first composition during step d) thereafter,
f) optionally spray drying said first composition
is disclosed.

Applicants' compositions comprise any embodiment of the particle disclosed in the present application—including any embodiment produced by the benefit agent delivery making process detailed in the present specification. In one aspect, said composition is a consumer product. While the precise level of particle that is employed depends on the type and end use of the composition, a composition may comprise from about 0.01 to about 10, from about 0.1 to about 10, or even from about 0.2 to about 5 weight % of said particle based on total composition weight. In one aspect, a consumer product comprising from about 0.001% to about 25%, from about 0.001% to about 10%, or from about 0.01% to about 3%, based on total consumer product mass weight, of the aforementioned benefit agent delivery particles is disclosed.

In one aspect, a cleaning composition comprising from about 0.005% to about 10%, from about 0.01% to about 3%, or from about 0.1% to about 1% based on total cleaning composition mass weight of the aforementioned benefit agent delivery particles is disclosed.

In one aspect, a fabric care composition comprising from about 0.005% to about 10%, from about 0.01% to about 3%, or from about 0.1% to about 1% based on total fabric care mass weight of the aforementioned benefit agent delivery particle composition is disclosed.

In one aspect, when the aforementioned particle composition is employed in a consumer product, for example a liquid consumer product, the particle composition may have a deposition of at least 10%, 20%, 30%, 40%, 50%, 60%, 70%, 80%, 90%, or even 100%.

In one aspect, when the aforementioned particle composition is employed in a consumer product, for example a liquid consumer product, the particle composition may have less than 50%, 40%, 30%, 20%, 10% or even 0% leakage of the encapsulated benefit agent from the microcapsules of said particle composition into said consumer product.

In one aspect, a cleaning composition may comprise, from about 0.1 to about 1 weight % of such particle based on total cleaning composition weight of such particle. In one aspect, a fabric treatment composition may comprise, based on total fabric treatment composition weight, from about 0.01 to about 10% of such particle.

In one aspect, said benefit agent delivery particles may have any combination of the aforementioned parameters as listed in the aforementioned aspects.

Suitable materials for making may be supplied from one or more of the following companies Firmenich (Geneva, Switzerland), Givaudan (Argenteuil, France), IFF (Hazlet, N.J., U.S.A), Quest (Mount Olive, N.J., U.S.A.), Bedoukian (Danbury, Conn., U.S.A.), Sigma Aldrich (St. Louis, Mo., U.S.A.), Millennium Specialty Chemicals (Olympia Fields, Ill., U.S.A.), Polarone International (Jersey City, N.J., U.S.A.), Fragrance Resources (Keyport, N.J., U.S.A.), and Aroma & Flavor Specialties (Danbury, Conn., U.S.A.).

Process of Making Consumer Product Comprising Benefit Agent Containing Delivery Particles In one aspect, the compositions disclosed herein can be made by combining the particles disclosed herein with the desired consumer product adjuncts materials. The particles may be combined with such one or more consumer product adjuncts materials when the particles are in one or more forms, including a slurry form, neat particle form and spray dried particle form. The particles may be combined with such consumer product adjuncts materials by methods that include mixing and/or spraying.

The cleaning and/or treatment compositions of the present invention can be formulated into any suitable form and prepared by any process chosen by the formulator, non-limiting examples of which are described in U.S. Pat. No. 5,879,584 which is incorporated herein by reference.

Suitable equipment for use in the processes disclosed herein may include continuous stirred tank reactors, homogenizers, turbine agitators, recirculating pumps, paddle mixers, plough shear mixers, ribbon blenders, vertical axis granulators and drum mixers, both in batch and, where available, in continuous process configurations, spray dryers, and extruders. Such equipment can be obtained from Lödige GmbH (Paderborn, Germany), Littleford Day, Inc. (Florence, Ky., U.S.A.), Forberg AS (Larvik, Norway), Glatt Ingenieurtechnik GmbH (Weimar, Germany), Niro (Søborg, Denmark), Hosokawa Bepex Corp. (Minneapolis, Minn., U.S.A.), Arde Barinco (New Jersey, U.S.A.).

Consumer Product Adjunct Materials

The disclosed compositions may include additional adjunct ingredients that include: bleach activators, surfactants, builders, chelating agents, dye transfer inhibiting agents, dispersants, enzymes, and enzyme stabilizers, catalytic metal complexes, polymeric dispersing agents, clay and soil removal/anti-redeposition agents, brighteners, suds suppressors, dyes, additional perfumes and perfume delivery systems, structure elasticizing agents, fabric softeners, carriers, hydrotropes, processing aids, structurants, anti-agglomeration agents, coatings, formaldehyde scavengers and/or pigments. Other embodiments of Applicants' compositions do not contain one or more of the following adjuncts materials: bleach activators, surfactants, builders, chelating agents, dye transfer inhibiting agents, dispersants, enzymes, and enzyme stabilizers, catalytic metal complexes, polymeric dispersing agents, clay and soil removal/anti-redeposition agents, brighteners, suds suppressors, dyes, additional perfumes and perfume delivery systems, structure elasticizing agents, fabric softeners, carriers, hydrotropes, processing aids, structurants, anti-agglomeration agents, coatings, formaldehyde scavengers and/or pigments. The precise nature of these additional components, and levels of incorporation thereof, will depend on the physical form of the composition and the nature of the operation for which it is to be used. However, when one or more adjuncts are present, such one or more adjuncts may be present as detailed below. The following is a non-limiting list of suitable additional adjuncts.

Deposition Aid—In one aspect, the fabric treatment composition may comprise from about 0.01% to about 10%, from about 0.05 to about 5%, or from about 0.15 to about 3% of a deposition aid. In one aspect, the deposition aid may be a cationic or amphoteric polymer. In another aspect, the deposition aid may be a cationic polymer. Cationic polymers in general and their method of manufacture are known in the literature. In one aspect, the cationic polymer may have a cationic charge density of from about 0.005 to about 23 meq/g, from about 0.01 to about 12 meq/g, or from about 0.1 to about 7 meq/g, at the pH of the composition. For amine-containing polymers, wherein the charge density depends on the pH of the composition, charge density is measured at the intended use pH of the product. Such pH will generally range from about 2 to about 11, more generally from about 2.5 to about 9.5. Charge density is calculated by dividing the number of net charges per repeating unit by the molecular weight of the repeating unit. The positive charges may be located on the backbone of the polymers and/or the side chains of polymers.

In another aspect, the deposition aid may comprise a cationic acrylic based polymer. In a further aspect, the deposition aid may comprise a cationic polyacrylamide. In another aspect, the deposition aid may comprise a polymer comprising polyacrylamide and polymethacrylamidopropyl trimethylammonium cation. In another aspect, the deposition aid may comprise poly(acrylamide-N-dimethyl aminoethyl acrylate) and its quaternized derivatives.

In another aspect, the deposition aid may be selected from the group consisting of cationic or amphoteric polysaccharides. In one aspect, the deposition aid may be selected from the group consisting of cationic and amphoteric cellulose ethers, cationic or amphoteric galactomannan, cationic guar gum, cationic or amphoteric starch, and combinations thereof Another group of suitable cationic polymers may include alkylamine-epichlorohydrin polymers which are reaction products of amines and oligoamines with epichlorohydrin. Another group of suitable synthetic cationic polymers may include polyamidoamine-epichlorohydrin (PAE) resins of polyalkylenepolyamine with polycarboxylic acid. The most common PAE resins are the condensation products of diethylenetriamine with adipic acid followed by a subsequent reaction with epichlorohydrin.

The weight-average molecular weight of the polymer may be from about 500 Daltons to about 5,000,000 Daltons, or from about 1,000 Daltons to about 2,000,000 Daltons, or from about 2,500 Daltons to about 1,500,000 Daltons, as determined by size exclusion chromatography relative to polyethylene oxide standards with RI detection. In one aspect, the MW of the cationic polymer may be from about 500 Daltons to about 37,500 Daltons.

Surfactants: Surfactants utilized can be of the anionic, nonionic, zwitterionic, ampholytic or cationic type or can comprise compatible mixtures of these types. Anionic and nonionic surfactants are typically employed if the fabric care product is a laundry detergent. On the other hand, cationic surfactants are typically employed if the fabric care product is a fabric softener. In addition to the anionic surfactant, the fabric care compositions of the present invention may further contain a nonionic surfactant. The compositions of the present invention can contain up to about 30%, alternatively from about 0.01% to about 20%, more alternatively from about 0.1% to about 10%, by weight of the composition, of a nonionic surfactant. In one embodiment, the nonionic surfactant may comprise an ethoxylated nonionic surfactant. Suitable for use herein are the ethoxylated alcohols and ethoxylated alkyl phenols of the formula $R(OC_2H_4)n$ OH, wherein R is selected from the group consisting of aliphatic hydrocarbon radicals containing from about 8 to about 20 carbon atoms and alkyl phenyl radicals in which the alkyl groups contain from about 8 to about 12 carbon atoms, and the average value of n is from about 5 to about 15.

Suitable nonionic surfactants are those of the formula $R1(OC_2H_4)nOH$, wherein R1 is a $C_{10}$-$C_{16}$ alkyl group or a $C_8$-$C_{12}$ alkyl phenyl group, and n is from 3 to about 80. In one aspect, particularly useful materials are condensation products of $C_9$-$C_{15}$ alcohols with from about 5 to about 20 moles of ethylene oxide per mole of alcohol.

The fabric care compositions of the present invention may contain up to about 30%, alternatively from about 0.01% to about 20%, more alternatively from about 0.1% to about 20%, by weight of the composition, of a cationic surfactant. For the purposes of the present invention, cationic surfactants include those which can deliver fabric care benefits. Non-limiting examples of useful cationic surfactants include: fatty amines; quaternary ammonium surfactants; and imidazoline quat materials.

Non-limiting examples of fabric softening actives are N, N-bis(stearoyl-oxy-ethyl) N,N-dimethyl ammonium chloride, N,N-bis(tallowoyl-oxy-ethyl) N,N-dimethyl ammonium chloride, N,N-bis(stearoyl-oxy-ethyl) N-(2 hydroxyethyl) N-methyl ammonium methylsulfate; 1, 2 di (stearoyl-oxy) 3 trimethyl ammoniumpropane chloride; dialkylenedimethylammonium salts such as dicanoladimethylammonium chloride, di(hard)tallowdimethylammonium chloride dicanoladimethylammonium methylsulfate; 1-methyl-1-stearoylamidoethyl-2-stearoylimidazolinium methylsulfate; 1-tallowylamidoethyl-2-tallowylimidazoline; N,N"-dialkyldiethylenetriamine; the reaction product of N-(2-hydroxyethyl)-1,2-ethylenediamine or N-(2-hydroxyisopropyl)-1,2-ethylenediamine with glycolic acid, esterified with fatty acid, where the fatty acid is (hydrogenated) tallow fatty acid, palm fatty acid, hydrogenated palm fatty acid, oleic acid, rapeseed fatty acid, hydrogenated rapeseed fatty acid; polyglycerol esters (PGEs), oily sugar derivatives, and wax emulsions and a mixture of the above.

It will be understood that combinations of softener actives disclosed above are suitable for use herein.

Builders—The compositions may also contain from about 0.1% to 80% by weight of a builder. Compositions in liquid form generally contain from about 1% to 10% by weight of the builder component. Compositions in granular form generally contain from about 1% to 50% by weight of the builder component. Detergent builders are well known in the art and can contain, for example, phosphate salts as well as various organic and inorganic nonphosphorus builders. Water-soluble, nonphosphorus organic builders useful herein include the various alkali metal, ammonium and substituted ammonium polyacetates, carboxylates, polycarboxylates and polyhydroxy sulfonates. Examples of polyacetate and polycarboxylate builders are the sodium, potassium, lithium, ammonium and substituted ammonium salts of ethylene diamine tetraacetic acid, nitrilotriacetic acid, oxydisuccinic acid, mellitic acid, benzene polycarboxylic acids, and citric acid. Other polycarboxylate builders are the oxydisuccinates and the ether carboxylate builder compositions comprising a combination of tartrate monosuccinate and tartrate disuccinate. Builders for use in liquid detergents include citric acid. Suitable nonphosphorus, inorganic builders include the silicates, aluminosilicates, borates and carbonates, such as sodium and potassium carbonate, bicarbonate, sesquicarbonate, tetraborate decahydrate, and silicates having a weight ratio of SiO2 to alkali metal oxide of from about 0.5 to about 4.0, or from about 1.0 to about 2.4. Also useful are aluminosilicates including zeolites.

Dispersants—The compositions may contain from about 0.1%, to about 10%, by weight of dispersants Suitable water-soluble organic materials are the homo- or co-polymeric acids or their salts, in which the polycarboxylic acid may contain at least two carboxyl radicals separated from each other by not more than two carbon atoms. The dispersants may also be alkoxylated derivatives of polyamines, and/or quaternized derivatives.

Enzymes—The compositions may contain one or more detergent enzymes which provide cleaning performance and/or fabric care benefits. Examples of suitable enzymes include hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, ß-glucanases, arabinosidases, hyaluronidase, chondroitinase, laccase, and amylases, or mixtures thereof. A typical combination may be a cocktail of conventional applicable enzymes like protease, lipase, cutinase and/or cellulase in conjunction with amylase. Enzymes can be used at their art-taught levels, for example at levels recommended by suppliers such as Novozymes and Genencor. Typical levels in the compositions are from about 0.0001% to about 5%. When enzymes are present, they can be used at very low levels, e.g., from about 0.001% or lower; or they can be used in heavier-duty laundry detergent formulations at higher levels, e.g., about 0.1% and higher. In accordance with a preference of some consumers for "non-biological" detergents, the compositions may be either or both enzyme-containing and enzyme-free.

Dye Transfer Inhibiting Agents—The compositions may also include from about 0.0001%, from about 0.01%, from about 0.05% by weight of the compositions to about 10%, about 2%, or even about 1% by weight of the compositions of one or more dye transfer inhibiting agents such as polyvinylpyrrolidone polymers, polyamine N-oxide polymers, copolymers of N-vinylpyrrolidone and N-vinylimidazole, polyvinyloxazolidones and polyvinylimidazoles or mixtures thereof.

Chelant—The compositions may contain less than about 5%, or from about 0.01% to about 3% of a chelant such as citrates; nitrogen-containing, P-free aminocarboxylates such as EDDS, EDTA and DTPA; aminophosphonates such as diethylenetriamine pentamethylenephosphonic acid and, ethylenediamine tetramethylenephosphonic acid; nitrogen-free phosphonates e.g., HEDP; and nitrogen or oxygen containing, P-free carboxylate-free chelants such as compounds of the general class of certain macrocyclic N-ligands such as those known for use in bleach catalyst systems.

Brighteners—The compositions may also comprise a brightener (also referred to as "optical brightener") and may include any compound that exhibits fluorescence, including compounds that absorb UV light and reemit as "blue" visible light. Non-limiting examples of useful brighteners include: derivatives of stilbene or 4,4'-diaminostilbene, biphenyl, five-membered heterocycles such as triazoles, pyrazolines, oxazoles, imidiazoles, etc., or six-membered heterocycles (coumarins, naphthalamide, s-triazine, etc.). Cationic, anionic, nonionic, amphoteric and zwitterionic brighteners can be used. Suitable brighteners include those commercially marketed under the trade name Tinopal-UNPA-GX® by Ciba Specialty Chemicals Corporation (High Point, N.C.).

Bleach system—Bleach systems suitable for use herein contain one or more bleaching agents. Non-limiting examples of suitable bleaching agents include catalytic metal complexes; activated peroxygen sources; bleach activators; bleach boosters; photobleaches; bleaching enzymes; free radical initiators; $H_2O_2$; hypohalite bleaches; peroxygen sources, including perborate and/or percarbonate and combinations thereof. Suitable bleach activators include perhydrolyzable esters and perhydrolyzable imides such as, tetraacetyl ethylene diamine, octanoylcaprolactam, benzoyloxybenzenesulphonate, nonanoyloxybenzene-sulphonate, benzoylvalerolactam, dodecanoyloxybenzenesulphonate. Other bleaching agents include metal complexes of transitional metals with ligands of defined stability constants.

Stabilizer—The compositions may contain one or more stabilizers and thickeners. Any suitable level of stabilizer may be of use; exemplary levels include from about 0.01% to about 20%, from about 0.1% to about 10%, or from about 0.1% to about 3% by weight of the composition. Non-limiting examples of stabilizers suitable for use herein include crystalline, hydroxyl-containing stabilizing agents, trihydroxystearin, hydrogenated oil, or a variation thereof, and combinations thereof. In some aspects, the crystalline, hydroxyl-containing stabilizing agents may be water-insoluble wax-like substances, including fatty acid, fatty ester or fatty soap. In other aspects, the crystalline, hydroxyl-containing stabilizing agents may be derivatives of castor oil, such as hydrogenated castor oil derivatives, for example, castor wax. The hydroxyl containing stabilizers are disclosed in U.S. Pat. Nos. 6,855,680 and 7,294,611. Other stabilizers include thickening stabilizers such as gums and other similar polysaccharides, for example gellan gum, carrageenan gum, and other known types of thickeners and rheological additives. Exemplary stabilizers in this class include gum-type polymers (e.g. xanthan gum), polyvinyl alcohol and derivatives thereof, cellulose and derivatives thereof including cellulose ethers and cellulose esters and tamarind gum (for example, comprising xyloglucan polymers), guar gum, locust bean gum (in some aspects comprising galactomannan polymers), and other industrial gums and polymers.

Silicones—Suitable silicones comprise Si—O moieties and may be selected from (a) non-functionalized siloxane polymers, (b) functionalized siloxane polymers, and combinations thereof. The molecular weight of the organosilicone is usually indicated by the reference to the viscosity of the material. In one aspect, the organosilicones may comprise a viscosity of from about 10 to about 2,000,000 centistokes at 25° C. In another aspect, suitable organosilicones may have a viscosity of from about 10 to about 800,000 centistokes at 25° C.

Suitable organosilicones may be linear, branched or cross-linked.

In one aspect, the organosilicone may comprise a cyclic silicone. The cyclic silicone may comprise a cyclomethicone of the formula $[(CH_3)_2SiO]_n$ where n is an integer that may range from about 3 to about 7, or from about 5 to about 6.

In one aspect, the organosilicone may comprise a functionalized siloxane polymer. Functionalized siloxane polymers may comprise one or more functional moieties selected from the group consisting of amino, amido, alkoxy, hydroxy, polyether, carboxy, hydride, mercapto, sulfate, phosphate, and/or quaternary ammonium moieties. These moieties may be attached directly to the siloxane backbone through a bivalent alkylene radical, (i.e., "pendant") or may be part of the backbone. Suitable functionalized siloxane polymers include materials selected from the group consisting of aminosilicones, amidosilicones, silicone polyethers, silicone-urethane polymers, quaternary ABn silicones, amino ABn silicones, and combinations thereof.

In one aspect, the functionalized siloxane polymer may comprise a silicone polyether, also referred to as "dimethicone copolyol." In general, silicone polyethers comprise a polydimethylsiloxane backbone with one or more polyoxyalkylene chains. The polyoxyalkylene moieties may be incorporated in the polymer as pendent chains or as terminal blocks. In another aspect, the functionalized siloxane polymer may comprise an aminosilicone.

In one aspect, the organosilicone may comprise amine ABn silicones and quat ABn silicones. Such organosilicones are generally produced by reacting a diamine with an epoxide.

In another aspect, the functionalized siloxane polymer may comprise silicone-urethanes. These are commercially available from Wacker Silicones under the trade name SLM-21200®.

Perfume: The optional perfume component may comprise a component selected from the group consisting of
  a) a perfume microcapsule, or a moisture-activated perfume microcapsule, comprising a perfume carrier and an encapsulated perfume composition, wherein said perfume carrier may be selected from the group consisting of cyclodextrins, starch microcapsules, porous carrier microcapsules, and mixtures thereof; and wherein said encapsulated perfume composition may comprise low volatile perfume ingredients, high volatile perfume ingredients, and mixtures thereof;
  b) a pro-perfume;
  c) a low odor detection threshold perfume ingredients, wherein said low odor detection threshold perfume ingredients may comprise less than about 25%, by weight of the total neat perfume composition; and
  d) mixtures thereof.

Porous Carrier Microcapsule—A portion of the perfume composition can also be absorbed onto and/or into a porous carrier, such as zeolites or clays, to form perfume porous carrier microcapsules in order to reduce the amount of free perfume in the multiple use fabric conditioning composition.

Pro-perfume—The perfume composition may additionally include a pro-perfume. Pro-perfumes may comprise nonvolatile materials that release or convert to a perfume material as a result of, e.g., simple hydrolysis, or may be pH-change-triggered pro-perfumes (e.g. triggered by a pH drop) or may be enzymatically releasable pro-perfumes, or light-triggered pro-perfumes. The pro-perfumes may exhibit varying release rates depending upon the pro-perfume chosen.

Fabric Hueing Agents—The composition may comprise a fabric hueing agent (sometimes referred to as shading, bluing or whitening agents). Typically the hueing agent provides a blue or violet shade to fabric. Hueing agents can be used either alone or in combination to create a specific shade of hueing and/or to shade different fabric types. This may be provided for example by mixing a red and green-blue dye to yield a blue or violet shade. Hueing agents may be selected from any known chemical class of dyes, including but not limited to acridine, anthraquinone (including polycyclic quinones), azine, azo (e.g., monoazo, disazo, trisazo, tetrakisazo, polyazo), including premetallized azo, benzodifurane and benzodifuranone, carotenoid, coumarin, cyanine, diazahemicyanine, diphenylmethane, formazan, hemicyanine, indigoids, methane, naphthalimides, naphthoquinone, nitro and nitroso, oxazine, phthalocyanine, pyrazoles, stilbene, styryl, triarylmethane, triphenylmethane, xanthenes and mixtures thereof.

Suitable fabric hueing agents include dyes, dye-clay conjugates, and organic and inorganic pigments. Suitable dyes include small molecule dyes and polymeric dyes. Suitable small molecule dyes include small molecule dyes selected from the group consisting of dyes falling into the Colour Index (C.I.) classifications of Acid, Direct, Basic, Reactive or hydrolysed Reactive, Solvent or Disperse dyes for example that are classified as Blue, Violet, Red, Green or Black, and provide the desired shade either alone or in combination. In another aspect, suitable small molecule dyes include small molecule dyes selected from the group consisting of Colour Index (Society of Dyers and Colourists, Bradford, UK) numbers Direct Violet dyes such as 9, 35, 48, 51, 66, and 99, Direct Blue dyes such as 1, 71, 80 and 279, Acid Red dyes such as 17, 73, 52, 88 and 150, Acid Violet dyes such as 15, 17, 24, 43, 49 and 50, Acid Blue dyes such as 15, 17, 25, 29, 40, 45, 75, 80, 83, 90 and 113, Acid Black dyes such as 1, Basic Violet dyes such as 1, 3, 4, 10 and 35, Basic Blue dyes such as 3, 16, 22, 47, 66, 75 and 159, Disperse or Solvent dyes U.S. Pat. No. 8,268,016 B2, or dyes as disclosed in U.S. Pat. No. 7,208,459 B2, and mixtures thereof. In another aspect, suitable small molecule dyes include small molecule dyes selected from the group consisting of C. I. numbers Acid Violet 17, Acid Blue 80, Acid Violet 50, Direct Blue 71, Direct Violet 51, Direct Blue 1, Acid Red 88, Acid Red 150, Acid Blue 29, Acid Blue 113 or mixtures thereof.

Suitable polymeric dyes include polymeric dyes selected from the group consisting of polymers containing covalently bound (sometimes referred to as conjugated) chromogens, (dye-polymer conjugates), for example polymers with chromogens co-polymerized into the backbone of the polymer and mixtures thereof. Polymeric dyes include those described in U.S. Pat. No. 7,686,892 B2.

In another aspect, suitable polymeric dyes include polymeric dyes selected from the group consisting of fabric-substantive colorants sold under the name of Liquitint® (Milliken, Spartanburg, S.C., USA), dye-polymer conjugates formed from at least one reactive dye and a polymer selected from the group consisting of polymers comprising a moiety selected from the group consisting of a hydroxyl moiety, a primary amine moiety, a secondary amine moiety, a thiol moiety and mixtures thereof. In still another aspect, suitable polymeric dyes include polymeric dyes selected from the group consisting of Liquitint® Violet CT, carboxymethyl cellulose (CMC) covalently bound to a reactive blue, reactive violet or reactive red dye such as CMC conjugated with C.I. Reactive Blue 19, sold by Megazyme, Wicklow, Ireland under the product name AZO-CM-CELLULOSE, product code S-ACMC, alkoxylated triphenyl-methane polymeric colourants, alkoxylated thiophene polymeric colourants, and mixtures thereof.

Suitable dye clay conjugates include dye clay conjugates selected from the group comprising at least one cationic/basic dye and a smectite clay, and mixtures thereof. In another aspect, suitable dye clay conjugates include dye clay conjugates selected from the group consisting of one cationic/basic dye selected from the group consisting of C.I. Basic Yellow 1 through 108, C.I. Basic Orange 1 through 69, C.I. Basic Red 1 through 118, C.I. Basic Violet 1 through 51, C.I. Basic Blue 1 through 164, C.I. Basic Green 1 through 14, C.I. Basic Brown 1 through 23, CI Basic Black 1 through 11, and a clay selected from the group consisting of Montmorillonite clay, Hectorite clay, Saponite clay and mixtures thereof. In still another aspect, suitable dye clay conjugates include dye clay conjugates selected from the group consisting of: Montmorillonite Basic Blue B7 C.I. 42595 conjugate, Montmorillonite Basic Blue B9 C.I. 52015 conjugate, Montmorillonite Basic Violet V3 C.I. 42555 conjugate, Montmorillonite Basic Green G1 C.I. 42040 conjugate, Montmorillonite Basic Red R1 C.I. 45160 conjugate, Montmorillonite C.I. Basic Black 2 conjugate, Hectorite Basic Blue B7 C.I. 42595 conjugate, Hectorite Basic Blue B9 C.I. 52015 conjugate, Hectorite Basic Violet V3 C.I. 42555 conjugate, Hectorite Basic Green G1 C.I. 42040 conjugate, Hectorite Basic Red R1 C.I. 45160 conjugate, Hectorite C.I. Basic Black 2 conjugate, Saponite Basic Blue B7 C.I. 42595 conjugate, Saponite Basic Blue B9 C.I. 52015 conjugate, Saponite Basic Violet V3 C.I. 42555 conjugate, Saponite Basic Green G1 C.I. 42040 conjugate, Saponite Basic Red R1 C.I. 45160 conjugate, Saponite C.I. Basic Black 2 conjugate and mixtures thereof.

The hueing agent may be incorporated into the detergent composition as part of a reaction mixture which is the result of the organic synthesis for a dye molecule, with optional purification step(s). Such reaction mixtures generally comprise the dye molecule itself and in addition may comprise un-reacted starting materials and/or by-products of the organic synthesis route.

Suitable polymeric bluing agents may be alkoxylated. As with all such alkoxylated compounds, the organic synthesis may produce a mixture of molecules having different degrees of alkoxylation. Such mixtures may be used directly to provide the hueing agent, or may undergo a purification step to increase the proportion of the target molecule.

Suitable pigments include pigments selected from the group consisting of flavanthrone, indanthrone, chlorinated indanthrone containing from 1 to 4 chlorine atoms, pyranthrone, dichloropyranthrone, monobromodichloropyranthrone, dibromodichloropyranthrone, tetrabromopyranthrone, perylene-3,4,9,10-tetracarboxylic acid diimide, wherein the imide groups may be unsubstituted or substituted by $C_1$-$C_3$-alkyl or a phenyl or heterocyclic radical, and wherein the phenyl and heterocyclic radicals may additionally carry substituents which do not confer solubility in water, anthrapyrimidinecarboxylic acid amides, violanthrone, isoviolanthrone, dioxazine pigments, copper phthalocyanine which may contain up to 2 chlorine atoms per molecule, polychloro-copper phthalocyanine or polybromochloro-copper phthalocyanine containing up to 14 bromine atoms per molecule and mixtures thereof. In another aspect, suitable pigments include pigments selected from the group consisting of Ultramarine Blue (C.I. Pigment Blue 29), Ultramarine Violet (C.I. Pigment Violet 15), Monastral Blue and mixtures thereof.

The aforementioned fabric hueing agents can be used in combination (any mixture of fabric hueing agents can be used).

Structurants—Useful structurant materials that may be added to adequately suspend the benefit agent containing delivery particles include polysaccharides, for example, gellan gum, waxy maize or dent corn starch, octenyl succinated starches, derivatized starches such as hydroxyethylated or hydroxypropylated starches, carrageenan, guar gum, pectin, xanthan gum, and mixtures thereof; modified celluloses such as hydrolyzed cellulose acetate, hydroxy propyl cellulose, methyl cellulose, and mixtures thereof; modified proteins such as gelatin; hydrogenated and non-hydrogenated polyalkenes, and mixtures thereof; inorganic salts, for example, magnesium chloride, calcium chloride, calcium formate, magnesium formate, aluminum chloride, potassium permanganate, laponite clay, bentonite clay and mixtures thereof; polysaccharides in combination with inorganic salts; quaternized polymeric materials, for example, polyether amines, alkyl trimethyl ammonium chlorides, diester ditallow ammonium chloride; imidazoles; nonionic polymers with a pKa less than 6.0, for example polyethyleneimine, polyethyleneimine ethoxylate; polyurethanes. Such materials can be obtained from CP Kelco Corp. of San Diego, Calif., USA; Degussa AG or Dusseldorf, Germany; BASF AG of Ludwigshafen, Germany; Rhodia Corp. of Cranbury, N.J., USA; Baker Hughes Corp. of Houston, Tex., USA; Hercules Corp. of Wilmington, Del., USA; Agrium Inc. of Calgary, Alberta, Canada, ISP of New Jersey, U.S.A.

Anti-agglomeration agents—Useful anti-agglomeration agent materials include, divalent salts such as magnesium salts, for example, magnesium chloride, magnesium acetate, magnesium phosphate, magnesium formate, magnesium boride, magnesium titanate, magnesium sulfate heptahydrate, calcium salts, for example, calcium chloride, calcium formate, calcium acetate, calcium bromide, trivalent salts, such as aluminum salts, for example, aluminum sulfate, aluminum phosphate, aluminum chloride hydrate and polymers that have the ability to suspend anionic particles such as suspension polymers for example, polyethylene imines, alkoxylated polyethylene imines, polyquaternium-6 and polyquaternium-7.

Coatings—In one aspect of the invention, benefit agent containing delivery particles are manufactured and are subsequently coated with an additional material. Non-limiting examples of coating materials include but are not limited to materials selected from the group consisting of poly(meth) acrylate, poly(ethylene-maleic anhydride), polyamine, wax, polyvinylpyrrolidone, polyvinylpyrrolidone co-polymers, polyvinylpyrrolidone-ethyl acrylate, polyvinylpyrrolidone-vinyl acrylate, polyvinylpyrrolidone methylacrylate, polyvinylpyrrolidone/vinyl acetate, polyvinyl acetal, polyvinyl butyral, polysiloxane, poly(propylene maleic anhydride), maleic anhydride derivatives, co-polymers of maleic anhydride derivatives, polyvinyl alcohol, styrene-butadiene latex, gelatin, gum Arabic, carboxymethyl cellulose, carboxymethyl hydroxyethyl cellulose, hydroxyethyl cellulose, other modified celluloses, sodium alginate, chitosan, casein, pectin, modified starch, polyvinyl acetal, polyvinyl butyral, polyvinyl methyl ether/maleic anhydride, polyvinyl pyrrolidone and its co polymers, poly(vinyl pyrrolidone/methacrylamidopropyl trimethyl ammonium chloride), polyvinylpyrrolidone/vinyl acetate, polyvinyl pyrrolidone/ dimethylaminoethyl methacrylate, polyvinyl amines, polyvinyl formamides, polyallyl amines and copolymers of polyvinyl amines, polyvinyl formamides, and polyallyl amines and mixtures thereof. Such materials can be obtained from CP Kelco Corp. of San Diego, Calif., USA; Degussa AG or Dusseldorf, Germany; BASF AG of Ludwigshafen, Germany; Rhodia Corp. of Cranbury, N.J., USA; Baker Hughes Corp. of Houston, Tex., USA; Hercules Corp. of Wilmington, Del., USA; Agrium Inc. of Calgary, Alberta, Canada, ISP of New Jersey U.S.A.

Formaldehyde scavenger—In one aspect, benefit agent containing delivery particles may be combined with a formaldehyde scavenger. In one aspect, such benefit agent containing delivery particles may comprise the benefit agent containing delivery particles of the present invention. Suitable formaldehyde scavengers include materials selected from the group consisting of sodium bisulfite, melamine, urea, ethylene urea, cysteine, cysteamine, lysine, glycine, serine, carnosine, histidine, glutathione, 3,4-diaminobenzoic acid, allantoin, glycouril, anthranilic acid, methyl anthranilate, methyl 4-aminobenzoate, ethyl acetoacetate, acetoacetamide, malonamide, ascorbic acid, 1,3-dihydroxyacetone dimer, biuret, oxamide, benzoguanamine, pyroglutamic acid, pyrogallol, methyl gallate, ethyl gallate, propyl gallate, triethanol amine, succinamide, thiabendazole, benzotriazol, triazole, indoline, sulfanilic acid, oxamide, sorbitol, glucose, cellulose, poly(vinyl alcohol), partially hydrolyzed poly(vinylformamide), poly(vinyl amine), poly(ethylene imine), poly(oxyalkyleneamine), poly(vinyl alcohol)-co-poly(vinyl amine), poly(4-aminostyrene), poly(1-lysine), chitosan, hexane diol, ethylenediamine-N,N'-bisacetoacetamide, N-(2-ethylhexyl)acetoacetamide, 2-benzoylacetoacetamide, N-(3-phenylpropyl)acetoacetamide, lilial, helional, melonal, triplal, 5,5-dimethyl-1,3-cyclohexanedione, 2,4-dimethyl-3-cyclohexenecarboxaldehyde, 2,2-dimethyl-1,3-dioxan-4,6-dione, 2-pentanone, dibutyl amine, triethylenetetramine, ammonium hydroxide, benzylamine, hydroxycitronellol, cyclohexanone, 2-butanone, pentane dione, dehydroacetic acid, or a mixture thereof. These formaldehyde scavengers may be obtained from Sigma/Aldrich/Fluka of St. Louis, Mo. U.S.A. or PolySciences, Inc. of Warrington, Pa., U.S.A.

Such formaldehyde scavengers are typically combined with a slurry containing said benefit agent containing delivery particle, at a level, based on total slurry weight, of from about 2 wt. % to about 18 wt. %, from about 3.5 wt. % to about 14 wt. % or even from about 5 wt. % to about 13 wt. %.

In one aspect, such formaldehyde scavengers may be combined with a product containing a benefit agent containing delivery particle, said scavengers being combined with said product at a level, based on total product weight, of from about 0.005% to about 0.8%, alternatively from about 0.03% to about 0.5%, alternatively from about 0.065% to about 0.25% of the product formulation.

In another aspect, such formaldehyde scavengers may be combined with a slurry containing said benefit agent containing delivery particle, at a level, based on total slurry weight, of from about 2 wt. % to about 14 wt. %, from about 3.5 wt. % to about 14 wt. % or even from about 5 wt. % to about 14 wt. % and said slurry may be added to a product matrix to which addition an identical or different scavenger may be added at a level, based on total product weight, of from about 0.005% to about 0.5%, alternatively from about 0.01% to about 0.25%, alternatively from about 0.05% to about 0.15% of the product formulation, In one aspect, one or more of the aforementioned formaldehyde scavengers may be combined with a liquid fabric enhancing product containing a benefit agent containing delivery particle at a level, based on total liquid fabric enhancing product weight, of from 0.005% to about 0.8%, alternatively from about 0.03% to about 0.4%, alternatively from about 0.06% to about 0.25% of the product formulation In one aspect, such formaldehyde scavengers may be combined with a consumer product, for example, a liquid laundry detergent product containing a benefit agent containing delivery particle, said scavengers being selected from the group consisting of sodium bisulfite, melamine, urea, ethylene urea, cysteine, cysteamine, lysine, glycine, serine, carnosine, histidine, glutathione, 3,4-diaminobenzoic acid, allantoin, glycouril, anthranilic acid, methyl anthranilate, methyl 4-aminobenzoate, ethyl acetoacetate, acetoacetamide, malonamide, ascorbic acid, 1,3-dihydroxyacetone dimer, biuret, oxamide, benzoguanamine, pyroglutamic acid, pyrogallol, methyl gallate, ethyl gallate, propyl gallate, triethanol amine, succinamide, thiabendazole, benzotriazol, triazole, indoline, sulfanilic acid, oxamide, sorbitol, glucose, cellulose, poly(vinyl alcohol), partially hydrolyzed poly(vinylformamide), poly(vinyl amine), poly(ethylene imine), poly(oxyalkyleneamine), poly(vinyl alcohol)-co-poly(vinyl amine), poly(4-aminostyrene), poly(1-lysine), chitosan, hexane diol, ethylenediamine-N,N'-bisacetoacetamide, N-(2-ethylhexyl)acetoacetamide, 2-benzoylacetoacetamide, N-(3-phenylpropyl)acetoacetamide, lilial, helional, melonal, triplal, 5,5-dimethyl-1,3-cyclohexanedione, 2,4-dimethyl-3-cyclohexenecarboxaldehyde, 2,2-dimethyl-1,3-dioxan-4,6-dione, 2-pentanone, dibutyl amine, triethylenetetramine, ammonium hydroxide, benzylamine, hydroxycitronellol, cyclohexanone, 2-butanone, pentane dione, dehydroacetic acid and mixtures thereof, and combined with said liquid laundry detergent product at a level, based on total liquid laundry detergent product weight, of from about 0.003 wt. % to about 0.20 wt. %, from about 0.03 wt. % to about 0.20 wt. % or even from about 0.06 wt. % to about 0.14 wt. %.

In one aspect, such formaldehyde scavengers may be combined with a hair conditioning product containing a benefit agent containing delivery particle, at a level, based on total hair conditioning product weight, of from about 0.003 wt. % to about 0.30 wt. %, from about 0.03 wt. % to about 0.20 wt. % or even from about 0.06 wt. % to about 0.14 wt. %, said selection of scavengers being identical to the list of scavengers in the previous paragraph relating to a liquid laundry detergent product.

Method of Use and Treated Situs

Compositions containing the benefit agent delivery particle disclosed herein can be used to clean or treat a situs inter alia a surface or fabric. Typically at least a portion of the situs is contacted with an embodiment of Applicants' composition, in neat form or diluted in a liquor, for example, a wash liquor and then the situs may be optionally washed and/or rinsed In one aspect, a method of treating and/or cleaning a situs, said method comprising
  a) optionally washing and/or rinsing said situs;
  b) contacting said situs with a composition according to Claims 1 through 26;
  c) optionally washing and/or rinsing said situs; and
  d) optionally dried by drying passively and/or via an active methods such as a laundry dryer.

For purposes of the present invention, washing includes but is not limited to, scrubbing, and mechanical agitation. The fabric may comprise most any fabric capable of being laundered or treated in normal consumer use conditions. Liquors that may comprise the disclosed compositions may have a pH of from about 3 to about 11.5. Such compositions are typically employed at concentrations of from about 500 ppm to about 15,000 ppm in solution. When the wash solvent is water, the water temperature typically ranges from about 5° C. to about 90° C. and, when the situs comprises a fabric, the water to fabric ratio is typically from about 1:1 to about 30:1.

In one aspect, a situs treated with any embodiment of any composition disclosed herein is disclosed.

Test Methods

It is understood that the test methods that are disclosed in the Test Methods Section of the present application should be used to determine the respective values of the parameters of Applicants' invention as such invention is described and claimed herein.

Extraction of Benefit Agent Delivery Particles from Finished Products.

Except where otherwise specified herein, the preferred method to isolate benefit agent delivery particles from finished products is based on the fact that the density of most such particles is different from that of water. The finished product is mixed with water in order to dilute and/or release the particles. The diluted product suspension is centrifuged to speed up the separation of the particles. Such particles tend to float or sink in the diluted solution/dispersion of the finished product. Using a pipette or spatula, the top and bottom layers of this suspension are removed, and undergo further rounds of dilution and centrifugation to separate and enrich the particles. The particles are observed using an optical microscope equipped with crossed-polarized filters or differential interference contrast (DIC), at total magnifications of 100× and 400×. The microscopic observations provide an initial indication of the presence, size, quality and aggregation of the delivery particles.

For extraction of delivery particles from a liquid fabric enhancer finished product conduct the following procedure:
1. Place three aliquots of approximately 20 ml of liquid fabric enhancer into three separate 50 ml centrifuge tubes and dilute each aliquot 1:1 with DI water (eg 20 ml fabric enhancer+20 ml DI water), mix each aliquot well and centrifuge each aliquot for 30 minutes at approximately 10000×g.
2. After centrifuging per Step 1, discard the bottom water layer (around 10 ml) in each 50 ml centrifuge tube then add 10 ml of DI water to each 50 ml centrifuge tube.
3. For each aliquot, repeat the process of centrifuging, removing the bottom water layer and then adding 10 ml of DI water to each 50 ml centrifuge tube two additional times.
4. Remove the top layer with a spatula or a pipette, and
5. Transfer this top layer into a 1.8 ml centrifuge tube and centrifuge for 5 minutes at approximately 20000×g.
6. Remove the top layer with a spatula and transfer into a new 1.8 ml centrifuge tube and add DI water until the tube is completely filled, then centrifuge for 5 minutes at approximately 20000×g.
7. Remove the bottom layer with a fine pipette and add DI water until tube is completely filled and centrifuge for 5 minutes at approximately 20000×g.
8. Repeat step 7 for an additional 5 times (6 times in total).

If both a top layer and a bottom layer of enriched particles appear in the above described step 1, then, immediately move to step 3 (i.e., omit step 2) and proceed steps with steps 4 through 8. Once those steps have been completed, also remove the bottom layer from the 50 ml centrifuge tube from step 1, using a spatula or/and a pipette. Transfer the bottom layer into a 1.8 ml centrifuge tube and centrifuge 5 min at approximately 20000×g. Remove the bottom layer in a new tube and add DI water until the tube is completely filled then centrifuge for 5 minutes approximately 20000×g. Remove the top layer (water) and add DI water again until the tube is full. Repeat this another 5 times (6 times in total). Recombine the particle enriched and isolated top and bottom layers back together.

If the fabric enhancer has a white color or is difficult to distinguish the particle enriched layers add 4 drops of dye (such as Liquitint Blue JH 5% premix from Milliken & Company, Spartanburg, S.C., USA) into the centrifuge tube of step 1 and proceed with the isolation as described.

For extraction of delivery particles from solid finished products which disperse readily in water, mix 1 L of DI water with 20 g of the finished product (eg. detergent foams, films, gels and granules; or water-soluble polymers; soap flakes and soap bars; and other readily water-soluble matrices such as salts, sugars, clays, and starches). When extracting particles from finished products which do not disperse readily in water, such as waxes, dryer sheets, dryer bars, and greasy materials, it may be necessary to add detergents, agitation, and/or gently heat the product and diluent in order to release the particles from the matrix. The use of organic solvents or drying out of the particles should be avoided during the extraction steps as these actions may damage the delivery particles during this phase.

For extraction of delivery particles from liquid finished products which are not fabric softeners or fabric enhancers (eg., liquid laundry detergents, liquid dish washing detergents, liquid hand soaps, lotions, shampoos, conditioners, and hair dyes), mix 20 ml of finished product with 20 ml of DI water. If necessary, NaCl (eg., 100-200 g NaCl) can be added to the diluted suspension in order to increase the density of the solution and facilitate the particles floating to the top layer. If the product has a white color which makes it difficult to distinguish the layers of particles formed during centrifugation, a water-soluble dye can be added to the diluent to provide visual contrast.

The water and product mixture is subjected to sequential rounds of centrifugation, involving removal of the top and bottom layers, re-suspension of those layers in new diluent, followed by further centrifugation, isolation and re-suspension. Each round of centrifugation occurs in tubes of 1.5 to 50 ml in volume, using centrifugal forces of up to 20,000×g, for periods of 5 to 30 minutes. At least six rounds of centrifugation are typically needed to extract and clean sufficient particles for testing. For example, the initial round of centrifugation may be conducted in 50 ml tubes spun at 10,000×g for 30 mins, followed by five more rounds of centrifugation where the material from the top and bottom layers is resuspended separately in fresh diluent in 1.8 ml tubes and spun at 20,000×g for 5 mins per round.

If delivery particles are observed microscopically in both the top and bottom layers, then the particles from these two layers are recombined after the final centrifugation step, to create a single sample containing all the delivery particles extracted from that product. The extracted particles should be analyzed as soon as possible but may be stored as a suspension in DI water for up to 14 days before they are analyzed.

One skilled in the art will recognize that various other protocols may be constructed for the extraction and isolation of delivery particles from finished products, and will recognize that such methods require validation via a comparison of the resulting measured values, as measured before and after the particles' addition to and extraction from finished product.

Fracture Strength

To calculate the percentage of delivery particles which fall within a claimed range of fracture strengths, three different measurements are made and two resulting graphs are utilized. The three separate measurements required are namely: i) the volume-weighted particle size distribution (PSD); ii) the diameter of 10 individual particles within each of 3 specified size ranges, and; iii) the rupture-force of those same 30 individual particles. The two graphs created are namely: a plot of the volume-weighted particle size distribution data collected at i) above; and a plot of the modeled distribution of the relationship between particle diameter and fracture-strength, derived from the data collected at ii) and iii) above. The modeled relationship plot enables the particles within a claimed strength range to be identified as a specific region under the volume-weighted PSD curve, and then calculated as a percentage of the total area under the curve.

a) The volume-weighted particle size distribution (PSD) is determined via single-particle optical sensing (SPOS), also called optical particle counting (OPC), using the AccuSizer 780 AD instrument and the accompanying software CW788 version 1.82 (Particle Sizing Systems, Santa Barbara, Calif., U.S.A.). The instrument is configured with the following conditions and selections: Flow Rate=1 ml/sec; Lower Size Threshold=0.50 μm; Sensor Model Number=LE400-05SE; Autodilution=On; Collection time=120 sec; Number channels=512; Vessel fluid volume=50 ml; Max coincidence=9200. The measurement is initiated by putting the sensor into a cold state by flushing with water until background counts are less than 100. A sample of delivery particles in suspension is introduced, and its density of particles adjusted with DI water as necessary via autodilution to result in particle counts of at least 9200 per ml. During a time period of 120 seconds the suspension is analyzed. The resulting volume-weighted PSD data are plotted and recorded, and the values of the mean, $5^{th}$ percentile, and $90^{th}$ percentile are determined.

b) The diameter and the rupture-force value (also known as the bursting-force value) of individual particles are measured via a computer-controlled micromanipulation instrument system which possesses lenses and cameras able to image the delivery particles, and which possess a fine, flat-ended probe connected to a force-transducer (such as the Model 403A available from Aurora Scientific Inc, Canada), as described in: Zhang, Z. et al. (1999) "Mechanical strength of single microcapsules determined by a novel micromanipulation technique." *J. Microencapsulation*, vol 16, no. 1, pages 117-124, and in: Sun, G. and Zhang, Z. (2001) "Mechanical Properties of Melamine-Formaldehyde microcapsules." *J. Microencapsulation*, vol 18, no. 5, pages 593-602, and as available at the University of Birmingham, Edgbaston, Birmingham, UK.

c) A drop of the delivery particle suspension is placed onto a glass microscope slide, and dried under ambient conditions for several minutes to remove the water and achieve a sparse, single layer of solitary particles on the dry slide. Adjust the concentration of particles in the suspension as needed to achieve a suitable particle density on the slide. More than one slide preparation may be needed.

d) The slide is then placed on a sample-holding stage of the micromanipulation instrument. Thirty benefit delivery particles on the slide(s) are selected for measurement, such that there are ten particles selected within each of three pre-determined size bands. Each size band refers to the diameter of the particles as derived from the Accusizer-generated volume-weighted PSD. The three size bands of particles are: the Mean Diameter +/-2 μm; the $5^{th}$ Percentile Diameter +/-2 μm; and the $90^{th}$ Percentile Diameter +/-2 μm. Particles which appear deflated, leaking or damaged are excluded from the selection process and are not measured.

e) For each of the 30 selected particles, the diameter of the particle is measured from the image on the micromanipulator and recorded. That same particle is then compressed between two flat surfaces, namely the flat-ended force probe and the glass microscope slide, at a speed of 2 μm per second, until the particle is ruptured. During the compression step, the probe force is continuously measured and recorded by the data acquisition system of the micromanipulation instrument.

f) The cross-sectional area is calculated for each of the selected particles, using the diameter measured and assuming a spherical particle ($\pi r^2$, where r is the radius of the particle before compression). The rupture force is determined for each selected particle from the recorded force probe measurements, as demonstrated in Zhang, Z. et al. (1999) "Mechanical strength of single microcapsules determined by a novel micromanipulation technique." *J. Microencapsulation*, vol 16, no. 1, pages 117-124, and in: Sun, G. and Zhang, Z. (2001) "Mechanical Properties of Melamine-Formaldehyde microcapsules." *J. Microencapsulation*, vol 18, no. 5, pages 593-602.

g) The Fracture Strength of each of the 30 particles is calculated by dividing the rupture force (in Newtons) by the calculated cross-sectional area of the respective particle.

h) On a plot of particle diameter versus fracture-strength, a Power Regression trend-line is fit against all 30 raw data points, to create a modeled distribution of the relationship between particle diameter and fracture-strength.

i) The percentage of particles which have a fracture strength value within a specific strength range is determined by viewing the modeled relationship plot to locate where the curve intersects the relevant fracture-strength limits, then reading off the particle size limits corresponding with those strength limits. These particle size limits are then located on the volume-weighted PSD plot and thus identify an area under the PSD curve which corresponds to the portion of particles falling within the specified strength range.

j) The identified area under the PSD curve is then calculated as a percentage of the total area under the PSD curve. This percentage indicates the percentage of delivery particles falling with the specified range of fracture strengths.

C log P

The log P values of many perfume ingredients have been reported; for example, the Pomona92 database, available from Daylight Chemical Information Systems, Inc. (Daylight CIS, Irvine, Calif.), contains many, along with citations to the original literature. However, the log P values are most conveniently calculated by the "C LOG P" program, also available from Daylight CIS. This program also lists experimental log P values when they are available in the Pomona92 database. The "calculated log P" (C log P) is determined by the fragment approach of Hansch and Leo (cf., A. Leo, in Comprehensive Medicinal Chemistry, Vol. 4, C. Hansch, P. G. Sammens, J. B. Taylor and C. A. Ramsden, Eds., p. 295, Pergamon Press, 1990, incorporated herein by reference). The fragment approach is based on the chemical structure of each perfume ingredient, and takes into account the numbers and types of atoms, the atom connectivity, and chemical bonding. The C log P values, which are the most reliable and widely used estimates for this physicochemical property, are preferably used instead of the experimental log P values in the selection of perfume ingredients which are useful in the present invention.

Boiling Point

The boiling point of perfume ingredients is measured according to standard test method ASTM D2887-04a, "Standard Test Method for Boiling Range Distribution of Petroleum Fractions by Gas Chromatography," (ASTM International, West Conshohocken, Pa., USA. Section 5.2 of that method notes: "Boiling range distributions obtained by this test method are essentially equivalent to those obtained by true boiling point (TBP) distillation (see Test Method D 2892). They are not equivalent to results from low efficiency distillations such as those obtained with Test Method D 86 or D 1160."

Particle Size (Diameter):

A drop of the particle suspension or finished product is placed onto a glass microscope slide and dried under ambient conditions for several minutes to remove the water and achieve a sparse, single layer of solitary particles on the dry slide. Adjust the concentration of particles in the suspension as needed to achieve a suitable particle density on the slide. The slide is placed on a sample stage of an optical microscope equipped and examined at a total magnification of 100× or 400×. Images are captured and calibrated for the accurate measurement of particle diameters. Three replicate slides are prepared and analyzed.

For particle size measurement, at least 50 benefit agent delivery particles on each slide are selected for measurement, in a manner which is unbiased by their size and so creates a representative sample of the distribution of particle sizes present. This may be achieved by examining fields-of-view which are selected at random or according to a pre-defined grid pattern, and by measuring the diameter of all the delivery particles present in each field-of-view examined. Delivery particles which appear obviously non-spherical, deflated, leaking, or damaged are unsuitable for measurement, are excluded from the selection process and their diameters are not recorded. The diameter of each suitable delivery particle examined is measured using the microscope and the value is recorded. The recorded particle diameter measurements are used to calculate the percentage of the particles having a particle size within the claimed size range(s), and also to calculate the mean particle size.

Particle Wall Thickness

The particle wall thickness is measured in nanometers on 50 benefit agent delivery particles using freeze-fracture cryo-scanning electron microscopy (FF cryoSEM), at magnifications of between 50,000× and 150,000×. Samples are prepared by flash freezing small volumes of a suspension of particles or finished product. Flash freezing can be achieved by plunging into liquid ethane, or through the use of a device such as a High Pressure Freezer Model 706802 EM Pact, (Leica Microsystems, Wetzlar, Germany). Frozen samples are fractured while at −120° C., then cooled to below −160° C. and lightly sputter-coated with gold/palladium. These steps can be achieved using cryo preparation devices such as those from Gatan Inc., (Pleasanton, Calif., USA). The frozen, fractured and coated sample is then transferred at −170° C. or lower, to a suitable cryoSEM microscope, such as the Hitachi S-5200 SEM/STEM (Hitachi High Technologies, Tokyo, Japan). In the Hitachi S-5200, imaging is performed with 3.0 KV accelerating voltage and 5 µA-20 µA tip emission current.

Images are acquired of the fractured wall in cross-sectional view from 50 benefit delivery particles selected in a random manner which is unbiased by their size, so as to create a representative sample of the distribution of particle sizes present. The wall thickness of each of the 50 particles is measured using the calibrated microscope software, by drawing a measurement line perpendicular to the outer surface of the particle wall. The 50 independent wall thickness measurements are recorded and used to calculate the mean thickness, and the percentage of the particles having a wall thickness within the claimed range.

Benefit Agent Leakage

The amount of benefit agent leakage from the delivery particles is determined according to the following method:
 a) Obtain two 1 g samples of the raw material slurry of benefit delivery particles.
 b) Add 1 g of the raw material slurry of benefit delivery particles to 99 g of the product matrix in which the particles will be employed, and label the mixture as Sample 1. Immediately use the second 1 g sample of raw material particle slurry in Step d below, in its neat form without contacting product matrix, and label it as Sample 2.
 c) Age the particle-containing product matrix (Sample 1) for 2 weeks at 35° C. in a sealed, glass jar.
 d) Using filtration, recover the particles from both samples. The particles in Sample 1 (in product matrix) are recovered after the aging step. The particles in Sample 2 (neat raw material slurry) are recovered at the same time that the aging step began for sample 1.
 e) Treat the recovered particles with a solvent to extract the benefit agent materials from the particles.
 f) Analyze the solvent containing the extracted benefit agent from each sample, via chromatography. Integrate the resultant benefit agent peak areas under the curve, and sum these areas to determine the total quantity of benefit agent extracted from each sample.
 g) Determine the percentage of benefit agent leakage by calculating the difference in the values obtained for the total quantity of benefit agent extracted from Sample 2 minus Sample 1, expressed as a percentage of the total quantity of benefit agent extracted from Sample 2, as represented in the equation below:

$$\text{Percentage of Benefit Agent Leakage} = \left(\frac{\text{Sample 2} - \text{Sample 1}}{\text{Sample 2}}\right) \times 100$$

Viscosity

Viscosity of liquid finished product is measured using an AR 550 rheometer/viscometer from TA instruments (New Castle, Del., USA), using parallel steel plates of 40 mm diameter and a gap size of 500 µm. The high shear viscosity at 20 s$^{-1}$ and low shear viscosity at 0.05 s$^{-1}$ is obtained from a logarithmic shear rate sweep from 0.1 s$^{-1}$ to 25 s$^{-1}$ in 3 minutes time at 21° C.

Free Formaldehyde

Free formaldehyde in finished product is measured in accordance with the standard method NIOSH 5700 Formaldehyde on Dust (NIOSH Manual of Analytical Methods, Fourth Edition, August 1994, The National Institute for Occupational Safety and Health, Centers for Disease Control and Prevention, Atlanta, Ga., USA), with the following adaptations:
 Adaptation of DNPH concentration: minimize polymer degradation during derivatization reaction and create condition to monitor fate of derivatization reagent during subsequent LC analysis (check for potential reagent consumption by other sample constituents such as perfume carbonyls).
 Reduction of the acid concentration and use of hydrochloric acid instead of perchloric acid: create milder conditions for derivatization, avoiding excessive polymer/resin degradation. (Derivatization kinetics at these conditions are checked to show reaction plateau is reached at about 10 min)

Solvent extraction (Acetonitrile): ensures fast separation of the solid material from samples and allowing for easy filtration. The filtrate contains formaldehyde for analysis. Standard calibration solutions are made up to match the solvent composition to that of samples analyzed to ensure equal reaction conditions for derivatization.

Apparatus
1) Waters HPLC instrumentation and Millennium system control and data acquisition system.
2) Continuous flow eluent vacuum degassing unit (Erma ERC-3612 or equivalent. Alternatively use He sparging)
3) Solvent delivery module (Waters 600E or equivalent multiple channel solvent delivery system)
4) Variable volume injector (Waters 717 plus, automatic injector or equivalent)
5) Analytical HPLC column/guard column (Symmetry C8, 3.9×1 50 mm, WAT no 054235 with guard column WAT no 054250 or equivalent)
6) UV detector (Waters 996 Photo Diode Array Detector or equivalent)
7) Data station (Waters Millennium 2010, 2020 C/S, or an equivalent system capable of storing and processing data).
8) Disposable filter units (0.45 μm, PTFE or 0.45 μm 25 mm, for sample filtration. Millipore Millex HV, cat. no. SLSR025NS)
9) Disposable syringes (Polypropylene 2 mL, with Luer fitting. Must match filtration unit female Luer.
10) Disposable glass sample vials, 4 mL, with caps. (Waters 4 mL clear glass vials with caps No. WAT025051, or equivalent)
11) Disposable filter cups, 0.45 μm, for eluent filtration. Millipore, cat no. SJHVM4710, or equivalent.
12) Lab Shaker+Lab Therm (Applitek Scientific Instruments or equivalent)
13) Titration equipment consisting of:
    a) Automatic titrator (Mettler DL70 or equivalent)
    b) Platinum electrode (Mettler DM140-Sc or equivalent)
    c) Titration vessel (100 mL, fitting DL70 or an equivalent automatic titrator system)

Reagents/Solvents
1) HPLC grade water (Resistivity above 18 M:cm, free from organic material.
2) Acetonitrile (HPLC Ultra Gradient Grade, J. T. Baker, no. 9017 or equivalent)
3) Ion Pair Reagent: tetrabutylammonium hydrogen sulfate Pic reagent A Low UV, Waters no. WAT084189 or equivalent
4) 2,4-dinitrophenylhydrazine ($C_6H_6N_4O_4$) Aldrich no 19,930-3 or equivalent
5) Formaldehyde 37 wt. % in water, used as standard material. Aldrich, no 25,254-9 or equivalent
6) Ethanol absolute (J. T. Baker, no. 8006 or equivalent)
7) Hydrochloric acid 36-38% (J. T. Baker, no 6081 or equivalent)
8) Iodine, volumetric standard, 0.1N solution in water Aldrich, no 31,898-1 or equivalent
9) Sodium hydroxide, 1N (Aldrich, no 31,951-1 or equivalent)
10) Hydrochloric acid, 1N (Aldrich, no 31,894-9 or equivalent)
11) Sodium thiosulphate, volumetric standard, 0.1N solution in water Aldrich, no 31,954-6 or equivalent Solutions
1) Eluent A: water/ACN 90:10 with 5 mM Pic. Dissolve one bottle of Pic A Low UV into 900 mL of HPLC grade water. Add, while stirring vigorously, 100 mL of acetonitrile. Filter through a 0.45 μm disposable filter cup.
2) Eluent B: water/ACN 30:70 with 5 mM Pic A. Dissolve one bottle of Pic A Low UV into 300 mL of HPLC grade water. Add very slowly, while stirring vigorously, 700 mL of acetonitrile. Filter through a 0.45 μm disposable filter cup. It is very important to mix well and add the acetonitrile very slowly to prevent the precipitation of the Pic A as much as possible. Preferably, prepare this eluent well in advance to allow equilibration and avoid precipitation during use. Filter before use.
3) 2,4 Dinitrophenylhydrazine stock solution. Weigh, to the nearest 0.01 g, 0.4 g of 2,4-DNPH in a 100 mL glass bottle. Add 20 ml of ethanol absolute and stir vigorously. While stirring, add slowly 16 ml of concentrated hydrochloric acid, followed by 64 ml of ethanol absolute. The 2, 4-DNPH stock solution can be kept for about 2 months.
4) 2,4 Dinitrophenylhydrazine working solution for samples. Pipette 5 mL of the 2,4-dinitrophenylhydrazine stock solution into a 100 mL glass volumetric flask. Fill to volume with de ionized water and mix well. The 2,4-DNPH working solution has to be re-made daily.
5) 2,4 Dinitrophenylhydrazine working solution for standards. Pipette 5 mL of the 2,4-dinitrophenylhydrazine stock solution into a 100 mL glass volumetric flask. Fill to volume with acetonitrile mix well. The 2,4-DNPH working solution has to be re-made daily.

Procedure
1) Formaldehyde standard stock solution: Weigh, to the nearest 0.0001 gram, 1.0 g of formaldehyde standard into a small sample cup. Dissolve into a 1 L volumetric flask using deionized water. Record the weight as Wst
2) Preparation of standard working solutions
    a) Pipette 5 mL of the formaldehyde stock solution into a 50 mL volumetric flask. Bring to volume with de ionized water and mix well.
    b) Pipette 0, 0.5, 1.0, 3, and 5 mL of the diluted stock solution into separate 50 mL volumetric flasks. Bring to volume with de ionized water and mix well. Filter approximately 5 mL of each standard working solution through a 0.45 μm disposable filter unit into a glass vial.
3) Sample preparation: Weigh, to the nearest 0.0001 gram, about 1 gram of sample into a 50 mL volumetric flask. Bring to volume with acetonitrile and mix well. Allow about five (5) minutes for the insoluble material to settle. Filter approximately 5 mL of the sample solution through a 0.45 μm disposable filter unit into a glass vial. Record the exact weight as Wsa in grams.
4) Derivatization procedure
    a) Pipette 1.00 mL of each standard solution, filtered sample solution, and filtered extract into separate 4 mL sample vials. The choice of the calibration range is dependent on the expected free formaldehyde level in sample solutions or extracts.
    b) Standards: add 1.00 mL of 2,4-DNPH working solution for standards to each vial. Stopper and mix.
    c) Samples: add 1.00 mL of 2,4-DNPH working solution for samples to each vial. Stopper and mix.
    d) Let react for 10 minutes±20 seconds before injection. Note: this timing is critical. Start the timer as soon as the reagents are mixed and take into account the time it takes to load and inject a sample.

5) Instrumental Operation: Set up the HPLC system according to the manufacturer's instructions using the following conditions:
Isocratic: 20% A-80% B/0.8 ml/min
Detection: UV at 365 nm
Inj. volume: 20 µl
Runtime: 10 minutes
Calibration
1) Inject 20 µl of a derivatized standard solution at least once to check for proper instrument functioning (Never use the area counts of the first injection for calibration purposes. The first injection after start up of the HPLC system is generally not representative).
2) Inject 20 µl of each of the derivatized standard solutions.
3) Record the peak areas and, with the help of the examples in appendix 9, assign the peak identity.
Analysis of the Samples
1) Inject 20 µl of each of the derivatized sample solutions or extracts.
2) Record the peak area for the formaldehyde peak.
3) After analyses are finished, replace the eluent by de ionized water and then a storage solvent, e.g. HPLC grade methanol, before removing the column from the system.
Calculations
(1) Calculate the amount of formaldehyde in each of the standard solutions (calibration range: 0-5 µg/mL)

$$\text{vol } \mu\text{g formaldehyde/mL} = \frac{Wst \times Ast \times 1000 \times Dil\ vol}{100 \times 10 \times 50} = \frac{Wst \times Ast \times Dil}{50}$$

Where:
Wst=weight of standard in the stock solution in grams (7.1.1)
Ast=Activity of the standard material (%) determined by titration (7.1.5)
Dil vol=diluted standard stock amounts in mL used for preparing standard solutions (0-10 mL)
(2) Construct a calibration curve (amounts versus peak area). When using the Waters Millennium 2010 data processing software, perform the 'Fit Type': Linear calibration setting in 'Component table' of the Processing Method.
(3) Starting from the formaldehyde peak area of a sample, read the amount of formaldehyde in the sample solution or extract in µg/mL from the calibration curve. Record this value as $\mu g_{sa}$. Note: this calculation assumes that injection volumes of standards and samples are identical.
(4) Calculate the amount of formaldehyde in the samples as follows:

$$ppm \text{ formaldehyde} = \frac{\mu gsa \times 100}{Wsa}$$

Where:
µgsa=amount of free formaldehyde in the sample solution in µg/mL (7.3)
Wsa=weight of sample in grams (7.3.1)
Perfume and Perfume Raw Materials (PRMs)
To determine the identity and to quantify the weight of perfume, perfume ingredients, or Perfume Raw Materials (PRMs), encapsulated within the delivery agent particles, Gas Chromatography with Mass Spectroscopy/Flame Ionization Detector (GC-MS/FID) is employed. Suitable equipment includes: Agilent Technologies G1530A GC/FID; Hewlett Packer Mass Selective Device 5973; and 5%-Phenyl-methylpolysiloxane Column J&W DB-5 (30 m length×0.25 mm internal diameter×0.25 µm film thickness). Approximately 3 g of the finished product or suspension of delivery particles, is weighed and the weight recorded, then the sample is diluted with 30 mL of DI water and filtered through a 5.0 µm pore size nitrocellulose filter membrane. Material captured on the filter is solubilized in 5 mL of ISTD solution (25.0 mg/L tetradecane in anhydrous alcohol), and heated at 60° C. for 30 minutes. The cooled solution is filtered through 0.45 µm pore size PTFE syringe filter and analyzed via GC-MS/FID. Three known perfume oils are used as comparison reference standards. Data Analysis involves summing the total area counts minus the ISTD area counts, and calculating an average Response Factor (RF) for the 3 standard perfumes. Then the Response Factor and total area counts for the product encapsulated perfumes are used along with the weight of the sample, to determine the total weight percent for each PRM in the encapsulated perfume. PRMs are identified from the mass spectrometry peaks.
Method for Analysis of Styrene Maleic Anhydride Monomethylmaleate, and or/a Salt Thereof (SMAM) in Benefit Agent Delivery Particles
The objective of the method described herein is to identify and determine the amount of Styrene Maleic Anhydride Monomethylmaleate (SMAM) in delivery particles comprising aminoplast, polyacrylate and/or polymethacrylate wall chemistries. This method assumes that the species of Styrene Maleic Anhydride used in the delivery particle is Styrene Maleic Anhydride Monomethylmaleate, and or/a salt thereof and not a mixture of SMAM with other styrene maleic anhydrides. The benefit agent delivery particles are also referred to as "delivery particle" and/or "delivery particles" in this method. The method consists of extracting delivery particle walls from finished products by filtration, extracting the delivery particle wall materials, and quantifying the amount of SMA using ATR-FTIR Spectroscopy.
1. All solvents used are of HPLC reagent grade, and water is filter-sterilized, deionized water. Weigh approximately 2 grams of the sample to be tested into an appropriately sized tri-pour beaker. Dilute with 5 mL DI water and mix well. Add 20 mL of isopropyl alcohol (IPA). Add 20 mL of hexane and mix briefly. Use a 60 mL syringe housing to filter the sample through a polycarbonate, hydrophilic screen filter having a 1.2 µm pore size and 25 mm diameter (Millipore Isopore Membrane), via a filter mounting assembly (eg. Swinnex) attached to a vacuum manifold. Rinse the filter several times with hexane and/or IPA.
2. Repeat step 1 at least ten times to isolate enough delivery particles.
3. Carefully remove the filters and transfer all of them into a 50 mL centrifuge tube.
4. Add 5-15 mL of methanol, IPA, hexane or a mixture thereof to the tube. The tube may also be heated for 30 minutes at 60° C. to help remove perfumes.
5. Place the tube in an ultrasonic cleaning bath for at least 5 minutes, preferably longer, to remove the particles from the filter. Remove the filters from the tube with tweezers.
6. Centrifuge the tube for at least 5 minutes at a minimum of 5000 rpm. If multiple layers are formed, confirm the presence of delivery particles via light microscopy by sampling a small amount from each layer. Separate the layer(s) containing delivery particles from the solution via decantation or with a transfer pipette.
7. Suspend the fraction containing delivery particles in DI water, shake the tube and centrifuge again. Separate the solution from the solids via decantation or with a transfer pipette. Add a few mL of DI water to the solids, shake and freeze using liquid nitrogen. Freeze-dry the sample until complete dryness is achieved (at least 24 hours).
8. Using a Perkin Elmer Spectrum Two FTIR spectrometer equipped with DTGS detector and Perkin Elmer diamond ATR accessory (Perkin-Elmer, Waltham Mass., USA), collect an ATR-FTIR spectrum of a small amount of the extracted delivery particle wall material. Identify the wall chemistry as melamine or polyacrylate by comparing with a melamine standard and a polyacrylate standard, FTIR library search or literature reference. FTIR spectra are collected using at least 8 co-added scans at a resolution of 4 cm$^{-1}$. Melamine chemistry is identified by the characteristic melamine peak at 815-810 cm$^{-1}$, together with peaks at approximately 1550 cm$^{-1}$, 1490 cm$^{-1}$, 1340 cm$^{-1}$, 1160 cm$^{-1}$ and 1017 cm$^{-1}$. Polyacrylate chemistry is identified by the characteristic acrylate carbonyl peak at 1735-1725 cm$^{-1}$, together with peaks at approximately 1456 cm$^{-1}$, 1407 cm$^{-1}$, 1160 cm$^{-1}$, 1061 cm$^{-1}$, 809 cm$^{-1}$ and 759 cm$^{-1}$.
9. Add 10-15 mL of methanol, hexane or IPA to the centrifuge tube that contains the freeze-dried particle wall material from step 7. Shake and sonicate for at least 10 minutes. Centrifuge for at least 5 minutes at a minimum of 5000 rpm. Decant the solvent. Repeat this step at least twice.
10. Repeat step 7.
11. Collect an ATR-FTIR spectrum of the extracted particle wall material. Compare the 720-690 cm$^{-1}$ IR region with the same region of the IR spectrum collected in step 8 if wall is melamine or compare with the 1800-650 cm$^{-1}$ region if wall is polyacrylate
    11.1 If no differences are observed and the SMAM peak at 700±3 cm$^{-1}$ is still observed then proceed to steps 12-20 for the SMAM analysis in melamine delivery particles, or to steps 21-29 for the SMAM analysis in polyacrylate delivery particles.
    11.2 For melamine particles, if changes occurred in this region, for instance, a peak at 700±3 cm$^{-1}$ was observed in step 8 and its intensity decreased in step 11, then repeat steps 9 to 11 until no changes in the 720-690 cm$^{-1}$ IR region are observed. If the peak at 700±3 cm$^{-1}$ ultimately disappears while the melamine peak at 815-810 cm$^{-1}$ remains present, then no SMAM quantification is needed.
    11.3 For polyacrylate wall particles, if changes occurred in this region, for instance, a peak at 700±3 cm$^{-1}$ was observed in step 8 and its intensity decreased in step 11, then repeat steps 9 to 11 until no changes in the 1800-650 cm$^{-1}$ IR region are observed. If the peak at 700±3 cm$^{-1}$ ultimately disappears while the polyacrylate peak at 1735-1725 cm$^{-1}$ remains present, then no SMAM quantification is needed.

SMAM quantification analysis in Melamine delivery particles:
12. Obtain a reference standard solution of styrene maleic anhydric salt copolymer in basic solution with NaOH, (as supplied by Ashland Water Technologies/Ashland Inc., Covington, Ky., USA), wherein the: percentage of solids is 13%; MW is 350,000; Monomer ratio is 1:1; pH is 7.5-9.0; pKa is at pH 1.83 and at pH 6.07; and the Viscosity at 25° C. is 200-700 cps. This styrene maleic acid anhydride (SMAM) polymer solution is frozen in liquid nitrogen and converted to solid powder by freeze drying. To about 0.5-1 mg of particle wall material, and using antistatic micro disposable laboratory spatulas, spike in known amounts of freeze dried SMAM polymer in 1.5 mL centrifuge tubes. At least two SMAM spike levels should be prepared. As example, level 1 can be 0.50 mg of particle wall material+0.50 mg solid SMAM and level 2 can be 0.50 mg of particle wall material+1.00 mg solid SMAM. Record the weights of wall material and SMAM to ±0.01 mg.
13. Vortex the sample mixtures for at least 1 minute, preferably for longer.
14. Place a small amount of particle wall material with no SMAM added into the ATR crystal, press against the crystal, and collect the ATR-FTIR spectrum. This will correspond to Level 0.
15. Collect spectra for Level 1 and 2 (and other levels if necessary).
16. Repeat steps 14 and 15 at least two times more.
17. Using a software capable of IR data analysis, determine the integrated peak area of the melamine peak at 813 cm$^{-1}$±3 cm$^{-1}$ and the SMAM peak at 700 cm$^{-1}$±3 cm$^{-1}$ after drawing a baseline at their peak bases. For each Level calculate the average of the integrated peak area ratio 700/813.

$$700/813 \text{ peak area ratio} = \frac{700 \text{ cm}^{-1} \text{ integrated peak area}}{813 \text{ cm}^{-1} \text{ integrated peak area}}$$

18. Plot the values of 700/813 peak area ratios versus their corresponding weight ratio of SMAM to delivery particle wall.

$$\text{Weight ratio of SMAM to delivery particle wall} = \frac{\text{weight (g) SMAM added to sample}}{\text{weight (g) particle wall}}$$

19. Fit the curve with a linear regression and obtain its equation (i.e. slope and y-intercept).
20. The amount of SMAM per gram of delivery particle wall in w/w % is calculated from the x-axis intercept of the linear regression and is reported as follows:

$$\text{g SMAM/g delivery particle wall}\left(\frac{w}{w}\%\right) = \frac{\text{intercept}}{\text{slope}} \times 100$$

SMAM quantification analysis in Polyacrylate delivery particles:
21. "Obtain a reference standard solution of styrene maleic anhydric salt copolymer in basic solution with NaOH, (as supplied by Ashland Water Technologies/Ashland Inc., Covington, Ky., USA), wherein the: percentage of solids is 13%; MW is 350,000; Monomer ratio is 1:1; pH is 7.5-9.0; pKa is at pH 1.83 and at pH 6.07; and the Viscosity at 25° C. is 200-700 cps. This styrene maleic acid anhydride (SMAM) polymer solution is frozen in liquid nitrogen and converted to solid powder by freeze drying. To about 0.5-1 mg of wall material, and using antistatic micro disposable laboratory spatulas, spike in known amounts of freeze dried SMAM polymer in 1.5 mL eppendorf tubes. At least two SMAM spike levels should be prepared. As example, level 1 can be 0.50 mg of PMC wall material+0.50 mg solid SMAM and level 2 can be 0.50 mg of PMC wall material+1.00 mg solid SMAM. Record the weights of wall material and SMAM to ±0.01 mg.

22. Vortex the sample mixtures for at least 1 minute, preferably for longer.
23. Place a small amount of PMC wall material with no SMAM added into the ATR crystal, press against the crystal, and collect the ATR-FTIR spectrum. This will correspond to Level 0.
24. Collect spectra for Level 1 and 2 (and other levels if necessary).
25. Repeat steps 23 and 24 at least two times more.
26. Using a software capable of IR data analysis, determine the integrated peak area of the poalyacrylate peak at 1732 cm$^{-1}$±5 cm$^{-1}$ and the SMAM peak at 700 cm$^{-1}$±3 cm$^{-1}$ after drawing a baseline at their peak bases. For each Level calculate the average of the integrated peak absorbance ratio 700/1732.

$$700/1732 \text{ peak area ratio} = \frac{700 \text{ cm}^{-1} \text{ integrated peak area}}{1732 \text{ cm}^{-1} \text{ integrated peak area}}$$

27. Plot the values of 700/1732 peak area ratios versus their corresponding weight ratio of SMAM to delivery particle wall.

Weight ratio of SMAM to delivery particle wall =

$$\frac{\text{weight (g) SMAM added to sample}}{\text{weight (g) particle wall}}$$

weight (g) SMAM added to sample

28. Fit the curve with a linear regression and obtain its equation (i.e. slope and y-intercept).
29. The amount of SMAM per gram of PMC wall is calculated from the x-axis intercept of the linear regression and is reported as follows:

$$g \text{ SMAM}/g \text{ delivery particle wall}\left(\frac{w}{w}\%\right) = \frac{\text{intercept}}{\text{slope}} \times 100$$

Method for Analysis of Styrene Maleic Anhydride Monomethylmaleate, and or/a Salt Thereof (SMAM) Hydrolysis Degree For purpose of this application, Hydrolysis Degree is the determined as follows:

The raw material SMA polymer is analyzed via Fourier-Transformed Infra-Red Spectroscopy (FTIR), after removing all liquid via freeze-drying. Approximately 50 mg of the freeze-dried material may then be re-dissolved in 2 mL methanol in order to cast a thin film using approximately 200 µL of the solution cast over a polyethylene sample IR card. The solution is allowed to air dry for 30 minutes prior to FTIR analysis. The anhydride and the acid (hydrolyzed) unit are each quantified from the peak absorbance present at their respective characteristic absorption bands in the FTIR spectra, namely: 1770-1790 cm$^1$ for anhydride, and 1700-1720 cm$^1$ for COOH acid (hydrolyzed polymer). The IR spectrum (from 4000 cm$^{-1}$ to 500 cm$^{-1}$ at a resolution of 4 cm$^{-1}$) is recorded using a plain uncoated polyethylene sample IR card as the background.

The percent hydrolysis of the polymer is determined by calculating the ratio of the peak absorbances of the acid units, to the sum of the acid units and anhydride units, and via the following equation:

Percent Hydrolysis=(maleic acid/(maleic acid+maleic anhydride))×100

Wherein the terms "maleic acid" and "maleic anhydride" represent the peak absorbance of each polymer unit respectively, as determined by quantitative Fourier-Transformed Infra-Red Spectroscopy (FTIR) using the characteristic absorption bands of: 1770-1790 cm$^1$ for anhydride, and 1700-1720 cm$^1$ for COOH acid (hydrolyzed).

EXAMPLES

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

Example 1: 90% Core/10% Wt % Wall Melamine Capsule

A first mixture is prepared by combining 200 grams of water with 60 grams of styrene maleic anhydride copolymer (Ashland Water technologies, NC, USA). This first mixture is adjusted to pH 5.8 using citric acid solution. 6 grams of partially methylated methylol melamine resin (Cymel 385, 80% solids, Cytec, N.J., USA) is added to the emulsifier solution. 200 grams of the capsule core material which comprise a fragrance oil is added to the first mixture at a temperature of 50 C to form an emulsion. A low speed blending is used to achieve a volume-mean particle size of 30 micrometers. A second solution and 3 grams of sodium sulfate salt are added to the emulsion. This second solution contains 3 grams of acrylic acid (Sigma Aldrich, USA), 120 grams of distilled water, sodium hydroxide solution to adjust the pH to 4.8, 10 grams of partially methylated methylol melamine resin (Cymel 385, 80% solids, Cytec, N.J., USA). The temperature of the mixture is gradually raised to 85 degrees Centigrade, and is maintained at this temperature overnight with continuous stirring to complete the encapsulation.

Example 2: 90% Core/10% wt % Wall Melamine Capsule

A first mixture is prepared by combining 200 grams of water with 60 grams of styrene maleic anhydride copolymer (Ashland Water technologies, NC, USA). This first mixture is adjusted to pH 5.8 using citric acid solution. 6 grams of partially methylated methylol melamine resin (Cymel 385, 80% solids, Cytec, N.J., USA) is added to the emulsifier solution. 200 grams of the capsule core material which comprise a fragrance oil is added to the first mixture at a temperature of 50 C to form an emulsion. A low speed blending is used to achieve a volume-mean particle size of 30 micrometers. A second solution and 3 grams of sodium sulfate salt are added to the emulsion. This second solution contains 3 grams of acrylic acid (Sigma Aldrich, USA), 120 grams of distilled water, sodium hydroxide solution to adjust the pH to 4.8, 10 grams of partially methylated methylol melamine resin (Cymel 385, 80% solids, Cytec, N.J., USA). The temperature of the mixture is gradually raised to 85 degrees Centigrade, and is maintained at this temperature overnight with continuous stirring to complete the encapsulation.

Example 3: 90% Core/10% wt % Wall Melamine Capsule

A first mixture is prepared by combining 200 grams of water with 60 grams of styrene maleic anhydride copolymer (Ashland Water technologies, NC, USA). This first mixture is adjusted to pH5.8 using citric acid solution. 6 grams of partially methylated methylol melamine resin (Cymel 385, 80% solids, Cytec, N.J., USA) is added to the emulsifier solution. 200 grams of the capsule core material which comprise a suds suppressor, a silicone and a fragrance oil is added to the first mixture at a temperature of 50 C to form an emulsion. Low speed blending is used to achieve a volume-mean particle size of 15 micrometers. A second solution and 3 grams of sodium sulfate salt are added to the emulsion. This second solution contains 3 grams of acrylic acid (Sigma Aldrich, USA), 120 grams of distilled water, 10 grams of partially methylated methylol melamine resin (Cymel 385, 80% solids, Cytec, N.J., USA). The temperature of the mixture is gradually raised to 85 degrees Centigrade, and is maintained at this temperature overnight with continuous stirring to complete the encapsulation.

Example 4: 90% Core/10% Wt % Wall Melamine Capsule

A first mixture is prepared by combining 200 grams of water with 60 grams of styrene maleic anhydride copolymer (Ashland Water technologies, NC, USA). This first mixture is adjusted to pH5.8 using citric acid solution. 6 grams of partially methylated methylol melamine resin (Cymel 385, 80% solids, Cytec, N.J., USA) is added to the emulsifier solution. 200 grams of the capsule core material which comprise a sud suppressor, a silicone and a fragrance oil is added to the first mixture at a temperature of 50 C to form an emulsion. Low speed blending is used to achieve a volume-mean particle size of 15 micrometers. A second solution and 3 grams of sodium sulfate salt are added to the emulsion. This second solution contains 3 grams of acrylic acid (Sigma Aldrich, USA), 120 grams of distilled water, 10 grams of partially methylated methylol melamine resin (Cymel 385, 80% solids, Cytec, N.J., USA). The temperature of the mixture is gradually raised to 85 degrees Centigrade, and is maintained at this temperature overnight with continuous stirring to complete the encapsulation.

Example 5: Polyacrylate Capsule

Water Phase: 200 grams Impress SC-700 (Ashland Water Technologies, NC, USA)

5 grams 4,4'-Azobis(4-Cyanovaleric acid)
1400 grams Water

Internal Phase: 82 grams CN975 Urethane Acrylate Oligomer (Sartomer, Exton, Pa.)
1 gram Tert-Butylaminoethyl Methacrylate
1 gram Beta-Carboxyethyl Acrylate
850 grams perfume oil
4 grams 2,2'-Azobis(2-Methylbutyronitrile)
3 grams 4,4'-Azobis(4-Cyanovaleric acid)

The internal phase is mixed with stirring for one hour under a nitrogen blanket and brought to a temperature of 70 C and maintained at this temperature. The water phase components are also mixed with stirring. The oil phase components are cooled to 50 C and then are blended at high speed. The water phase is added to the internal phase and milled for one hour at 50 C to achieve a particle size of about 15 micrometers. The temperature was increased to 75 C and maintained along with continuous stirring for four hours and then heating was increased to 95 C for six hours. The resultant oil in water capsules had a size of about 16 micrometers.

Example 6: Production of Spray Dried Microcapsule 1200 g of perfume microcapsule slurry, containing one or more of the variants of microcapsules disclosed in the present specification, is mixed together with 700 g of water for 10 minutes using an IKA Eurostar mixer with R1382 attachment at a speed of 180 rpm. The mixture is then transferred over to a feeding vessel to be spray dried in a 1.2 m diameter Niro Production Minor. The slurry is fed into the tower using a Watson-Marlow 504U peristaltic pump and atomised using a 100 mm diameter rotary atomiser run at 18000 rpm, with co-current air flow for drying. The slurry is dried using an inlet temperature of 200° C. and outlet temperature of 95° C. to form a fine powder. The equipment used the spray drying process may be obtained from the following suppliers: IKA Werke GmbH & Co. KG, Janke and Kunkel-Str. 10, D79219 Staufen, Germany; Niro A/S Gladsaxevej 305, P.O. Box 45, 2860 Soeborg, Denmark and Watson-Marlow Bredel Pumps Limited, Falmouth, Cornwall, TR11 4RU, England.

Non-limiting examples of product formulations containing Perfume Microcapsules disclosed in the present specification are summarized in the following tables.

Example 7

Granular laundry detergent compositions for hand washing or washing machines, typically top-loading washing machines.

| | A (wt %) | B (wt %) | C (wt %) | D (wt %) | E (wt %) | F (wt %) |
|---|---|---|---|---|---|---|
| Linear alkylbenzenesulfonate | 20 | 22 | 20 | 15 | 19.5 | 20 |
| $C_{12-14}$ Dimethylhydroxyethyl ammonium chloride | 0.7 | 0.2 | 1 | 0.6 | 0.0 | 0 |
| AE3S | 0.9 | 1 | 0.9 | 0.0 | 0.4 | 0.9 |
| AE7 | 0.0 | 0.0 | 0.0 | 1 | 0.1 | 3 |
| Sodium tripolyphosphate | 5 | 0.0 | 4 | 9 | 2 | 0.0 |
| Zeolite A | 0.0 | 1 | 0.0 | 1 | 4 | 1 |
| 1.6R Silicate ($SiO_2$:$Na_2O$ at ratio 1.6:1) | 7 | 5 | 2 | 3 | 3 | 5 |
| Sodium carbonate | 25 | 20 | 25 | 17 | 18 | 19 |
| Polyacrylate MW 4500 | 1 | 0.6 | 1 | 1 | 1.5 | 1 |
| Random graft copolymer[1] | 0.1 | 0.2 | 0.0 | 0.0 | 0.05 | 0.0 |
| Carboxymethyl cellulose | 1 | 0.3 | 1 | 1 | 1 | 1 |
| Stainzyme ® (20 mg active/g) | 0.1 | 0.2 | 0.1 | 0.2 | 0.1 | 0.1 |

-continued

|  | A (wt %) | B (wt %) | C (wt %) | D (wt %) | E (wt %) | F (wt %) |
|---|---|---|---|---|---|---|
| Protease (Savinase ®, 32.89 mg active/g) | 0.1 | 0.1 | 0.1 | 0.1 |  | 0.1 |
| Amylase - Natalase ® (8.65 mg active/g) | 0.1 | 0.0 | 0.1 | 0.0 | 0.1 | 0.1 |
| Lipase - Lipex ® (18 mg active/g) | 0.03 | 0.07 | 0.3 | 0.1 | 0.07 | 0.4 |
| Fluorescent Brightener 1 | 0.06 | 0.0 | 0.06 | 0.18 | 0.06 | 0.06 |
| Fluorescent Brightener 2 | 0.1 | 0.06 | 0.1 | 0.0 | 0.1 | 0.1 |
| DTPA | 0.6 | 0.8 | 0.6 | 0.25 | 0.6 | 0.6 |
| MgSO$_4$ | 1 | 1 | 1 | 0.5 | 1 | 1 |
| Sodium Percarbonate | 0.0 | 5.2 | 0.1 | 0.0 | 0.0 | 0.0 |
| Sodium Perborate Monohydrate | 4.4 | 0.0 | 3.85 | 2.09 | 0.78 | 3.63 |
| NOBS | 1.9 | 0.0 | 1.66 | 0.0 | 0.33 | 0.75 |
| TAED | 0.58 | 1.2 | 0.51 | 0.0 | 0.015 | 0.28 |
| Sulphonated zinc phthalocyanine | 0.0030 | 0.0 | 0.0012 | 0.0030 | 0.0021 | 0.0 |
| S-ACMC | 0.1 | 0.0 | 0.0 | 0.0 | 0.06 | 0.0 |
| Direct Violet Dye (DV9 or DV99 or DV66) | 0.0 | 0.0 | 0.0003 | 0.0001 | 0.0001 | 0.0 |
| Neat Perfume[(1)] | 0.5 | 0.5 | 0.5 | 0.5 | 0.5 | 0.5 |
| Microcapsules[(2)] | 0.7 | 1.0 | 2.3 | 0.5 | 1.2 | 0.8 |
| Sulfate/Moisture | Balance | | | | | |

[(1)]Optional.
[(2)]Microcapsules of the present invention comprising a core that comprises perfume and/or a silicone.

Example 8

Granular laundry detergent compositions typically for front-loading automatic washing machines.

|  | A (wt %) | B (wt %) | C (wt %) | D (wt %) | E (wt %) | F (wt %) |
|---|---|---|---|---|---|---|
| Linear alkylbenzenesulfonate | 8 | 7.1 | 7 | 6.5 | 7.5 | 7.5 |
| AE3S | 0 | 4.8 | 1.0 | 5.2 | 4 | 4 |
| C12-14 Alkylsulfate | 1 | 0 | 1 | 0 | 0 | 0 |
| AE7 | 2.2 | 0 | 2.2 | 0 | 0 | 0 |
| C$_{10-12}$ Dimethyl hydroxyethylammonium chloride | 0.75 | 0.94 | 0.98 | 0.98 | 0 | 0 |
| Crystalline layered silicate ($\delta$-Na$_2$Si$_2$O$_5$) | 4.1 | 0 | 4.8 | 0 | 0 | 0 |
| Zeolite A | 5 | 0 | 5 | 0 | 2 | 2 |
| Citric Acid | 3 | 5 | 3 | 4 | 2.5 | 3 |
| Sodium Carbonate | 15 | 20 | 14 | 20 | 23 | 23 |
| Silicate 2R (SiO$_2$:Na$_2$O at ratio 2:1) | 0.08 | 0 | 0.11 | 0 | 0 | 0 |
| Soil release agent | 0.75 | 0.72 | 0.71 | 0.72 | 0 | 0 |
| Acrylic Acid/Maleic Acid Copolymer | 1.1 | 3.7 | 1.0 | 3.7 | 2.6 | 3.8 |
| Carboxymethylcellulose | 0.15 | 1.4 | 0.2 | 1.4 | 1 | 0.5 |
| Protease - Purafect ® (84 mg active/g) | 0.2 | 0.2 | 0.3 | 0.15 | 0.12 | 0.13 |
| Amylase - Stainzyme Plus ® (20 mg active/g) | 0.2 | 0.15 | 0.2 | 0.3 | 0.15 | 0.15 |
| Lipase - Lipex ® (18.00 mg active/g) | 0.05 | 0.15 | 0.1 | 0 | 0 | 0 |
| Amylase - Natalase ® (8.65 mg active/g) | 0.1 | 0.2 | 0 | 0 | 0.15 | 0.15 |
| Cellulase - Celluclean ™ (15.6 mg active/g) | 0 | 0 | 0 | 0 | 0.1 | 0.1 |
| TAED | 3.6 | 4.0 | 3.6 | 4.0 | 2.2 | 1.4 |
| Percarbonate | 13 | 13.2 | 13 | 13.2 | 16 | 14 |
| Na salt of Ethylenediamine-N,N'-disuccinic acid, (S,S) isomer (EDDS) | 0.2 | 0.2 | 0.2 | 0.2 | 0.2 | 0.2 |
| Hydroxyethane di phosphonate (HEDP) | 0.2 | 0.2 | 0.2 | 0.2 | 0.2 | 0.2 |
| MgSO$_4$ | 0.42 | 0.42 | 0.42 | 0.42 | 0.4 | 0.4 |
| Perfume | 0.5 | 0.6 | 0.5 | 0.6 | 0.6 | 0.6 |
| Suds suppressor agglomerate | 0.05 | 0.1 | 0.05 | 0.1 | 0.06 | 0.05 |
| Soap | 0.45 | 0.45 | 0.45 | 0.45 | 0 | 0 |
| Sulphonated zinc phthalocyanine (active) | 0.0007 | 0.0012 | 0.0007 | 0 | 0 | 0 |
| S-ACMC | 0.01 | 0.01 | 0 | 0.01 | 0 | 0 |
| Direct Violet 9 (active) | 0 | 0 | 0.0001 | 0.0001 | 0 | 0 |
| Neat Perfume[(1)] | 0.5 | 0.5 | 0.5 | 0.5 | 0.5 | 0.5 |
| Perfume Microcapsules[(2)] | 2.0 | 1.5 | 0.9 | 2.2 | 1.5 | 0.8 |
| Sulfate/Water & Miscellaneous | Balance | | | | | |

[(1)]Optional.
[(2)]Microcapsules of the present invention comprising a core that comprises perfume and/or a silicone.

The typical pH is about 10.

Example 9 Heavy Duty Liquid Laundry Detergent Compositions

| | A (wt %) | B (wt %) | C (wt %) | D (wt %) | E (wt %) | F (wt %) | G (wt %) |
|---|---|---|---|---|---|---|---|
| AES $C_{12-15}$ alkyl ethoxy (1.8) sulfate | 11 | 10 | 4 | 6.32 | 0 | 0 | 0 |
| AE3S | 0 | 0 | 0 | 0 | 2.4 | 0 | 0 |
| Linear alkyl benzene sulfonate/sulfonic acid | 1.4 | 4 | 8 | 3.3 | 5 | 8 | 19 |
| HSAS | 3 | 5.1 | 3 | 0 | 0 | 0 | 0 |
| Sodium formate | 1.6 | 0.09 | 1.2 | 0.04 | 1.6 | 1.2 | 0.2 |
| Sodium hydroxide | 2.3 | 3.8 | 1.7 | 1.9 | 1.7 | 2.5 | 2.3 |
| Monoethanolamine | 1.4 | 1.49 | 1.0 | 0.7 | 0 | 0 | To pH 8.2 |
| Diethylene glycol | 5.5 | 0.0 | 4.1 | 0.0 | 0 | 0 | 0 |
| AE9 | 0.4 | 0.6 | 0.3 | 0.3 | 0 | 0 | 0 |
| AE8 | 0 | 0 | 0 | 0 | 0 | 0 | 20.0 |
| AE7 | 0 | 0 | 0 | 0 | 2.4 | 6 | 0 |
| Chelant (HEDP) | 0.15 | 0.15 | 0.11 | 0.07 | 0.5 | 0.11 | 0.8 |
| Citric Acid | 2.5 | 3.96 | 1.88 | 1.98 | 0.9 | 2.5 | 0.6 |
| $C_{12-14}$ dimethyl Amine Oxide | 0.3 | 0.73 | 0.23 | 0.37 | 0 | 0 | 0 |
| $C_{12-18}$ Fatty Acid | 0.8 | 1.9 | 0.6 | 0.99 | 1.2 | 0 | 15.0 |
| 4-formyl-phenylboronic acid | 0 | 0 | 0 | 0 | 0.05 | 0.02 | 0.01 |
| Borax | 1.43 | 1.5 | 1.1 | 0.75 | 0 | 1.07 | 0 |
| Ethanol | 1.54 | 1.77 | 1.15 | 0.89 | 0 | 3 | 7 |
| A compound having the following general structure: bis$((C_2H_5O)(C_2H_4O)n)(CH_3)$—$N^+$—$C_xH_{2x}$—$N^+$—$(CH_3)$-bis$((C_2H_5O)(C_2H_4O)n)$, wherein n = from 20 to 30, and x = from 3 to 8, or sulphated or sulphonated variants thereof | 0.1 | 0 | 0 | 0 | 0 | 0 | 2.0 |
| Ethoxylated ($EO_{15}$) tetraethylene pentamine | 0.3 | 0.33 | 0.23 | 0.17 | 0.0 | 0.0 | 0 |
| Ethoxylated Polyethylenimine | 0 | 0 | 0 | 0 | 0 | 0 | 0.8 |
| Ethoxylated hexamethylene diamine | 0.8 | 0.81 | 0.6 | 0.4 | 1 | 1 | |
| 1,2-Propanediol | 0.0 | 6.6 | 0.0 | 3.3 | 0.5 | 2 | 8.0 |
| Fluorescent Brightener | 0.2 | 0.1 | 0.05 | 0.3 | 0.15 | 0.3 | 0.2 |
| Hydrogenated castor oil derivative structurant | 0.1 | 0 | 0 | 0 | 0 | 0 | 0.1 |
| Perfume | 1.6 | 1.1 | 1.0 | 0.8 | 0.9 | 1.5 | 1.6 |
| Protease (40.6 mg active/g) | 0.8 | 0.6 | 0.7 | 0.9 | 0.7 | 0.6 | 1.5 |
| Mannanase: Mannaway ® (25 mg active/g) | 0.07 | 0.05 | 0.045 | 0.06 | 0.04 | 0.045 | 0.1 |
| Amylase: Stainzyme ® (15 mg active/g) | 0.3 | 0 | 0.3 | 0.1 | 0 | 0.4 | 0.1 |
| Amylase: Natalase ® (29 mg active/g) | 0 | 0.2 | 0.1 | 0.15 | 0.07 | 0 | 0.1 |
| Xyloglucanase (Whitezyme ®, 20 mg active/g) | 0.2 | 0.1 | 0 | 0 | 0.05 | 0.05 | 0.2 |
| Lipex ® (18 mg active/g) | 0.4 | 0.2 | 0.3 | 0.1 | 0.2 | 0 | 0 |
| Neat Perfume[1] | 0.5 | 0.5 | 0.5 | 0.5 | 0.5 | 0.5 | 0.5 |
| Perfume Microcapsules[2] | 0.25 | 3.2 | 2.5 | 4.0 | 2.5 | 1.4 | 0.8 |
| *Water, dyes & minors | | | | Balance | | | |

*Based on total cleaning and/or treatment composition weight, a total of no more than 12% water
[1] Optional.
[2] Microcapsules of the present invention comprising a core that comprises perfume and/or a silicone.

Example 10 Unit Dose Compositions

| Example of Unit Dose detergents | A | B |
|---|---|---|
| $C_{14-15}$ alkyl poly ethoxylate (8) | 12 | — |
| $C_{12-14}$ alkyl poly ethoxylate (7) | 1 | 14 |
| $C_{12-14}$ alkyl poly ethoxylate (3) sulfate Mono EthanolAmine salt | 8.4 | 9 |
| Linear Alkylbenzene sulfonic acid | 15 | 16 |
| Citric Acid | 0.6 | 0.5 |
| $C_{12-18}$ Fatty Acid | 15 | 17 |
| Enzymes | 1.5 | 1.2 |
| PEI 600 EO20 | 4 | — |
| Diethylene triamine penta methylene phosphonic acid or HEDP | 1.3 | — |
| Fluorescent brightener | 0.2 | 0.3 |
| Hydrogenated Castor Oil | 0.2 | 0.2 |
| 1,2 propanediol | 16 | 12 |
| Glycerol | 6.2 | 8.5 |
| Sodium hydroxide | — | 1 |
| Mono Ethanol Amine | 7.9 | 6.1 |
| Dye | Present | Present |
| PDMS | — | 2.7 |
| Potassium sulphite | 0.2 | 0.2 |
| Perfume Microcapsules [2] | 1.5 | 0.9 |
| Water | Up to 100% | Up to 100% |

[2] Microcapsules of the present invention comprising a core that comprises perfume and/or a silicone.

Raw Materials and Notes for Composition Examples

LAS is linear alkylbenzenesulfonate having an average aliphatic carbon chain length $C_9$-$C_{15}$ supplied by Stepan, Northfield, Ill., USA or Huntsman Corp. (HLAS is acid form).

$C_{12-14}$ Dimethylhydroxyethyl ammonium chloride, supplied by Clariant GmbH, Germany.

AE3S is $C_{12-15}$ alkyl ethoxy (3) sulfate supplied by Stepan, Northfield, Ill., USA.

AE7 is $C_{12-15}$ alcohol ethoxylate, with an average degree of ethoxylation of 7, supplied by Huntsman, Salt Lake City, Utah, USA.

AES is $C_{10-18}$ alkyl ethoxy sulfate supplied by Shell Chemicals.

AE9 is $C_{12-13}$ alcohol ethoxylate, with an average degree of ethoxylation of 9, supplied by Huntsman, Salt Lake City, Utah, USA.

HSAS or HC1617HSAS is a mid-branched primary alkyl sulfate with average carbon chain length of about 16-17.

Sodium tripolyphosphate is supplied by Rhodia, Paris, France.

Zeolite A is supplied by Industrial Zeolite (UK) Ltd, Grays, Essex, UK.

1.6R Silicate is supplied by Koma, Nestemica, Czech Republic.

Sodium Carbonate is supplied by Solvay, Houston, Tex., USA.

Polyacrylate MW 4500 is supplied by BASF, Ludwigshafen, Germany.

Carboxymethyl cellulose is Finnfix® V supplied by CP Kelco, Arnhem, Netherlands.

Suitable chelants are, for example, diethylenetetraamine pentaacetic acid (DTPA) supplied by Dow Chemical, Midland, Mich., USA or Hydroxyethane di phosphonate (HEDP) supplied by Solutia, St Louis, Mo., USA Bagsvaerd, Denmark.

Savinase®, Natalase®, Stainzyme®, Lipex®, Celluclean™, Mannaway® and Whitezyme® are all products of Novozymes, Bagsvaerd, Denmark.

Proteases may be supplied by Genencor International, Palo Alto, Calif., USA (e.g. Purafect Prime®) or by Novozymes, Bagsvaerd, Denmark (e.g. Liquanase®, Coronase®).

Fluorescent Brightener 1 is Tinopal® AMS, Fluorescent Brightener 2 is Tinopal® CBS-X, Sulphonated zinc phthalocyanine and Direct Violet 9 is Pergasol® Violet BN-Z all supplied by Ciba Specialty Chemicals, Basel, Switzerland.

Sodium percarbonate supplied by Solvay, Houston, Tex., USA.

Sodium perborate is supplied by Degussa, Hanau, Germany.

NOBS is sodium nonanoyloxybenzenesulfonate, supplied by Future Fuels, Batesville, USA.

TAED is tetraacetylethylenediamine, supplied under the Peractive® brand name by Clariant GmbH, Sulzbach, Germany.

S-ACMC is carboxymethylcellulose conjugated with C.I. Reactive Blue 19, sold by Megazyme, Wicklow, Ireland under the product name AZO-CM-CELLULOSE, product code S-ACMC.

Soil release agent is Repel-o-Tex® PF, supplied by Rhodia, Paris, France.

Acrylic Acid/Maleic Acid Copolymer is molecular weight 70,000 and acrylate:maleate ratio 70:30, supplied by BASF, Ludwigshafen, Germany.

Na salt of Ethylenediamine-N,N'-disuccinic acid, (S,S) isomer (EDDS) is supplied by Octel, Ellesmere Port, UK.

Hydroxyethane di phosphonate (HEDP) is supplied by Dow Chemical, Midland, Mich., USA.

Suds suppressor agglomerate is supplied by Dow Corning, Midland, Mich., USA.

HSAS is mid-branched alkyl sulfate as disclosed in U.S. Pat. No. 6,020,303 and U.S. Pat. No. 6,060,443.

$C_{12-14}$ dimethyl Amine Oxide is supplied by Procter & Gamble Chemicals, Cincinnati, USA.

Random graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40:60 and no more than 1 grafting point per 50 ethylene oxide units.

Ethoxylated polyethyleneimine is polyethyleneimine (MW=600) with 20 ethoxylate groups per —NH.

Cationic cellulose polymer is LK400, LR400 and/or JR30M from Amerchol Corporation, Edgewater N.J.

Note: all enzyme levels are expressed as % enzyme raw material.

Example 11 Liquid Fabric Enhancer Performance

1. Product Making

LFE products were made containing 0.4% of perfume oil added via PMC

2. Load Composition

Perfume ballast load is 3 kg and contains:

600 g Polyester 600 g Polycotton 600 g Muslin (flat) cotton 600 g Knitted cotton 600 g Terry towels Ballast loads are preconditioned: 2×70 g Ariel Sensitive, 95° C. wash+2× nil powder, short cotton wash @95° C.

After each wash test ballast load is rewashed: 2×70 g Ariel Sensitive, 95° C. wash+2× nil powder, short cotton wash @95° C.

For each wash test we add 6 terry tracers (Maes Textiel).

Tracers are preconditioned: 2×70 g Ariel Sensitive, 95° C. wash+2× nil powder, short cotton wash @95° C. Tracers are not re-used!

3. Wash Conditions

Before test, WM is boil washed (short cotton wash @95° C.)

Test Conditions:

Miele Novotronic W526

Short cotton cycle wash at 60° C., 1200 rpm spin speed with 50 g Ariel Sensitive powder Put load in WM, add powder in dispenser.

Also add a dosage of 35 ml LFE in the dispenser

Run wash cycle

Loads are evaluated wet, after 1 day line drying (nil and with rubbing)

After test ballast load is rewashed

Tracers are not re-used.

4. Perfume Evaluation

Terry tracers are evaluated by perfumers and graded on the Primavera scale.

5. Performance Results

|  | Delta on WFO | Delta on DFO | Leakage (1 wk 35 C. in Concerto dilute) |
|---|---|---|---|
| PMCs made in accordance with Example 2 of USPA 2008/0305982 A1 | Ref | Ref | 5.6% |
| PMC made in accordance with Example 1 of the present application | +10 | 0 | 2.1% |

The data shows that on wet fabrics the performance of the PMCs according to the present application is improved when compared to the PMCs of Example X of USPA 2008/0305982 A1, without any loss of performance on dry fabrics.

Beauty Care Examples

Example A. Antiperspirant Compositions

Following, in Table 1, are Examples of antiperspirant compositions. Examples A, B, and C are invisible solid anhydrous antiperspirant compositions including dried polymeric friable microcapsules made by interfacial polymerization, wherein the microcapsules encapsulate a perfume, and varying percentages of non-volatile oils. Examples D, E, and F are semi-solid anhydrous antiperspirant compositions including dried polymeric friable microcapsules made by interfacial polymerization, wherein the microcapsules encapsulate a perfume, and varying percentages of non-volatile oils.

TABLE 1

|  | Example A | Example B | Example C | Example D | Example E | Example F |
|---|---|---|---|---|---|---|
| Aluminum Zirconium Trichlorohydrex Glycine Powder | 24 | 24 | 24 | 26.5 | 26.5 | 26.5 |
| Cyclopentasiloxane | QS | QS | QS | QS | QS | — |
| Dimethicone* | — | — | — | 5 | 5 | 61.725 |
| CO-1897 Stearyl Alcohol NF | 14 | 14 | 14 | — | — | — |
| Hydrogenated Castor Oil MP80 Deodorized | 3.85 | 3.85 | 3.85 | — | — | — |
| Behenyl Alcohol | 0.2 | 0.2 | 0.2 | — | — | — |
| Tribehenin | — | — | — | 4.5 | 4.5 | 4.5 |
| C 18-36 acid triglyceride | — | — | — | 1.125 | 1.125 | 1.125 |
| C12-15 Alkyl Benzoate* | 9.5 | 9.5 | 5 | — | — | — |
| PPG-14 Butyl Ether* | 6.5 | 6.5 | — | 0.5 | 0.5 | 0.5 |
| Phenyl Trimethicone* | 3 | — | — | — | — | — |
| White Petrolatum* | 3 | — | — | 3 | — | 3 |
| Mineral Oil* | 1.0 | 1.0 | 1.0 | — | — | — |
| Fragrance | 0.75 | 0.75 | 0.75 | 0.75 | 0.75 | 0.75 |
| Talc Imperial 250 USP | 3.0 | 3.0 | 3.0 | — | — | — |
| Polyacrylate Microcapsule | 1.9 | 1.9 | 1.9 | 1.9 | 1.9 | 1.9 |

QS - indicates that this material is used to bring the total to 100%.

*indicates the non-volatile oils.

Following, in Table 2, are further Examples of antiperspirant compositions. Examples G and H are invisible solid anhydrous antiperspirant compositions including dried polymeric friable microcapsules made by interfacial polymerization, wherein the microcapsules encapsulate a perfume, and low percentages of non-volatile oils.

TABLE 2

|  | Example G | Example H |
|---|---|---|
| Aluminum Zirconium Trichlorohydrex Glycine Powder | 25.6 | 25.6 |
| Cyclopentasiloxane | QS | QS. |
| CO-1897 Stearyl Alcohol NF | 13 | 13 |
| Hydrogenated Castor Oil MP80 Deodorized | 2.9 | 2.9 |
| Behenyl Alcohol | 0.2 | 0.2 |
| Ozokerite Wax SP-1026 | 1.0 | 1.0 |
| C12-15 Alkyl Benzoate* | 8.5 | 8.5 |
| PPG-14 Butyl Ether* | 6.5 | 6.5 |
| Mineral Oil* | 1.0 | 1.0 |
| Fragrance | 0.75 | 0.75 |
| Talc Imperial 250 USP | 2.5 | 2.5 |
| Polyacrylate Microcapsule | 1.5 | 2.5 |
| Fragrance Complexed Beta-cyclodextrin | 3 | 3 |
| DL-ALPHA Tocopheryl Acetate (Vitamin E) | 0.1 | 0.1 |
| d-Panthenyl Triacetate | 0.1 | 0.1 |
| Acetyl Glucosamine | 0.1 | 0.1 |

QS - indicates that this material is used to bring the total to 100%.

*indicates the non-volatile oils.

Example B. Microcapsules in Leave-on Conditioner

Microcapsule slurry is added to leave-on conditioner, then mixed using a Speed Mixer DAFC 600FVZ, at 800 RPM for 1 minute.

A typical composition of a leave-on conditioner formulation is given in the following table:

| Components | Ex. II (LOT) (%) |
|---|---|
| Premix | |
| Aminosilicone | — |
| PDMS | 1.0-1.5 |
| Gel matrix carrier | |
| Behenyl trimethyl ammonium chloride | — |
| Stearamidopropyldimethylamine (SAPDMA), C18 | 0.60-0.8 |
| DTDMAC, C18(Quaternium-18) | 0.45-0.6 |
| Citric Acid (anhydrous) | 0.10-0.25 |
| Cetyl alcohol | 0.80-1.0 |
| Stearyl alcohol | 0.54-1.0 |
| Deionized Water | Balance |
| Polymers | |
| Hydroxyethylcellulose (HEC) | 0.15-0.50 |
| PEG-2M (Polyox WAR N-10) | 0.30-0.60 |
| Others | |
| Perfume microcapsules | 0.10-1.20 |
| Preservatives | 0.40-0.60 |

Example C. Shampoo Formulation

Microcapsules area added to a shampoo composition, mixed using a Speed Mixer DAFC 600FVZ mixer, at 1900 RPM for 1 minute.

| | EXAMPLE COMPOSITION | | |
|---|---|---|---|
| Ingredient | I | II | III |
| Water | q.s. | q.s. | q.s. |
| Polyquaternium 76 [1] | 2.50 | — | — |
| Guar, Hydroxylpropyl Trimonium Chloride [2] | — | 0.25 | — |
| Polyquaterium 6 [3] | — | — | 0.79 |
| Sodium Laureth Sulfate (SLE3S) [4] | 21.43 | 21.43 | 21.43 |
| Sodium Lauryl Sulfate (SLS) [5] | 20.69 | 20.69 | 20.69 |
| Silicone [6] | 0.75 | 1.00 | 0.5 |
| Cocoamidopropyl Betaine [7] | 3.33 | 3.33 | 3.33 |
| Cocoamide MEA [8] | 1.0 | 1.0 | 1.0 |
| Ethylene Glycol Distearate [9] | 1.50 | 1.50 | 1.50 |
| Sodium Chloride [10] | 0.25 | 0.25 | 0.25 |
| Fragrance | 0.70 | 0.70 | 0.70 |
| Fragrance Microcapsule | 1.2 | 1.2 | 1.2 |
| Preservatives, pH adjusters | Up to 1% | Up to 1% | Up to 1% |

[1] Mirapol AT-1, Copolymer of Acrylamide(AM) and TRIQUAT, MW = 1,000,000; CD = 1.6 meq./gram; 10% active; Supplier Rhodia
[2] Jaguar C500, MW - 500,000, CD = 0.7, supplier Rhodia
[3] Mirapol 100S, 31.5% active, supplier Rhodia
[4] Sodium Laureth Sulfate, 28% active, supplier: P&G
[5] Sodium Lauryl Sulfate, 29% active supplier: P&G
[6] Glycidol Silicone VC2231-193C
[7] Tegobetaine F-B, 30% active supplier: Goldschmidt Chemicals
[8] Monamid CMA, 85% active, supplier Goldschmidt Chemical
[9] Ethylene Glycol Distearate, EGDS Pure, supplier Goldschmidt Chemical
[10] Sodium Chloride USP (food grade), supplier Morton; note that salt is an adjustable ingredient, higher or lower levels may be added to achieve target viscosity.

Example D. Microcapsules in Lotion

| Example | I | II | III |
|---|---|---|---|
| PHASE A | | | |
| DC-9040 [1] | 8.60 | 3.00 | 5.00 |
| Dimethicone | 4.09 | 4.00 | 4.00 |
| Polymethylsilsesquioxane [2] | 4.09 | 4.00 | 4.00 |
| Cyclomethicone | 11.43 | 0.50 | 11.33 |
| KSG-210 [3] | 5.37 | 5.25 | 5.40 |
| Polyethylene wax [4] | 3.54 | | 2.05 |
| DC-2503 Cosmetic Wax [5] | 7.08 | 10.00 | 3.77 |
| Hydrophobic TiO2 | | | 0.50 |
| Iron oxide coated Mica | | | 0.65 |
| TiO2 Coated Mica | 1.00 | 1.00 | |
| Fragrance Particles of Example 3 | 1.00 | 1.00 | 1.00 |
| PHASE B | | | |
| Glycerin | 10.00 | 10.00 | 10.00 |
| Dexpanthenol | 0.50 | 0.50 | 0.50 |
| Pentylene Glycol | 3.00 | 3.00 | 3.00 |
| Hexamidine Diisethionate [6] | 0.10 | 0.10 | 0.10 |
| Niacinamide [7] | 5.00 | 5.00 | 5.00 |
| Methylparaben | 0.20 | 0.20 | 0.20 |
| Ethylparaben | 0.05 | 0.05 | 0.05 |
| Sodium Citrate | 0.20 | 0.20 | 0.20 |
| Citric Acid | 0.03 | 0.03 | 0.03 |
| Sodium Benzoate | 0.05 | 0.05 | 0.05 |
| Sodium Chloride | 0.50 | 0.50 | 0.50 |
| FD&C Red #40 (1%) | 0.05 | 0.05 | 0.05 |
| Water | q.s to 100 | q.s to 100 | q.s to 100 |
| Hardness at 21° C. (g) | 33.3 | 15.4 | 14.2 |
| Hardness at 33° C. (g) | 6.4 | 0.7 | 4.0 |

[1] 12.5% Dimethicone Crosspolymer in Cyclopentasiloxane. Available from Dow Corning ™.
[2] E.g., Tospearl ™ 145A or Tospearl 2000. Available from GE Toshiba Silicone ™.
[3] 25% Dimethicone PEG-10/15 Crosspolymer in Dimethicone. Available from Shin-Etsu ™.
[4] Jeenate ™ 3H polyethylene wax from Jeen ™
[5] Stearyl Dimethicone. Available from Dow Corning.
[6] Hexamidine diisethionate, available from Laboratoires Serobiologiques.
[7] Additionally or alternatively, the composition may comprise one or more other skin care actives, their salts and derivatives, as disclosed herein, in amounts also disclosed herein as would be deemed suitable by one of skill in the art.

For the examples above, in a suitable container, combine the ingredients of Phase A. In a separate suitable container, combine the ingredients of Phase B. Heat each phase to 73° C.-78° C. while mixing each phase using a suitable mixer (e.g., Anchor blade, propeller blade, or IKA T25) until each reaches a substantially constant desired temperature and is homogenous. Slowly add Phase B to Phase A while continuing to mix Phase A. Continue mixing until batch is uniform. Pour product into suitable containers at 73-78° C. and store at room temperature. Alternatively, continuing to stir the mixture as temperature decreases results in lower observed hardness values at 21 and 33° C.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A composition comprising an adjunct material and benefit agent delivery particles comprising a core and a shell, said shell encapsulating said core, said shell comprising:
   a) styrene maleic anhydride monomethylmaleate, and/or a salt thereof, said styrene maleic anhydride monomethylmaleate, and/or a salt thereof having one or more of the following properties:
      (i) a molar ratio of styrene to maleic anhydride of from about 9:1 to about 1:9;
      (ii) a weight average molecular weight of from about 1,000 Da to about 100,000,000 Da;
      (iii) a density of from about 1.03 g/cm$^3$ to about 1.11 g/cm$^3$;
      (iv) a hydrolysis degree of from about 20% to about 95%
   b) a material selected from the group consisting of a polyacrylate, a polyethylene glycol acrylate, a polyurethane acrylate, an epoxy acrylate, a polymethacrylate, a polyethylene glycol methacrylate, a polyurethane methacrylate, an epoxy methacrylate and mixtures thereof;
   c) optionally, a colloid; and
   d) optionally, an emulsifier
   said composition being a slurry which is a product other than a consumer product.

2. The composition of claim 1 comprising:
   a) benefit agent delivery particles, comprising:
      (i) a core material comprising selected from the group consisting of perfume, suds suppressor or mixtures thereof;
      (ii) a shell that encapsulates said core material, said shell comprising based on total benefit agent particle shell weight, from about 1% to about 80%, of a styrene maleic anhydride monomethylmaleate, and/or a salt thereof;
      (iii) a colloid
   b) an adjunct material and
   c) optionally, a deposition aid.

3. A composition according to claim 1 wherein said benefit agent delivery particles, have a mean particle size of from about 1 micrometers to about 100 micrometers.

4. A composition according to claim 1 wherein and at least 75% of said benefit agent delivery particles have a fracture strength of from about 0.2 MPa to about 10 MPa.

5. A composition according to claim 1, wherein said shell comprises a polyacrylate that comprises a material selected from the group consisting of an amine acrylate, methacrylate monomer, a carboxylic acid acrylate, carboxylic acid methacrylate monomer and mixtures thereof.

6. A composition according to claim 1, comprising a deposition aid.

7. A composition according to claim 6, wherein said deposition aid coats the outer surface of said shell.

8. A composition according to claim 7, wherein said deposition aid comprises a material selected from the group consisting of poly(meth)acrylate, poly(ethylene-maleic anhydride), polyamine, wax, polyvinylpyrrolidone, polyvinylpyrrolidone co-polymers, polyvinylpyrrolidone-ethyl acrylate, polyvinylpyrrolidone-vinyl acrylate, polyvinylpyrrolidone methylacrylate, polyvinylpyrrolidone/vinyl acetate, polyvinyl acetal, polyvinyl butyral, polysiloxane, poly(propylene maleic anhydride), maleic anhydride derivatives, co-polymers of maleic anhydride derivatives, polyvinyl alcohol, styrene-butadiene latex, gelatin, gum Arabic, carboxymethyl cellulose, carboxymethyl hydroxyethyl cellulose, hydroxyethyl cellulose, other modified celluloses, sodium alginate, chitosan, casein, pectin, modified starch, polyvinyl acetal, polyvinyl butyral, polyvinyl methyl ether/maleic anhydride, polyvinyl pyrrolidone and its co polymers, poly(vinyl pyrrolidone/methacrylamidopropyl trimethyl ammonium chloride), polyvinylpyrrolidone/vinyl acetate, polyvinyl pyrrolidone/dimethylaminoethyl methacrylate, polyvinyl amines, polyvinyl formamides, polyallyl amines and copolymers of polyvinyl amines, polyvinyl formamides, and polyallyl amines and mixtures thereof.

9. A composition according to claim 8, wherein said deposition aid comprises a material selected from the group consisting of poly(meth)acrylates, poly(ethylene-maleic anhydride), polyamine, polyvinylpyrrolidone, polyvinylpyrrolidone-ethyl acrylate, polyvinylpyrrolidone-vinyl acrylate, polyvinylpyrrolidone methylacrylate, polyvinylpyrrolidone/vinyl acetate, polyvinyl acetal, polyvinyl butyral, polysiloxane, poly(propylene maleic anhydride), maleic anhydride derivatives, co-polymers of maleic anhydride derivatives, polyvinyl alcohol, carboxymethyl cellulose, carboxymethyl hydroxyethyl cellulose, hydroxyethyl cellulose, polyvinyl methyl ether/maleic anhydride, poly(vinyl pyrrolidone/methacrylamidopropyl trimethyl ammonium chloride), polyvinylpyrrolidone/vinyl acetate, polyvinyl pyrrolidone/dimethylaminoethyl methacrylate, polyvinyl amines, polyvinyl formamides, polyallyl amines and copolymers of polyvinyl amines, polyvinyl formamides, and polyallyl amines and mixtures thereof.

10. A composition according to claim 9, said deposition aid comprises a material selected from the group consisting of poly(meth)acrylates, poly(ethylene-maleic anhydride), polyamine, polyvinylpyrrolidone, polyvinylpyrrolidone-ethyl acrylate, polyvinylpyrrolidone-vinyl acrylate, polyvinylpyrrolidone methylacrylate, polyvinylpyrrolidone/vinyl acetate, polyvinyl acetal, polysiloxane, poly(propylene maleic anhydride), maleic anhydride derivatives, co-polymers of maleic anhydride derivatives, polyvinyl alcohol, carboxymethyl cellulose, carboxymethyl hydroxyethyl cellulose, hydroxyethyl cellulose, polyvinyl methyl ether/maleic anhydride, polyvinylpyrrolidone/vinyl acetate, polyvinyl pyrrolidone/dimethylaminoethyl methacrylate, polyvinyl amines, polyvinyl formamides, polyallyl amines and copolymers of polyvinyl amines, polyvinyl formamides, and polyallyl amines and mixtures thereof.

11. A composition according to claim 1, wherein at least 75% of said benefit agent delivery particles have a particle size of from about 1 micrometer to about 80 micrometers.

12. A composition claim 1, wherein at least 75% of said benefit agent delivery particles have a particle wall thickness of from about 10 nm to about 250 nm.

13. A composition according to claim 1, wherein said benefit agent delivery particles' core material comprises a perfume composition selected from the group consisting of:
   a) a perfume composition having a Clog P of less than 4.5;
   b) a perfume composition comprising, based on total perfume composition weight, 60% perfume materials having a Clog P of less than 4.0;
   c) a perfume composition comprising, based on total perfume composition weight, 35% perfume materials having a Clog P of less than 3.5;

d) a perfume composition comprising, based on total perfume composition weight, 40% perfume materials having a Clog P of less than 4.0 and at least 1% perfume materials having a Clog P of less than 2.0;
e) a perfume composition comprising, based on total perfume composition weight, 40% perfume materials having a Clog P of less than 4.0 and at least 15% perfume materials having a Clog P of less than 3.0;
f) a perfume composition comprising, based on total perfume composition weight, at least 1% butanoate esters and at least 1% of pentanoate esters;
g) a perfume composition comprising, based on total perfume composition weight, at least 2% of an ester comprising an allyl moiety and at least 10% of another perfume comprising an ester moiety;
h) a perfume composition comprising, based on total perfume composition weight, at least 1% of an aldehyde comprising an alkyl chain moiety;
i) a perfume composition comprising, based on total perfume composition weight, at least 2% of a butanoate ester;
j) a perfume composition comprising, based on total perfume composition weight, at least 1% of a pentanoate ester;
k) a perfume composition comprising, based on total perfume composition weight, at least 3% of an ester comprising an allyl moiety and 1% of an aldehyde comprising an alkyl chain moiety;
l) a perfume composition comprising, based on total perfume composition weight, at least 25% of a perfume comprising an ester moiety and 1% of an aldehyde comprising an alkyl chain moiety;
n) a perfume compositions comprising, based on total perfume composition weight, at least 2% of a material selected from 4-(2,6,6-trimethyl-1-cyclohexenyl)-3-buten-2-one, 4-(2,6,6-trimethyl-2-cyclohexenyl)-3-buten-2-one and 3-buten-2-one, 3-methyl-4-(2,6,6-trimethyl-1-cyclohexen-2-yl)- and mixtures thereof;
n) a perfume composition comprising, based on total perfume composition weight, at least 0.1% of tridec-2-enonitrile, and mandaril, and mixtures thereof;
(o) a perfume composition comprising, based on total perfume composition weight, at least 2% of a material selected from 3,7dimethyl-6-octene nitrile, 2-cyclohexylidene-2-phenylacetonitrile and mixtures thereof;
(p) a perfume composition comprising, based on total perfume composition weight, at least 80% of one or more perfumes comprising a moiety selected from the group consisting of esters, aldehydes, ionones, nitriles, ketones and combinations thereof;
(q) a perfume composition comprising, based on total perfume composition weight, at least 3% of an ester comprising an allyl moiety; a perfume composition comprising, based on total perfume composition weight, at least 20% of a material selected from the group consisting of: 1-methylethyl-2-methylbutanoate; ethyl-2-methyl pentanoate; 1,5-dimethyl-1-ethenyl-hexyl-4-enyl acetate; p-meth-1-en-8-yl acetate; 4-(2,6,6-trimethyl-2-cyclohexenyl)-3-buten-2-one; 4-acetoxy-3-methoxy-1-propenylbenzene; 2-propenyl cyclohexanepropionate; bicyclo[2.2.1]hept-5-ene-2-carboxylic acid,3-(1-methylethyl)-ethyl ester; bycyclo [2.2.1]heptan-2-ol, 1,7,7-trimethyl-, acetate; 1,5-dimethyl-1-ethenylhex-4-enylacetate; hexyl 2-methyl propanoate; ethyl-2-methylbutanoate; 4-undecanolide; 5-heptyldihydro-2(3h)-furanone;1,6-nonadien-3-o1,3,7dimethyl-; 3,7-dimethylocta-1,6-dien-3-o; 3-cyclo-hexene-1-carboxaldehyde,dimethyl-;3,7-dimethyl-6-octene nitrile; 4-(2,6,6-trimethyl-1-cyclohexenyl)-3-buten-2-one; tridec-2-enonitrile; patchouli oil; ethyl tricycle [5.2.1.0]decan-2-carboxylate; 2,2-dimethyl-cyclohexanepropanol; hexyl ethanoate, 7-acetyl,1,2,3,4, 5,6,7,8-octahydro-1,1,6,7-tetramethyl naphtalene; allyl-cyclohexyloxy acetate; methyl nonyl acetic aldehyde; 1-spiro[4,5]dec-7-en-7-yl-4-pentenen-1-one; 7-octen-2-ol,2-methyl-6-methylene-,dihydro; cyclohexanol,2-(1,1-dimethylethyl)-, acetate; hexahydro-4,7-methanoinden-5(6)-yl propionatehexahydro-4,7-methanoinden-5(6)-yl propionate; 2-methoxynaphtalene; 1-(2,6,6-trimethyl-3-cyclohexenyl)-2-buten-1-one; 1-(2,6,6-trimethyl-2-cyclohexenyl)-2-buten-1-one; 3,7-dimethyloctan-3-ol; 3-buten-2-one,3-methyl-4-(2,6,6-trimehtyl-1-cyclohexen-2-yl)-; hexanoic acid, 2-propenyl ester; (Z)-non-6-en-1-al;1-decyl aldehyde; 1-octanal; 4-t-butyl-α-methylhydrocinnamaldehyde; alpha-hexylcinnamaldehyde; ethyl-2,4-hexadienoate; 2-propenyl 3-cyclohexanepropanoate; and mixtures thereof;
(r) a perfume composition comprising, based on total perfume composition weight, at least 20% of a material selected from the group consisting of: 1-methylethyl-2-methylbutanoate; ethyl-2-methyl pentanoate; 1,5-dimethyl-1-ethenylhex-4-enyl acetate; p-meth-1-en-8-yl acetate; 4-(2,6,6-trimethyl-2-cyclohexenyl)-3-buten-2-one; 4-acetoxy-3-methoxy-1-propenylbenzene; 2-propenyl cyclohexanepropionate; bicyclo[2.2.1]hept-5-ene-2-carboxylic acid,3-(1-methylethyl)-ethyl ester; bycyclo [2.2.1]heptan-2-ol, 1,7,7-trimethyl-, acetate; 1,5-dimethyl-1-ethenylhex-4-enyl acetate; hexyl 2-methyl propanoate; ethyl-2-methylbutanoate,4-undecanolide; 5-heptyldihydro-2(3h)-furanone; 5-hydroxy-dodecanoic acid; decalactones; undecalactones, 1,6-nonadien-3-o1,3,7dimethyl-; 3,7-dimethylocta-1,6-dien-3-ol; 3-cyclohexene-1-carboxaldehyde,dimethyl-; 3,7dimethyl-6-octene nitrile; 4-(2,6,6-trimethyl-1-cyclohexenyl)-3-buten-2-one; tridec-2-enonitrile; patchouli oil; ethyl tricycle [5.2.1.0]decan-2-carboxylate; 2,2-dimethyl-cyclohexanepropanol; allyl-cyclohexyloxy acetate; methyl nonyl acetic aldehyde; 1-spiro[4,5]dec-7-en-7-yl-4-pentenen-1-one; 7-octen-2-ol,2-methyl-6-methylene-,dihydro, cyclohexanol,2-(1,1-dimethylethyl)-, acetate; hexahydro-4,7-methanoinden-5(6)-yl propionatehexahydro-4,7-methanoinden-5(6)-yl propionate; 2-methoxynaphtalene; 1-(2,6,6-trimethyl-3-cyclohexenyl)-2-buten-1-one;1-(2,6,6-trimethyl-2-cyclohexenyl)-2-buten-1-one; 3,7-dimethyloctan-3-ol; 3-buten-2-one,3-methyl-4-(2,6,6-trimehtyl-1-cyclohexen-2-yl)-; hexanoic acid, 2-propenyl ester; (Z)-non-6-en-1-al; 1-decyl aldehyde; 1-octanal; 4-t-butyl-α-methylhydrocinnamaldehyde; ethyl-2,4-hexadienoate; 2-propenyl 3-cyclohexanepropanoate; and mixtures thereof;
(s) a perfume composition comprising, based on total perfume composition weight, at least 5% of a material selected from the group consisting of 3-cyclohexene-1-carboxaldehyde,dimethyl-; 3-buten-2-one,3-methyl-4-(2,6,6-trimehtyl-1-cyclohexen-2-yl)-; patchouli oil; Hexanoic acid, 2-propenyl ester; 1-Octanal; 1-decyl aldehyde; (Z)-non-6-en-1-al; methyl nonyl acetic aldehyde; ethyl-2-methylbutanoate; 1-methylethyl-2-methylbutanoate; ethyl-2-methyl pentanoate; 4-hydroxy-3-ethoxybenzaldehyde; 4-hydroxy-3- methoxybenzaldehyde; 3-hydroxy-2-methyl-4-pyrone; 3-hydroxy-2-ethyl-4-pyrone and mixtures thereof;
(t) a perfume composition comprising, based on total perfume composition weight, less than 10% perfumes having a Clog P greater than 5.0;
(u) a perfume composition comprising geranyl palmitate; and
(v) a perfume composition comprising a first and an optional second material, said first material having:
(i) a Clog P of at least 2;
(ii) a boiling point of less than about 280° C.; and
second optional second material, when present, having
(a) a Clog P of less than 2.5.

14. A composition according to claim 1, comprising a material selected from the group consisting of, a structurant, an anti-agglomeration agent and mixtures thereof.

15. A composition according to claim 1, comprising less than 150 ppm formaldehyde.

16. A composition according to claim 1, having a viscosity of from 1 to 1500 centipoises (1-1500 mPa*s) at 20 s and 21° C.

17. A composition according to claim 1, comprising from about 0.001% to about 25%, based on total consumer product mass weight of said benefit agent delivery particles.

18. A composition according to claim 1, comprising a structurant, said structurant comprising a material selected from the group consisting of polysaccharides, modified celluloses, modified proteins, inorganic salts, quaternized polymeric materials, imidazoles; nonionic polymers having a pKa less than 6.0, polyurethanes, bacterial cellulose, coated bacterial cellulose, non-polymeric crystalline hydroxyl-functional materials, polymeric structuring agents, di-amido gellants and mixtures thereof.

* * * * *